Figure 1:
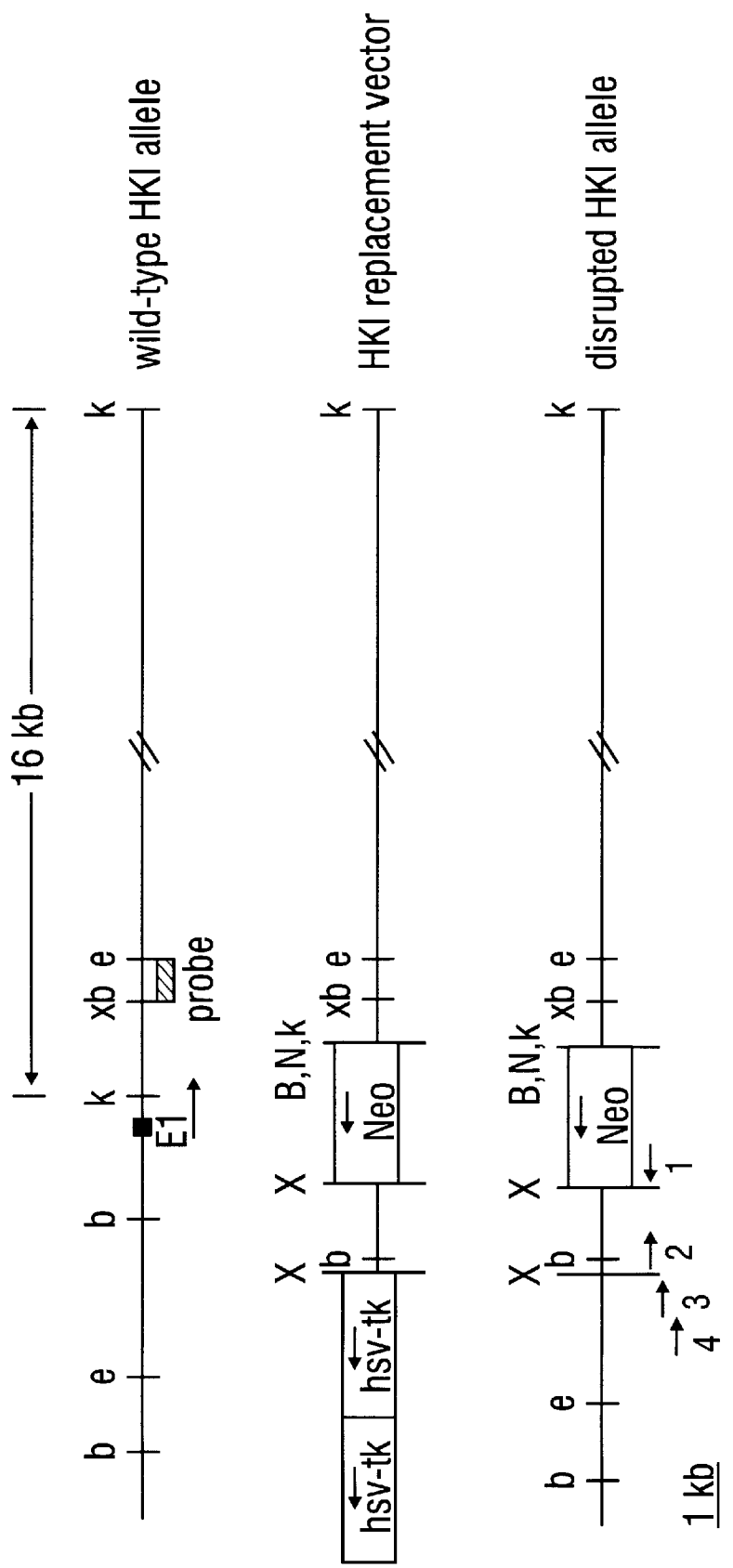

United States Patent [19]
Newgard et al.

[11] Patent Number: 6,087,129
[45] Date of Patent: Jul. 11, 2000

[54] RECOMBINANT EXPRESSION OF PROTEINS FROM SECRETORY CELL LINES

[75] Inventors: Christopher B. Newgard; Karl D. Normington, both of Dallas; Samuel A. Clark, Rockwall; Anice E. Thigpen, Dallas; Christian Quaade, Dallas; Fred Kruse, Dallas, all of Tex.

[73] Assignees: Betagene, Inc., Dallas; Board of Regents, The University of Texas System, Austin, both of Tex.

[21] Appl. No.: 08/589,028

[22] Filed: Jan. 19, 1996

[51] Int. Cl.[7] .............................. C12P 21/00; C12P 21/06; C12Q 1/68
[52] U.S. Cl. .............................. 435/69.4; 435/69.1; 435/6
[58] Field of Search .............................. 435/69.1, 6, 69.4; 514/44

[56] References Cited

U.S. PATENT DOCUMENTS

| | | | |
|---|---|---|---|
| 4,353,888 | 10/1982 | Sefton | 424/25 |
| 4,959,317 | 9/1990 | Sauer | 435/172.3 |
| 5,002,661 | 3/1991 | Chick et al. | 210/192 |
| 5,112,945 | 5/1992 | Westermark et al. | 530/324 |
| 5,367,052 | 11/1994 | Cooper et al. | 530/307 |
| 5,534,404 | 7/1996 | Laurance | 435/3 |
| 5,773,255 | 6/1998 | Laurance et al. | 435/70.3 |

FOREIGN PATENT DOCUMENTS

| | | | |
|---|---|---|---|
| WO 91/09939 | 7/1991 | WIPO . | |
| WO 96/31242 | 10/1996 | WIPO | A61K 48/00 |

OTHER PUBLICATIONS

Thorens et al., "Cloning and Functional Expression in Bacteria of a Novel Glucose Transporter Present in Liver, Intestine, Kidney, and β–Pancreatic Islet Cells," *Cell*, 55:281–290, 1988.

Willnow, et al, "Homologous Recombination for Gene . . . " Methods In Cell Biology 43: 305–334, 1994.

Kaufman, et al, "Construction of a Dihydrofolate . . . " Mol. Cell. Biol. 2(11): 1304–1319, 1982.

Becker, et al, "Use of Recombinant Adenovirus for Metabolic . . . ", Methods In Cell Biology 43:161–189, 1994.

Drucker, et al, "Cell–specific Post–translational Processing of . . . " J. Biol. Chem. 261(21):9637–9643, 1986.

Efrat, et al, "Murine–Insulinoma Cell Line with . . . " Diabetes 42:901–907, 1993.

Dickerson, et al, "Transfected Human Neuropeptide Y . . . " J. Biol. Chem. 262(28): 13646–13653, 1987.

Altman, J.J. et al., "Long–Term Plasma Glucose Normalization in Experimental Diabetic Rats With Macroencapsulated Implants of Benign Human Insulinomas," *Diabetes*, 35:625–633, 1986.

O'Shea, G.M. and Sun, A.M., "Encapsulation of Rat Islets of Langerhans Prolongs Xenograft Survival in Diabetic Mice," *Diabetes*, 35:943–946, 1986.

*Primary Examiner*—Eggerton A. Campbell
*Attorney, Agent, or Firm*—Arnold, White & Durkee

[57] ABSTRACT

The present invention a provides methods for production of heterologous polypeptides using a variety recombinantly engineered secretory cell lines. The common feature of these cell lines is the absence of expression of at least one endogenous polypeptide. The host cell machinery normally used to produce the endogenous polypeptide is then usurped for the purpose of making the heterologous polypeptide. Also described are methods engineering cells for high level expression, methods of large scale protein production, and methods for treatment of disease in vivo using viral delivery systems and recombinant cell lines.

26 Claims, 17 Drawing Sheets

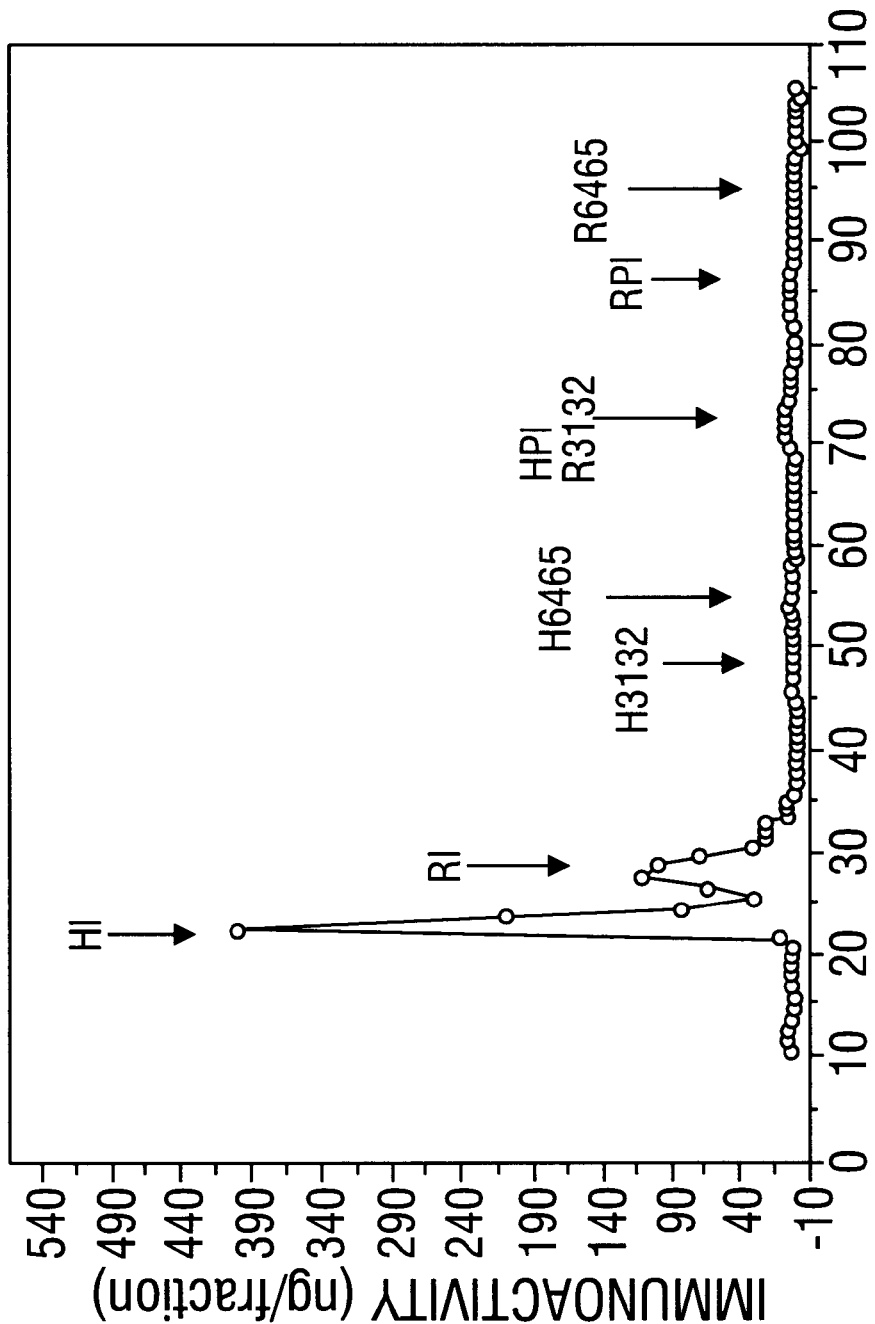

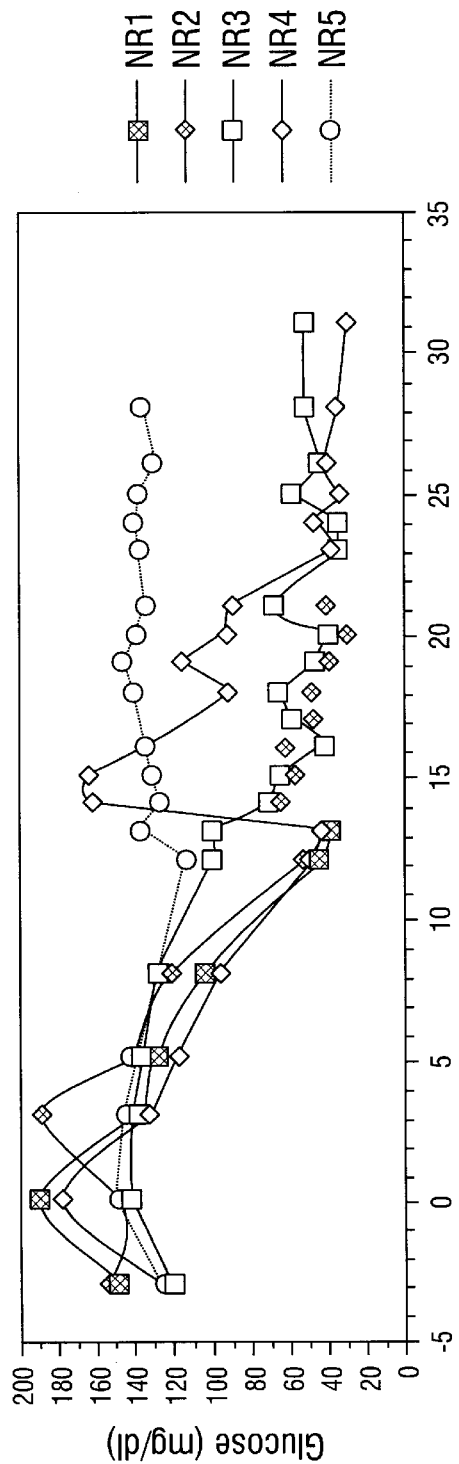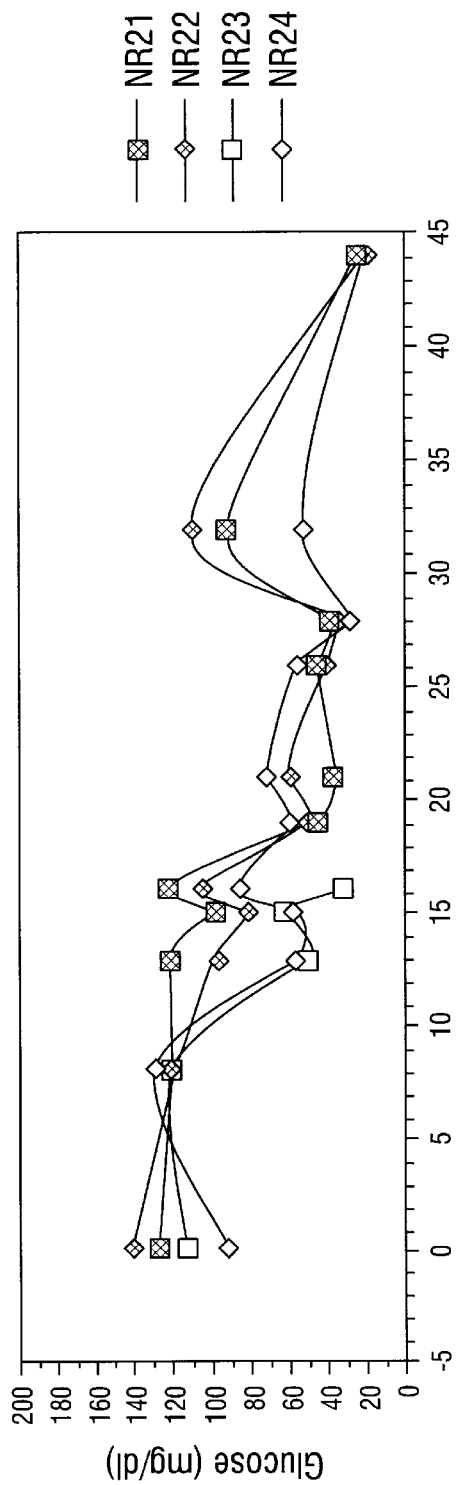
FIG. 6A
FIG. 6B

RECOMBINANT EXPRESSION OF PROTEINS FROM SECRETORY CELL LINES

I. BACKGROUND OF THE INVENTION

A. Field of the Invention

The present invention is related to the recombinant expression of proteins from eukaryotic cells. More particularly, the invention relates to the production of recombinant proteins from genetically engineered secretory cells. Methods for use of the cells also are provided.

B. Related Art

Mammalian cells of neuroendocrine origin have been used extensively over the last fifteen years as systems for the study of pathways and mechanisms of polypeptide secretion (Burgess and Kelly, 1987 and Chavez et al., 1994). Examples of cell lines in which such studies have been carried out in include the mouse pituitary line AtT-20 (ATCC CCL 89), the rat pituitary growth hormone secreting lines GH3 (ATCC CCL 82.1), the insulin secreting βTC lines derived from transgenic mice expressing SV40 T antigen (Efrat et al., 1988), radiation induced, rat islet cell tumor derived RIN lines (Gazdar, et al., 1980) and the rat adrenal pheochromocytoma cell line PC12 (ATCC CRL 1721). These cell lines maintain many of their endogenous functions, including synthesis of peptide hormones destined for the regulated secretory pathway. These cell lines also are transfectable, allowing expression of novel transgenes for studies of heterologous protein systems.

Three major areas have been studied using these heterologous systems. The first is the study of the sorting mechanism, whereby a given protein, destined for secretion, is targeted to the regulated secretory pathway or the default constitutive secretory pathway. The second relates to understanding the complex process of secretory protein maturation. This would include the specific steps of protein folding, disulfide bond formation, glycosylation, endoproteolytic processing and post-translational modifications of specific amino acids as well as understanding the enzymes involved in these processes. And the third relates to control of the regulated release of peptide hormones from secretory granules following physiological stimuli.

Neuroendocrine cell lines have been generated in which genes encoding specific peptide hormones have been stably inserted. These enzymes include insulin (Moore et al., 1983, Powell et al., 1988 and Gross et al., 1989), somatostatin (Sevarino et al., 1987), thyrotropin-releasing hormone (Sevarino et al., 1989), neuropeptide Y (Dickerson et al., 1987), insulin-like growth factor-1 (Schmidt and Moore, 1994), proopiomelanocortin (Thorne et al., 1989), glucagon (Drucker et al., 1986 and Rouille et al., 1994), pancreatic polypeptide (Takeuchi et al., 1991) and growth hormone (Moore and Kelly, 1985). In general, heterologous expression of these proteins has demonstrated faithful sorting to the regulated secretory pathway, as well as maturation of the proteins in the secretory granules. However, the expression levels of the heterologous proteins have generally been low when compared to normal endogenous expression of the same proteins in a homologous system.

Neuroendocrine cell lines expressing the enzymes involved in the processing of peptide hormones in secretory granules also have been generated. These include the endoproteases PC2 and PC3 (Ohagi et al., 1992, Benjannet et al., 1993, and Rouille et al., 1995) and peptidylglycine alpha-amidating monooxygenase (PAM) (Milgram et al., 1992 and Yun and Eipper, 1995). Overexpression of these processing enzymes has helped dissect their relative contributions to peptide hormone processing as well as their intracellular sites of action. These studies demonstrate the academic use of neuroendocrine cells in studying the regulated secretory pathway.

A series of papers over the last five years has addressed the possibility of production of heterologous peptide hormones in neuroendocrine cells. Three of these reports (Sambanis et al., 1990 and 1991, Grampp et al., 1992) use previously established AtT-20 lines expressing either insulin (Moore et al., 1983) or growth hormone (Moore and Kelly, 1985). The highest level of secretion of insulin under stimulated conditions was in the range of 35 to 144 microunits/million cells/hour (equivalent to 1 to 5 ng insulin/million cells/hr). Growth hormone secretion under stimulated conditions was 130 to 340 ng/million cells/hour. These levels of production are well below those reported in the literature for growth hormone production from other recombinant systems (Pavlakis and Hamer, 1983 and Heartlein et al., 1994). Another study dealing with protein production from a neuroendocrine cell makes use of an insulinoma line engineered to express prolactin (Chen et al., 1995). Absolute levels of production of prolactin on a per cell basis are not reported. A neuroendocrine cell-based system for either in vitro, biologically active peptide hormone production or for in vivo, cell-based delivery of biologically active peptide hormones has not been achieved in any of these earlier studies.

At least five important features must be addressed before a neuroendocrine cell-based system for protein production can be developed. The first feature is the absolute level of production of the polypeptide in question. A sufficiently high level of production to make either in vitro purification or in vivo efficacy must be achieved. As stated above, while many groups have reported expression of recombinant proteins in neuroendocrine lines, the proteins are produced at very low levels.

The second feature is the need for quantitative processing of the peptide to their biologically active forms. Neuroendocrine cell lines maintain variable levels of the enzymes responsible for peptide hormone processing and in many lines the enzyme levels may be insufficient to ensure sufficient processing. This is a critical parameter, especially as attempts are made to engineer high level production of specific peptide hormone transgenes.

The third feature is the need to maintain a dynamic response of the regulated secretory pathway. For both in vivo and in vitro use of a neuroendocrine cell-based system, the ability to quickly release high concentrations of the biologically active peptide by extracellular stimuli is important. In vivo modulation of peptide hormone release is required for titrating the biological efficacy of the cell-based delivery. In vitro modulation of peptide hormone release establishes efficient production of highly enriched fractions of starting material for subsequent purification.

The fourth feature is the ability to further engineer other functions into neuroendocrine cells other than just the high-level production of a given polypeptide. This further engineering could involve augmenting the cells capabilities such that any of the three previous points are improved or stabilized (i.e., increased protein levels, increased processing efficiencies or increased dynamic regulated secretory response).

The final engineering maneuver of significance is the ability to reduce or completely ablate the endogenous expression of an unwanted gene product. Reduction or ablation may result in an improved capability to produce, process or release the heterologous polypeptide. Such maneuvers also may confer advantages by removing unwanted or contaminating biological properties of the endogenous peptide hormone. Endogenous peptide production also might counteract the biological activities of the exogenous peptide hormone being produced, resulting in unwanted immunological reactions, reducing the capacity of the engineered lines to quantitatively produce the exogenously engineered protein or complicating purification of the exogenously produced protein. Because all of the existing neuroendocrine cell lines produce endogenous secreted proteins, these concerns are significant.

Thus, despite the benefits of developing a secretory cell line in which the protein synthetic machinery has been commandeered for the production of a heterologous polypeptide, there appear to be significant technical obstacles that are not addressed by the art. As a result, there currently exist no engineered cells that address all of these problems.

II. SUMMARY OF THE INVENTION

The present invention pertains to the engineering of mammalian cells for production of heterologous proteins, for example, in the production of secreted peptide hormones. These mammalian cells also are engineered such that production of at least one endogenous gene is blocked by molecular engineering, i.e., permitting the usurping of the machinery for the production of the heterologous protein.

Therefore, there is provided a method for producing a polypeptide comprising providing a secretory host cell, blocking the production of an endogenous, secreted polypeptide, contacting with the host cell an exogenous polynucleotide comprising a gene encoding an exogenous polypeptide, wherein the gene is under the control of a promoter active in eukaryotic cells, and culturing the secretory host cell under conditions such that the exogenous polynucleotide expresses the exogenous polypeptide.

In particular embodiments, the promoter is selected from the group consisting of CMV, SV40 IE, RSV LTR, GAPHD and RIP1. The exogenous polynucleotide may further comprise an adenovirus tripartite 5' leader sequence and intron, and the intron may comprise the 5' donor site of the adenovirus major late transcript and the 3' splice site of an immunoglobulin gene. The exogenous polynucleotide may further comprise a polyadenylation signal.

The secretory host cell may be a neuroendocrine cell, such as an insulinoma, more particularly, a rat insulinoma cell or a human insulinoma cell. It also may be glucose responsive or non-glucose responsive.

The exogenous polypeptide may be secreted, amidated or a fusion protein. Amidated polypeptides include calcitonin, calcitonin gene related peptide (CGRP), β-calcitonin gene related peptide, hypercalcemia of malignancy factor (1-40) (PTH-rP), parathyroid hormone-related protein (107-139) (PTH-rP), parathyroid hormone-related protein (107-111) (PTH-rP), cholecystokinin (27-33) (CCK), galanin message associated peptide, preprogalanin (65-105), gastrin I, gastrin releasing peptide, glucagon-like peptide (GLP-1), pancreastatin, pancreatic peptide, peptide YY, PHM, secretin, vasoactive intestinal peptide (VIP), oxytocin, vasopressin (AVP), vasotocin, enkephalins, enkephalinamide, metorphinamide (adrenorphin), alpha melanocyte stimulating hormone (alpha-MSH), atrial natriuretic factor (5-28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH).

The exogenous polypeptide may be a hormone, such as growth hormone, prolactin, placental lactogen, luteinizing hormone, follicle-stimulating hormone, chorionic gonadotropin, thyroid-stimulating hormone, adrenocorticotropin (ACTH), angiotensin I, angiotensin II, β-endorphin, β-melanocyte stimulating hormone (β-MSH), cholecystokinin, endothelin I, galanin, gastric inhibitory peptide (GIP), glucagon, insulin, lipotropins, neurophysins and somatostatin. In the case of insulin, recombinant cells having an insulin content of at last about 1000, 1250, 1500 and 2500 ng per $10^6$ cells are provided. Recombinant cells producing 200, 300, 400, 500 and 1000 ng of insulin per $10^6$ cells per hour also are provided. Recombinant cells secreting at least 25 μg of human growth hormone per $10^6$ cells per hour, at least 50 μg of human growth hormone per $10^6$ cells per hour and about 200 μg of human growth hormone per $10^6$ cells per hour are provided.

The exogenous polypeptide may be a growth factor, such as epidermal growth factor, platelet-derived growth factor, fibroblast growth factor, hepatocyte growth factor and insulin-like growth factor 1.

In a particular embodiment, the endogenous, secreted polypeptide and the exogenous polypeptide are the same, for example, where both the endogenous, secreted polypeptide and the exogenous polypeptide are insulin.

In another embodiment, the exogenous polypeptide enhances the production and/or secretion of at least one polypeptide produced by said cell, for example, a protein processing enzyme, a receptor and a transcription factor. Examples include hexokinase, glucokinase, GLUT-2, GLP-1, IPF1, PC2, PC3, PAM, glucagon-like peptide I receptor, glucose-dependent insulinotropic polypeptide receptor, BIR, SUR, GHRFR and GHRHR.

Other elements that may be included in the construct are a selectable marker and an internal ribosome entry site.

Methods for blocking of production of an endogenous, secreted polypeptide include expression of an RNA antisense to the DNA or mRNA corresponding to the endogenous, secreted polypeptide, production of ribozyme specific for the mRNA of the endogenous, secreted polypeptide, interruption of the gene encoding said endogenous, secreted polypeptide by homologous recombination or random integration.

Also contemplated by the present invention are large scale production methods including stirring a suspension of the secretory host cell, gas stream agitation of a suspension of the secretory host cell, incubation of the secretory host cell in a non-perfused attached cell container or a perfused attached cell container, culture on microcarriers, microencapsulation of the secretory host cell, followed by cell culture and incubation of the secretory host cell in a perfused packed bed reactor.

Also provided is a method of preventing type I diabetes comprising identifying a subject at risk of type I diabetes and providing to the subject a polynucleotide comprising a human insulin β-chain gene, wherein the β-chain gene is under the control of a promoter active in eukaryotic cells. The providing may comprise introducing the polynucleotide to a cell of the subject in vivo. Alternatively, the providing comprises contacting with a secretory host cell ex vivo and administering the secretory host cell to the subject. Further, the expression of the endogenous insulin β-chain in said secretory host cell may be blocked. An advantageous vehicle for providing of the polynucleotide is in a packageable, replication defective adenoviral expression construct.

A further embodiment includes a method for treating a subject afflicted with diabetes comprising identifying a subject afflicted with diabetes and providing to the subject a secretory host cell, wherein (i) the production of an endogenous, secreted polypeptide has been blocked and (ii) wherein the secretory host cell comprises an exogenous polynucleotide comprising a gene encoding insulin, wherein the gene is under the control of a promoter active in eukaryotic cells.

In yet another embodiment, there is provided a method for providing a polypeptide to an animal comprising the step of providing to the animal a secretory host cell, wherein (i) the production of an endogenous, secreted polypeptide in the secretory host cell has been blocked and (ii) wherein the secretory host cell comprises an exogenous polynucleotide comprising a gene encoding the polypeptide, wherein the gene is under the control of a promoter active in eukaryotic cells.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

III. BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 1: Map of wild-type HKI allele, vector for replacement, and disrupted HKI allele. Arrows indicate the direction of transcription of hexokinase 1 (E1 for exon 1 shown), neomycin resistance (positive selection gene) and the hsv-tk (negative selection gene). Oligos 1, 2, 3 and 4 used in PCR™ analysis are indicated. Capital bold letters indicate restriction enzyme sites introduced by the knock-out vector and lower case letters indicate sites in the endogenous gene. b, B=BamHI; e=EcoRI; k=KpnI; N=NotI; X=XhoI. The 16 kB KpnI fragment cloned from RIN 1046-38 genomic DNA is indicated as well as the probe used in genomic Southerns (FIG. 2).

Figure 2:
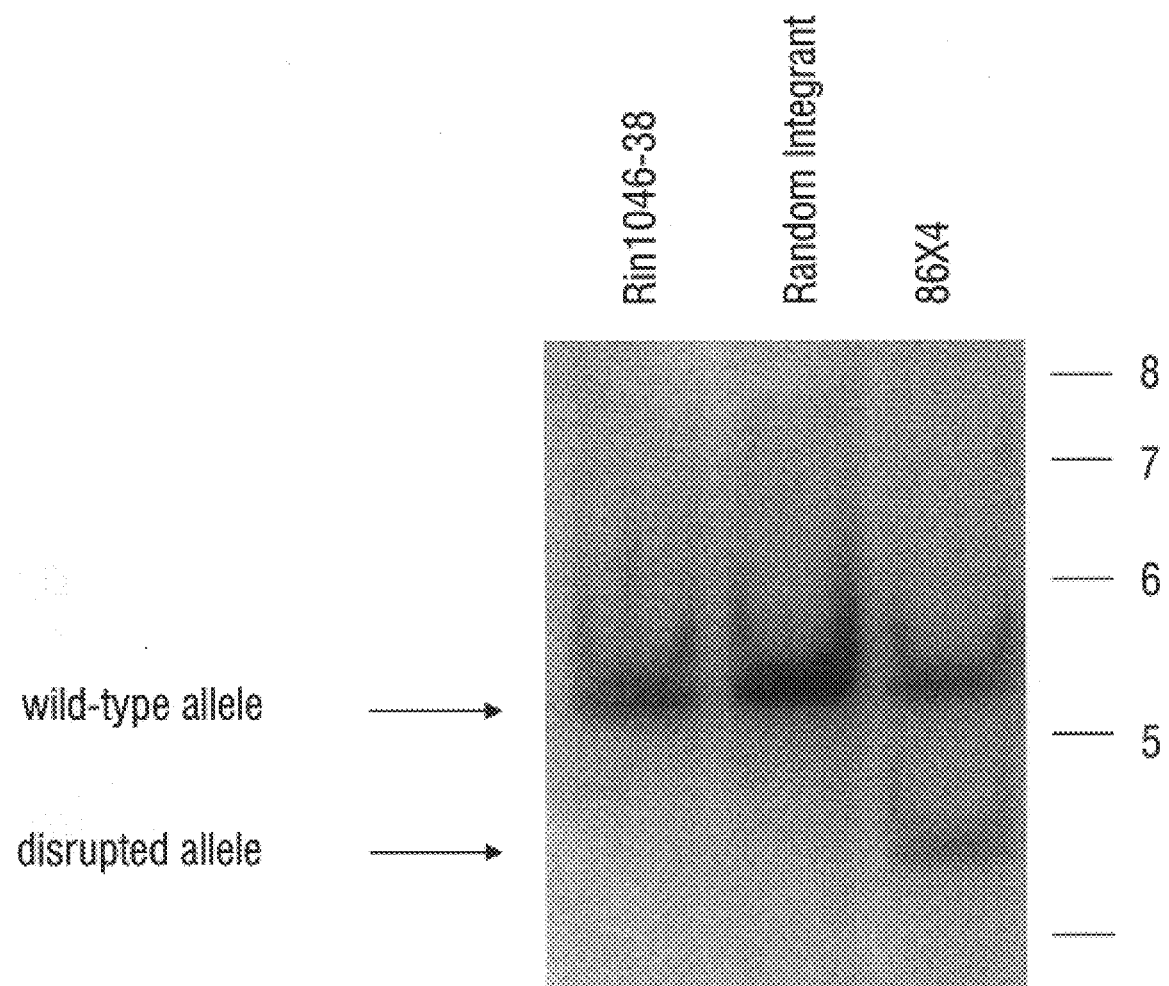

FIG. 2: Genomic Southern confirming hexokinase I gene disruption. The probe (hatched rectangle, FIG. 1) is a 1 kB Pst I fragment upstream of the recombination site. Genomic DNA was digested with NotI and EcoRI. The DNA in each lane is as follows: first lane, RIN 1046-38; second lane, RIN-52/17 containing a randomly integrated HKI replacement vector; and lane 3, RIN-52/17 containing a disrupted allele of the HKI gene (clone 86/X4).

Figure 3:
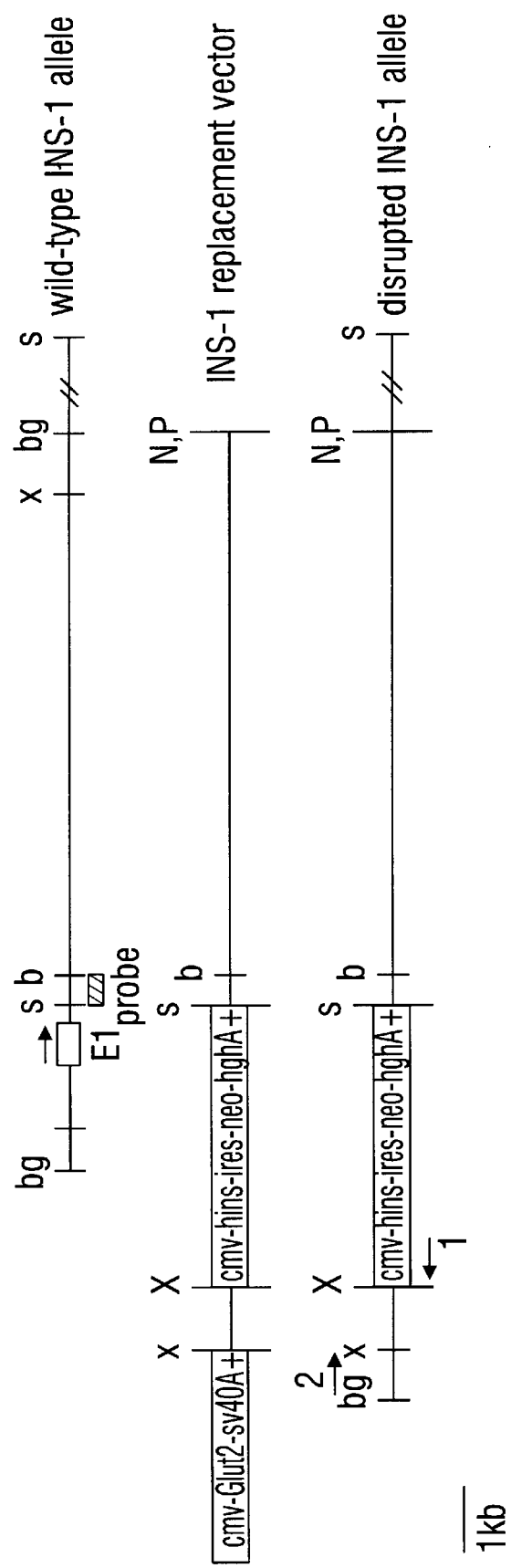

FIG. 3: Rat insulin 1 gene knockout strategy. Map of wild-type RIN insulin I (RINS-I) allele, vector for replacement, and disrupted RINS-I allele. Restriction enzyme sites are shown. Capital bold letters indicate sites introduced by the replacement vector and lower case letters indicate sites in the endogenous gene. b=BamHI; bg=BglII; N=NotI; P=PacI; s=SpeI; x, X=XhoI. The coding region for RINS-1 gene is indicated by the rectangle with an arrow showing the direction of transcription. The hatched rectangle indicates the sequence used as a probe in genomic Southerns. The arrows, 1 and 2, show the locations of the primers used to amplify genomic DNA specifically recombined at the RINS-1 gene.

Figure 4B:
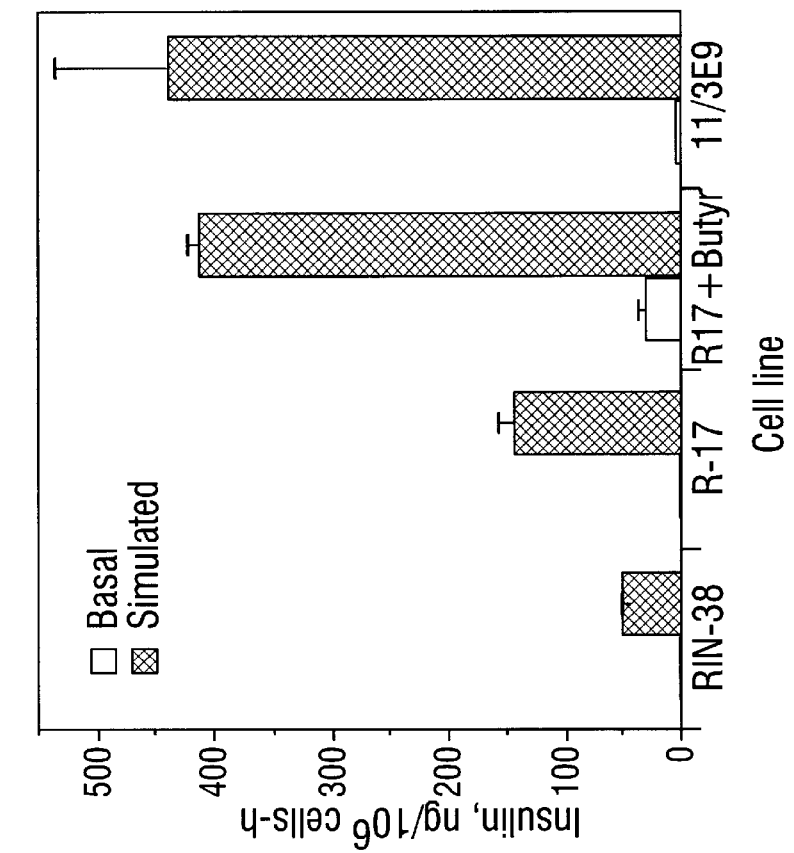
Figure 4A:
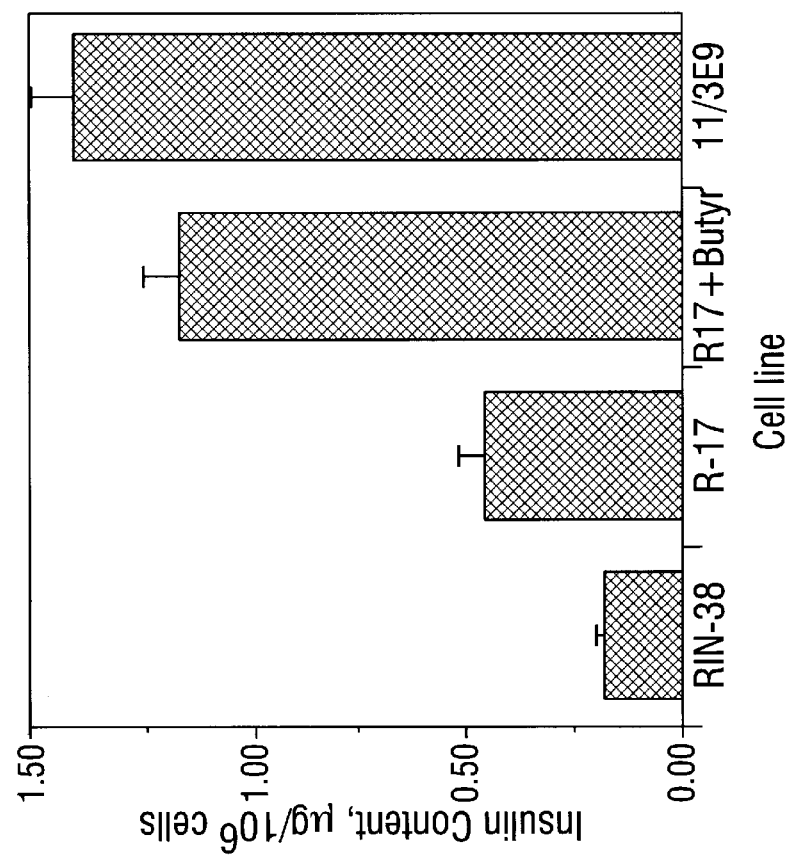

FIG. 4A: Insulin content in engineered cell lines. Immunoreactive insulin was determined from acid extracts prepared from the following cell lines: RIN 1046-38, R5C.I-17, R5C.I-17 chronically treated with 1.0 mM butyrate, and 11/3E9. Values are reported as $\mu$g of insulin per million cells.

FIG. 4B: Basal and stimulated insulin secretion from cell lines engineered to produce human insulin. Secreted immunoreactive insulin was determined from the following cell lines: RIN 1046-38, R5C.I-17, R5C.I-17 chronically treated with 1.0 mM butyrate, and 11/3E9. Basal samples are from a one hour incubation in media lacking glucose and containing 100 $\mu$M diazoxide. Stimulated samples are from cells incubated for one hour in media containing 5 mM glucose, 100 $\mu$M carbachol, 100 $\mu$M IBMX and amino acids. Values are reported as ng of insulin per million cells per hour.

Figure 5A:
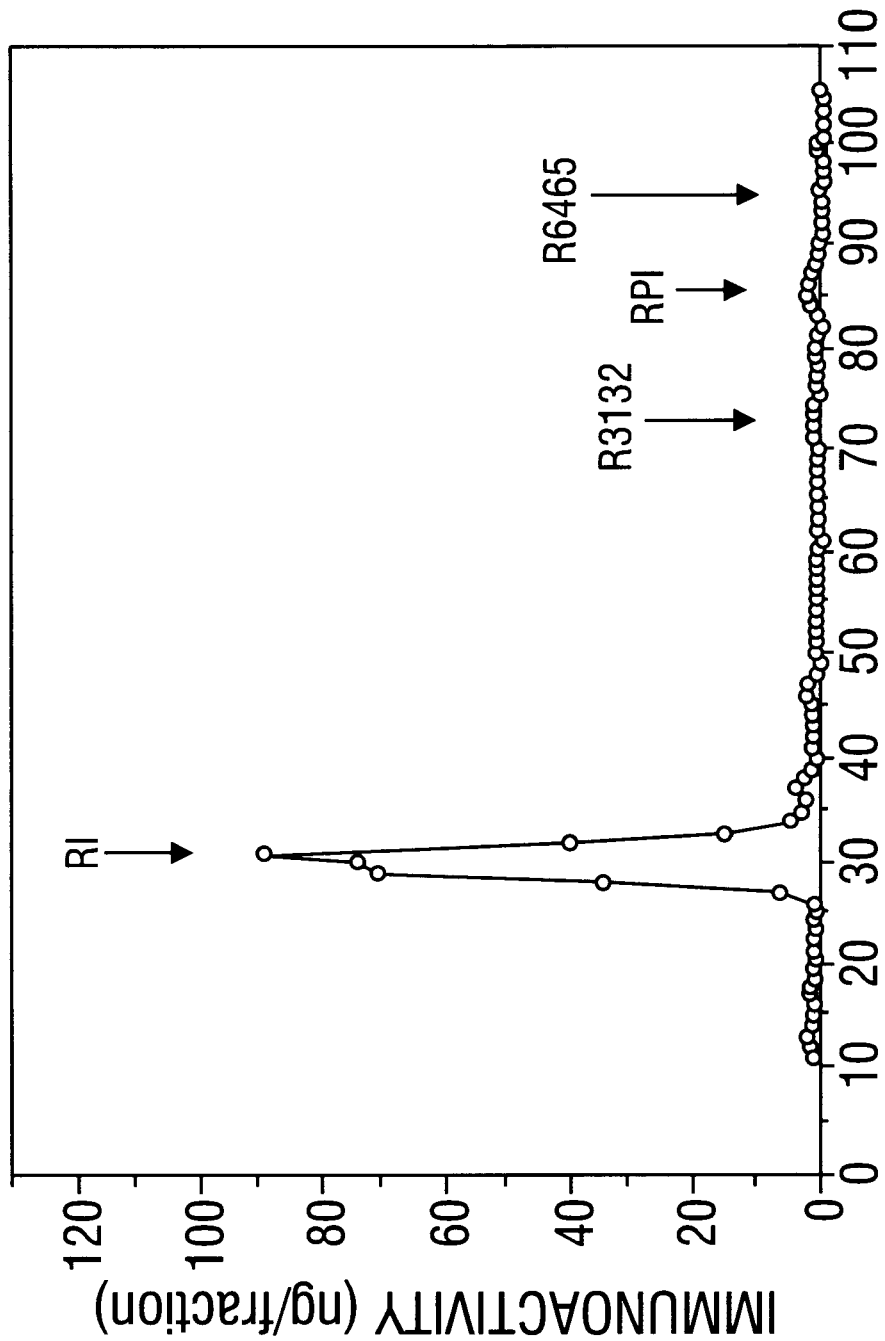
Figure 5B:
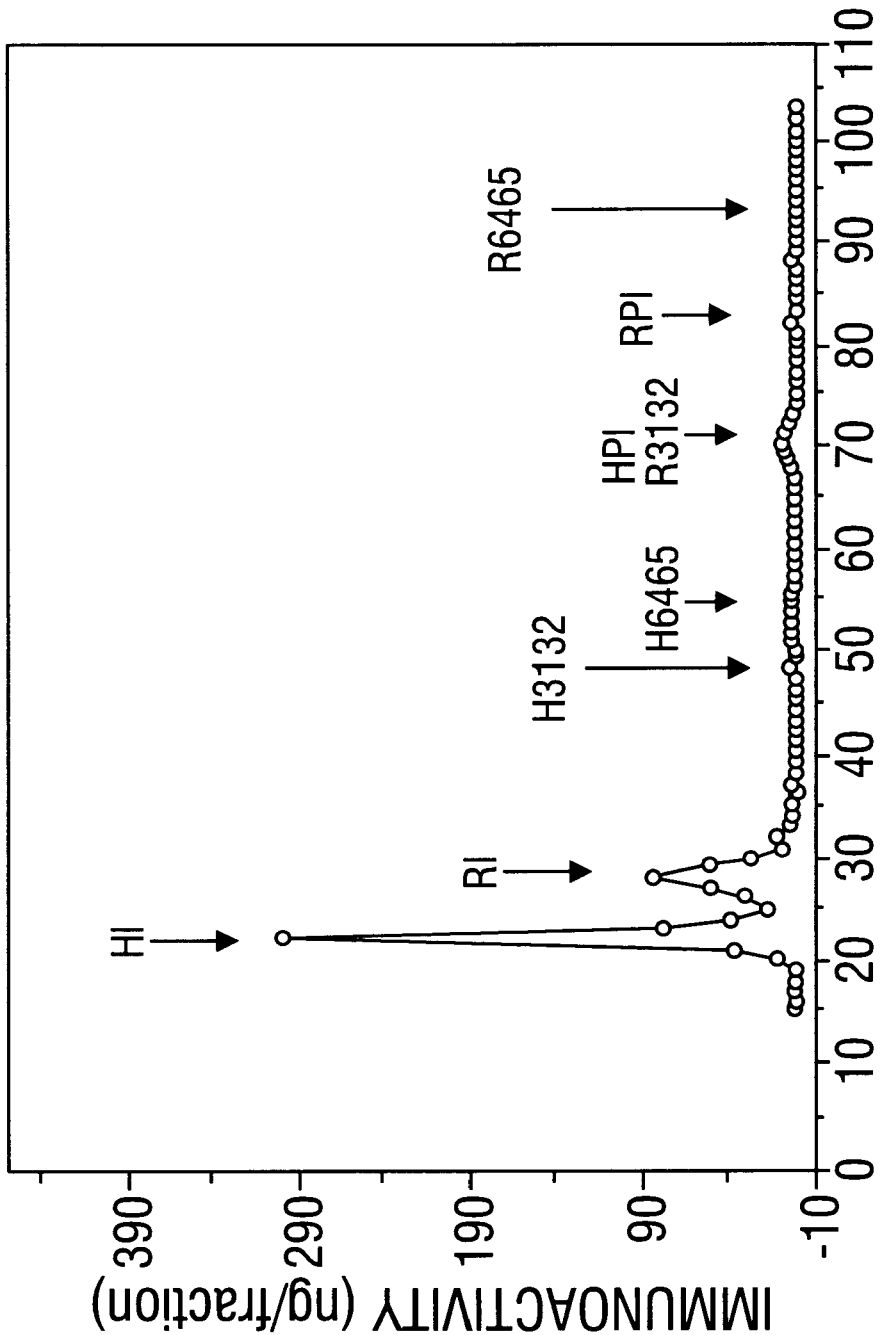

FIG. 5A, FIG. 5B, FIG. 5C: Human proinsulin is efficiently processed to mature insulin. Immunoreactive insulin was determined from HPLC fractionated acid/ethanol extracts prepared from RIN 1046-38 (FIG. 5A), R5C.I-17 (FIG. 5B) and EP11/3E9 (FIG. 5C). Arrows indicate positions where the following standards elute: mature rat and human insulin (RI and HI), rat and human proinsulin (RPI and HPI), and rat and human processing intermediates des-31,32- and des-64,65-split proinsulin (R 3132, R 6465, H 3132, and H 6465).

FIG. 6A and FIG. 6B: Blood glucose levels of nude rats injected with human insulin-producing cells. Nude rats were injected with either 3 million R5C.I-17 cells (NR1–4, FIG. 6A) or EP11/3E9 cells (NR21–24, FIG. 6B) on day 0. NR5 is an uninjected control animal. Blood glucose was determined on the indicated days. NR1, NR2 and NR23 died prematurely from severe hypoglycemia.

Figure 7:
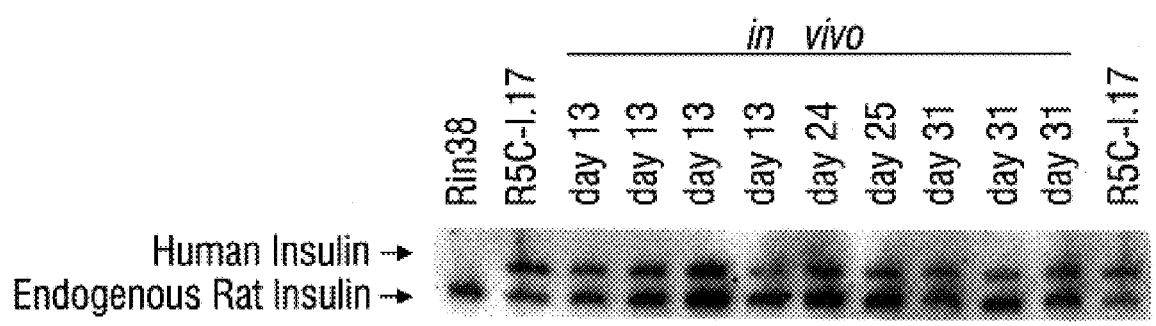

FIG. 7: Insulin message analysis from tumors explanted from nude rats injected with R5C.I-17 cells (see NR1–4. FIG. 6). Primer extension analysis of endogenous rat insulin produces a 91 base extended product (lower band) while the human insulin transgene produces a 101 base extended product (upper band). Analysis of in vitro maintained RIN 1046-38 is shown in the first lane and in vitro maintained R5C.I-17 is shown in the second and last lanes. The day of tumor explant is indicated for each in vivo sample.

Figure 8:
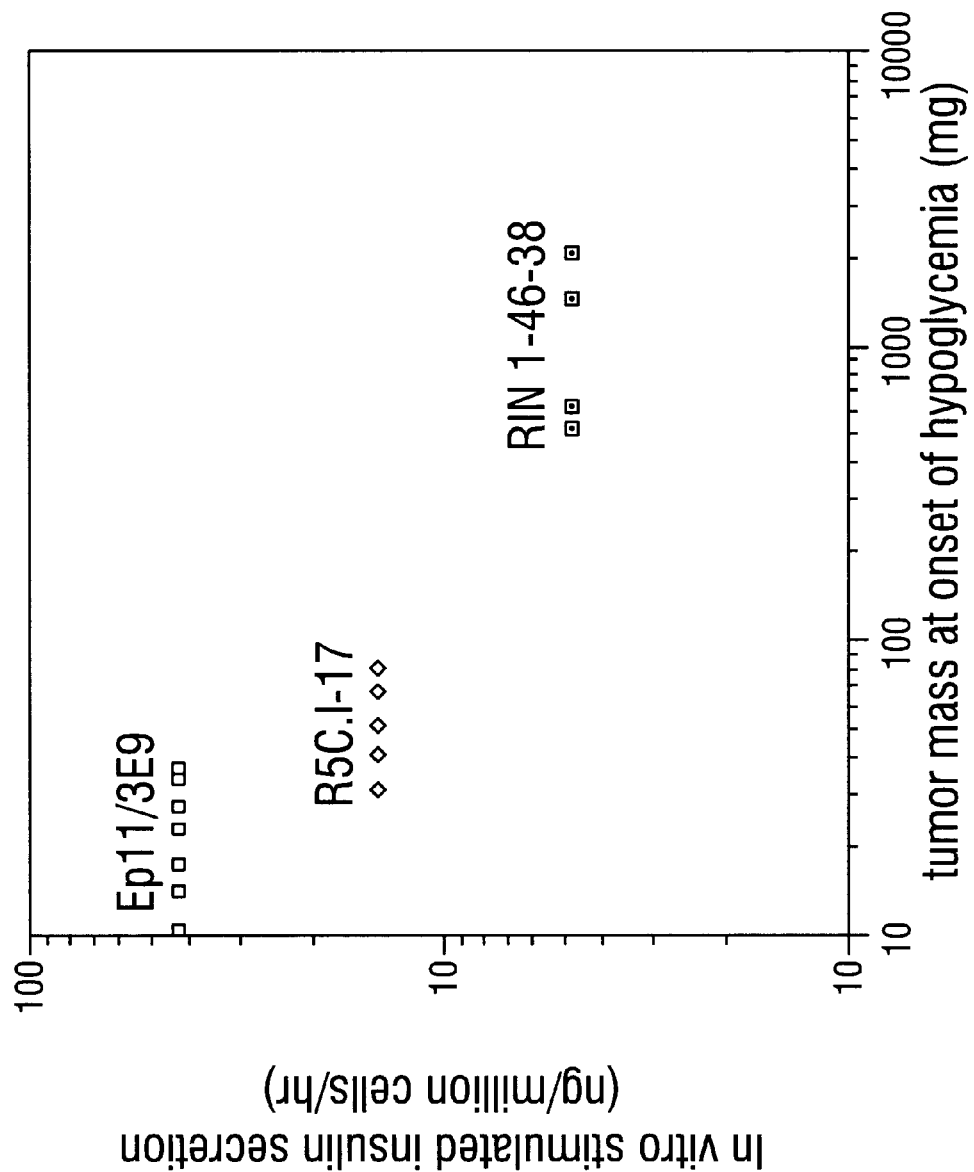

FIG. 8: In vivo potency of engineered RIN cell lines. The in vitro stimulated insulin secretion values of RIN 1046-38, RSC.I-17 and EP11/3E9 (see FIG. 4B) are compared to the explanted tumor mass at initial onset of hypoglycemia in nude rats (see FIG. 6). Individual tumor masses are indicated.

Figures 9, 10A, 10B:
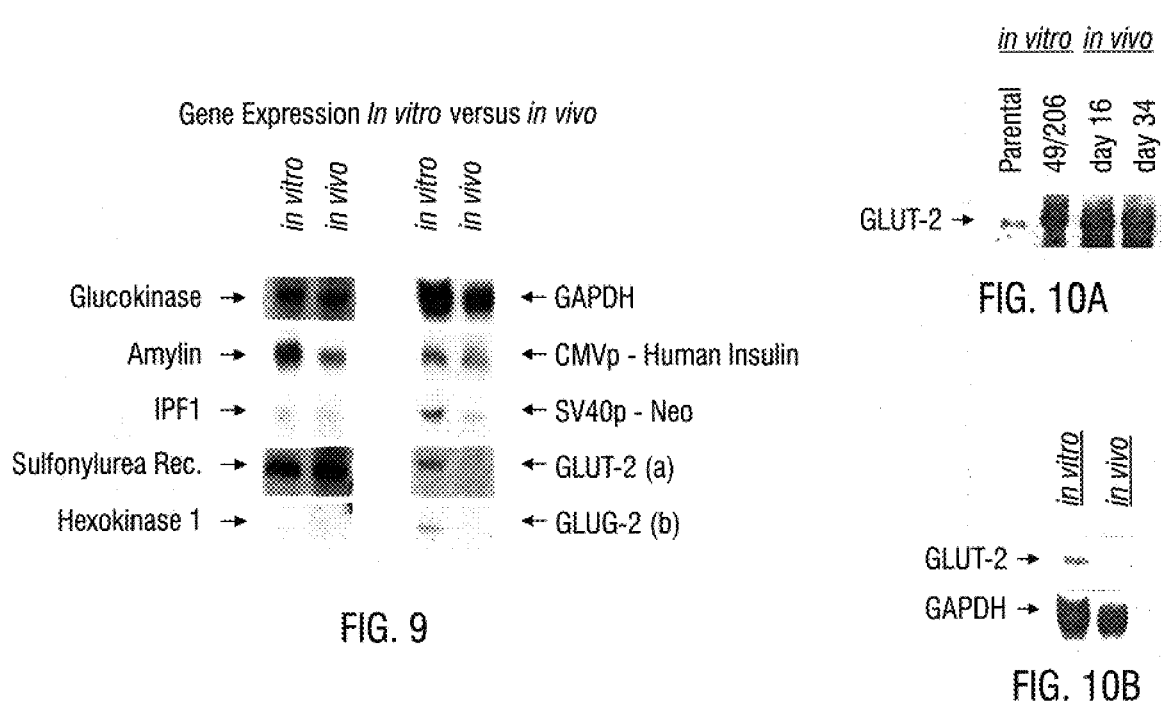

FIG. 9: Gene expression of many endogenous genes is stable in vitro versus in vivo with the noted exception of GLUT-2. Northern analysis of RNA from in vitro maintained cells versus day 25 in vivo tumors (R5C.I-17 cells). Signals on Northerns are running at correct sizes relative to published messages- islet GK - 2.8 kB (Hughes et al., 1991); GAPDH - 1.3 kB (Fort et al., 1985); amylin - 0.9 kB (Leffert et al., 1989); IPF1 - 1.4 kB (Leonard et al., 1993 and Miller et al., 1994); Sulfonylurea receptor - 5.1 kB (Aguilar-Bryan et al., 1995); HK1 - 3.7 kB (Schwab and Wilson, 1989); GLUT-2 - 2.6 kB (Thorens, et al., 1988); human insulin transgene - 0.7 kB (this study); and Neo transgene - 1.6 kB (this study).

FIG. 10A: GLUT-2 transgene expression as driven by the CMV promoter is stable in vitro and in vivo. Northern analysis of GLUT-2 transgene expression of a cell line expressing high levels of GLUT-2 (49/206) is maintained in vivo following a 16 or 34 day passage of the insulinoma in a nude rat model.

FIG. 10B: Low level of endogenous GLUT-2 expression seen in the parental RIN cells maintained in vitro (Lane 1. Panels A and B) is lost following a 24 day passage of the cells in vivo. The message for GAPDH serves as a loading control.

Figure 11:
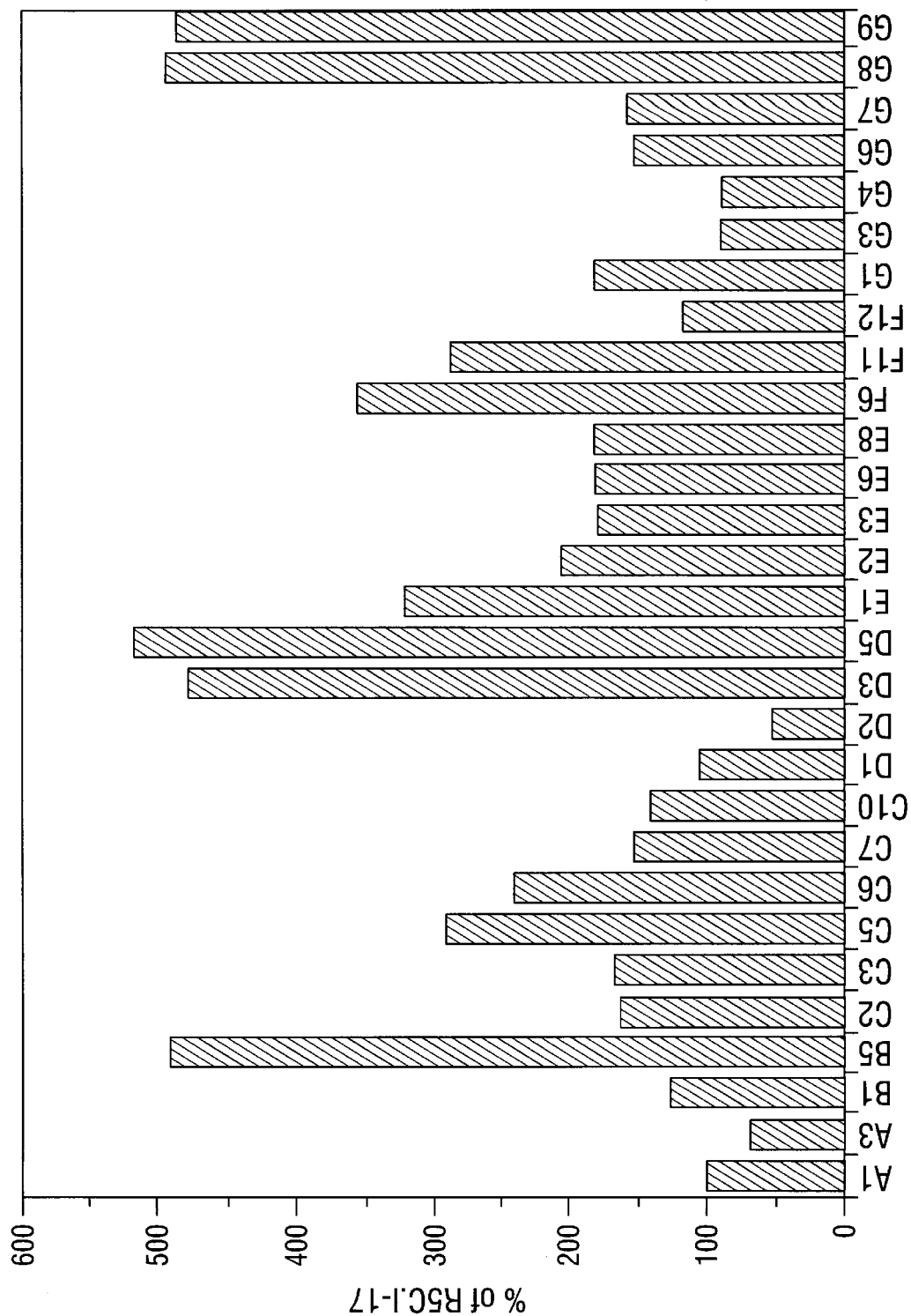

FIG. 11: Increased insulin content resulting from expression plasmids containing internal ribosome entry sites (IRES). Immunoreactive reactive insulin was determined from acid/ethanol extracts from 29 independent G418 resistant clones (EP18/3 clones) generated from pCMV8/INS/IRES/NEO. Values are reported as a percentage of the insulin content in R5C.I-17 cells.

Figure 12A:
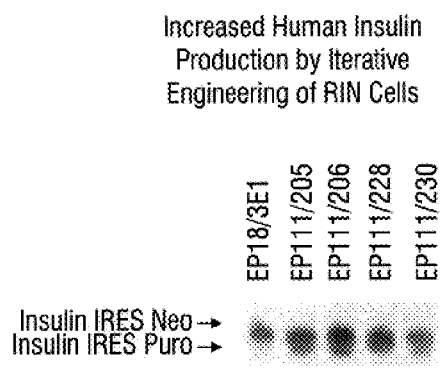

FIG. 12A: Higher human insulin-producing clones generated by iterative engineering of RIN clones with IRES-containing insulin expression plasmids. Northern analysis of EP18/3E1 (FIG. 11), a clone expressing a human insulin/IRES/NEO transgene (first lane) and clones of EP18/3E1 expressing a second transgene encoding human insulin/IRES/Puromycin (EP111/205, 206, 227, and 230). The neomycin containing message is 1.9 kB while the puromycin containing message is 1.7 kB. Messages were detected with a probe specific for human insulin.

Figure 12B:
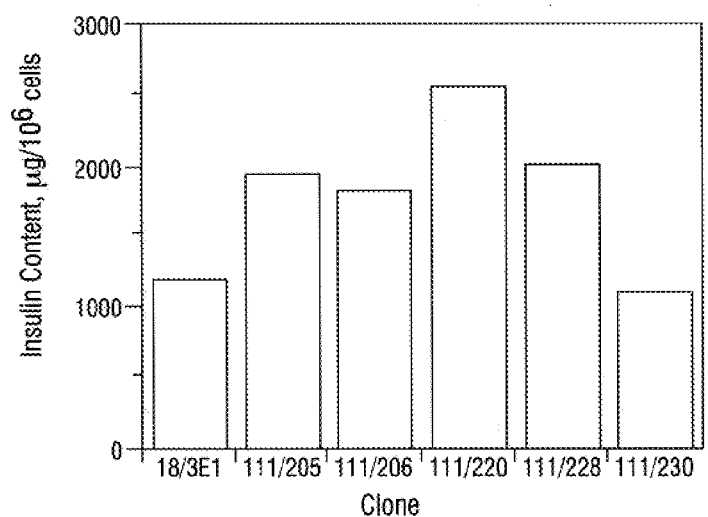

FIG. 12B: Increase in insulin content following iterative engineering of RIN clones. Insulin content was determined from acid/ethanol extracts of 18/3E1 cells and 5 clones derived from 18/3E1 expressing a second human insulin transgene (EP111/205, 206, 220, 228 and 230). Cell counts were determined as values are reported as ng insulin per million cells.

Figure 13:
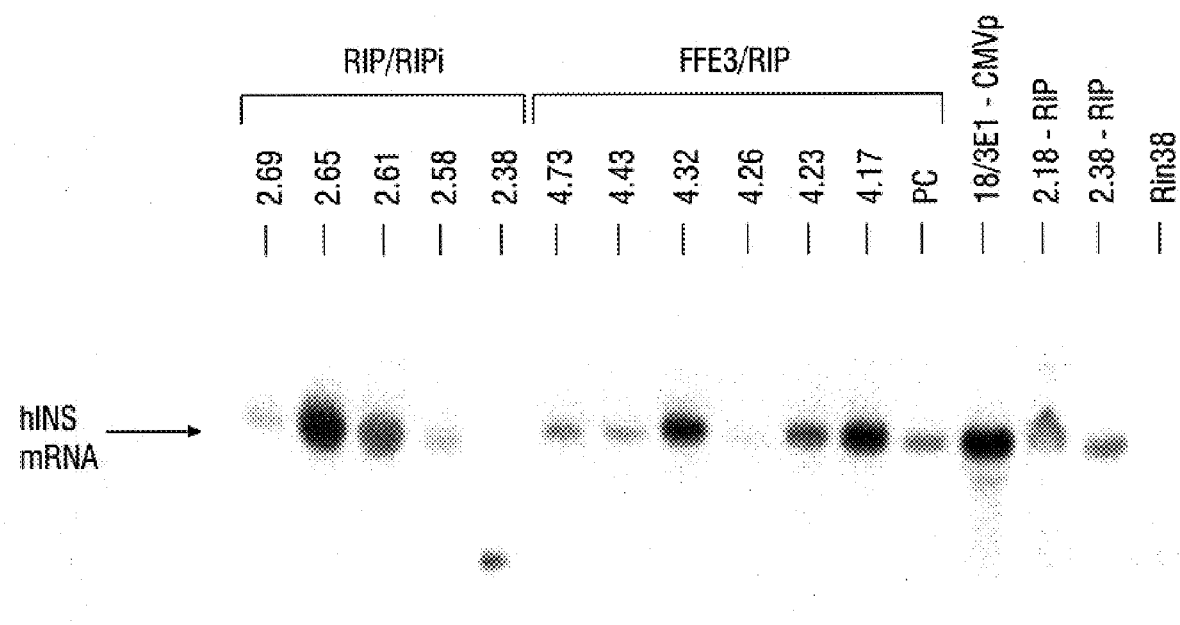

FIG. 13: Northern blot analysis of promoter activity in stably transfected RIN lines. Different promoters were driving expression of the common transgene, INS/IRES/NEO, were constructed. For RIP/RIPi, the 5' generic intron from INS/IRES/NEO was replaced with the rat insulin 1 gene intron (RIPi). All lanes contained 10 micrograms of total cellular RNA. The lane labelled RIN38 contains RNA from untransfected cells. The lane labeled PC (PolyClone) contains RNA from a pool of RIN38 clones transfected with pFFE3/RIP8/INS/IRES/NEO.

Figure 14:
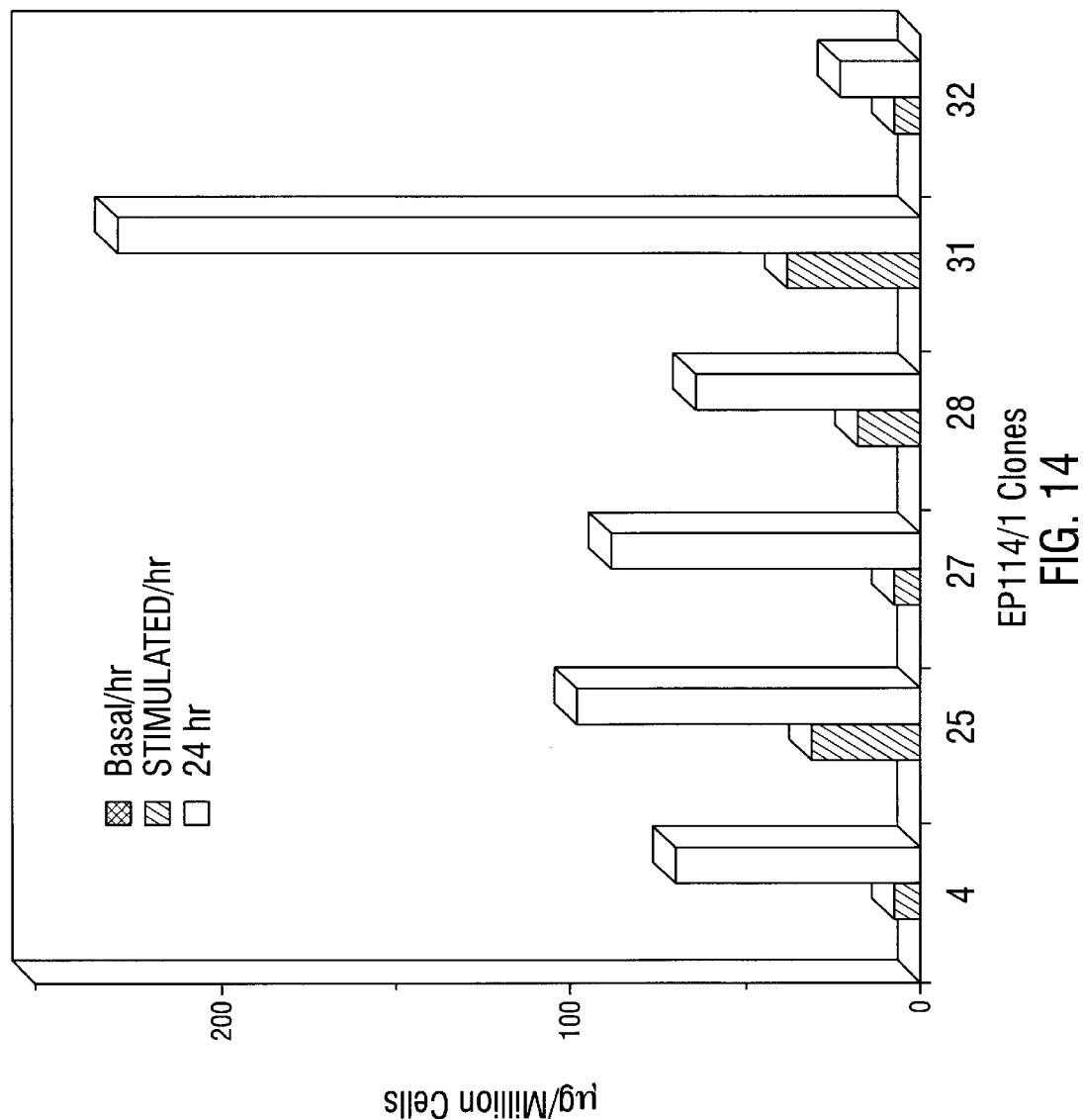

FIG. 14: Human growth hormone production in RIN cells. Secreted growth hormone was determined from six independent RIN clones. Conditioned media samples were collected from each following a one hour incubation in media lacking glucose and containing 100 µM diazoxide (Basal/hr), a one hour incubation in media containing 5 mM glucose, 100 µM carbachol, 100 µM IBMX and amino acids (Stimulated/hr), and a 24 hr collection in standard tissue culture media containing 11 mM glucose and 5% fetal calf serum. Cell counts were determined as described and values are reported as µg growth hormone per million cells.

Figure 15A:
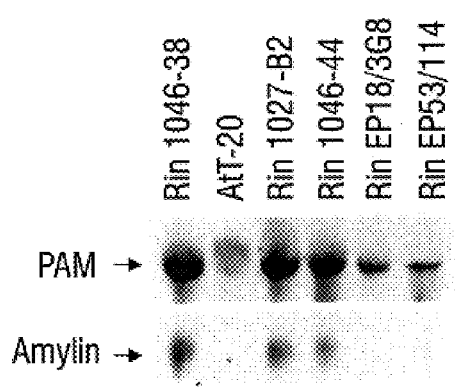

FIG. 15A: Coexpression of PAM and amylin in cell lines. Endogenous levels of expression of PAM and amylin in a series of cell lines was determined by Northern analysis. Cell lines examined were RIN 1046-38, AtT-20, RIN 1027-B2 and RIN 1046-44 (Phillipe et al., 1987), EP18/3G8 and EP53/114 (this study). Pam message runs at 3.5 to 4.0 kB (Stoffers et al., 1989) while amylin message is 0.9 kB (Leffert et al., 1989)

Figure 15B:
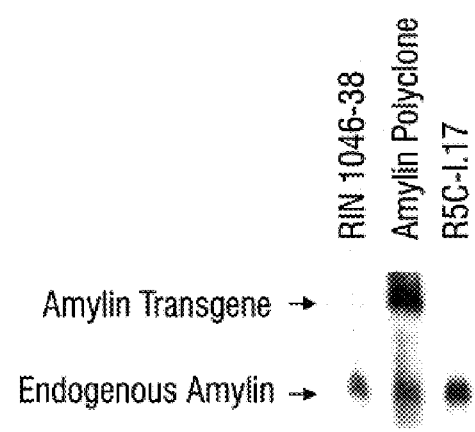

FIG. 15B: Northern analysis of RIN 1046-38 cells stably transfected with an amylin expression plasmid demonstrates high level expression of the transgene. Amylin is expressed as an amylin/IRES/NEO bicistronic message of 2.1 kB in the polyclone. Endogenous expression of amylin is present in the polyclone as well as RIN 1046-38 and R5C-I.17.

Figure 16:
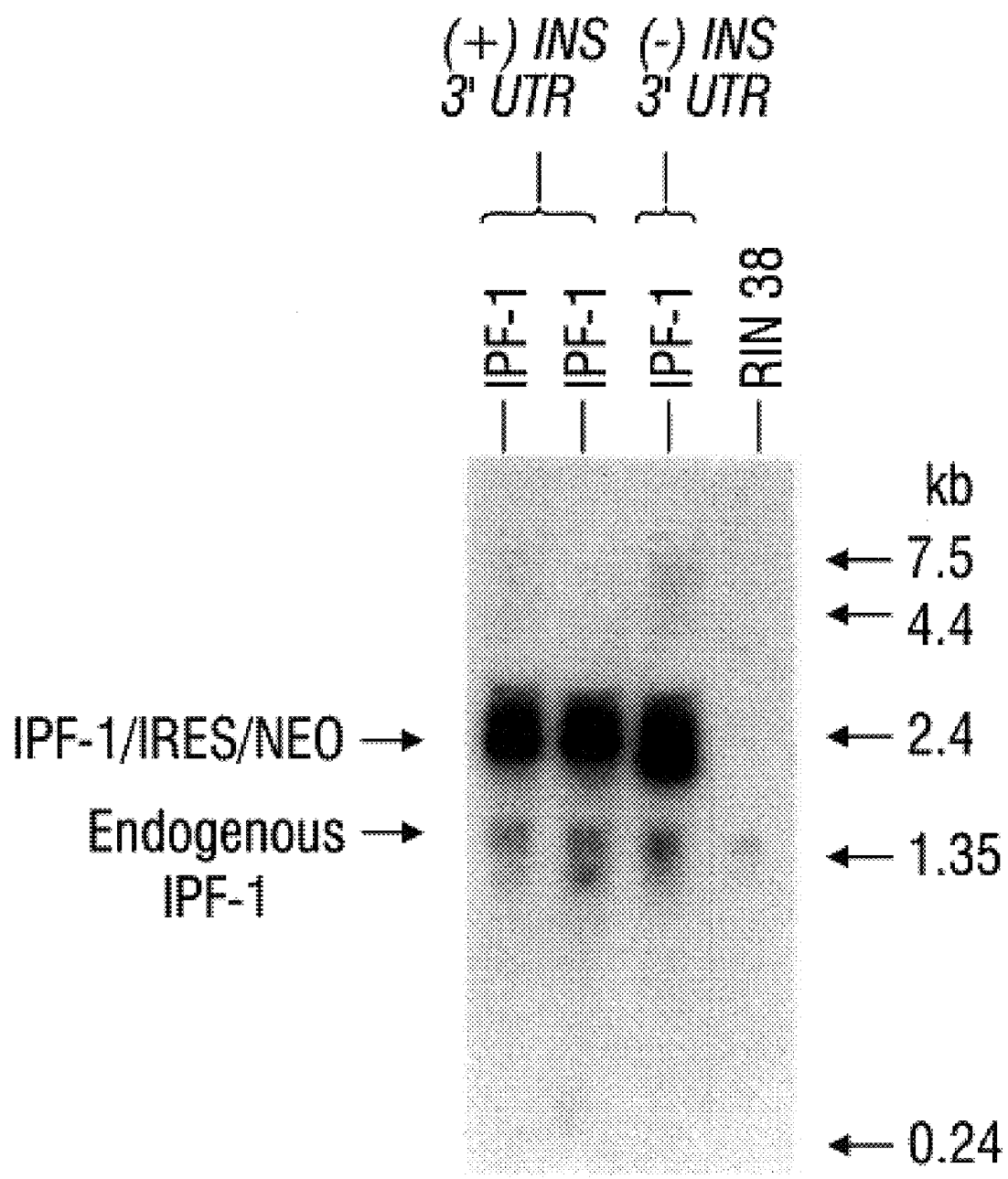

FIG. 16: Insulin Promoter Factor 1 (IPF-1) transgene expression in RIN cells. Levels of stably-transfected IPF-1 mRNA expressed in RIN 38 polyclones were determined by Northern blot analysis. All lanes contained 10 µg of total cellular RNA. The lane labelled RIN 38 contains RNA from untransfected cells. (+) INS 3'UTR indicates that the 3' untranslated sequence from the rat insulin 1 gene was attached immediately downstream of the IPF-1 cDNA to produce pCMV8/IPF-1(-Bg)/Ins3'/IRES/NEO.

IV. DETAILED DESCRIPTION OF THE PREFERRED EMBODIMENTS

Secretory cells, especially neuroendocrine cells, have several endogenous functions that make them uniquely suited for production of a wide range of proteins, including secreted peptide hormones. These specialized functions include the regulated secretory pathway. The regulated secretory pathway embodies the secretory granules of neuroendocrine cells which serve as the site of maturation and storage of a large class of peptide hormones with profound biological functions. Proper biological function of the peptides is due both to their secretion in a regulated and titratable manner as well as a complex set of post-translational modifications resulting in the final biologically active product. As a result, these cells can be used in vitro to produce large amounts of proteins, in vivo to supply therapeutic proteins, or in vivo to immunize hosts, for example, in the production of monoclonal antibodies.

The present invention is designed to take advantage of this secretory machinery for the purpose of producing heterologous proteins. A variety of different modifications may be made to increase the efficiency of the cell, but the primary modification is the blocking of production of an endogenous protein in the host cell. This will, in essence, "make room" for the heterologous protein and, hence, avoid competition between the endogenous and heterologous proteins during synthesis. The components for such a system, and methods of producing proteins therewith, are set forth in detail below.

A. Host Cells

Engineering of secretory cells to synthesize proteins for either in vitro large scale production, or for in vivo cell-based delivery, will advantageously make use of many attributes of these cells. Regulated secretory cells present a natural bioreactor containing specialized enzymes involved in the processing and maturation of secreted proteins. These processing enzymes include endoproteases (Steiner et al., 1992) and carboxypeptidases (Fricker, 1988) for the cleavage of prohormones to hormones and PAM, an enzyme catalyzing the amidation of a number of peptide hormones (Eipper et al., 1992a). Similarly, maturation and folding of peptide hormones is performed in a controlled, stepwise manner with defined parameters including pH, calcium and redox states.

Complete processing requires sufficient levels of the processing enzymes as well as sufficient retention of the maturing peptides. In this way, physiological signals leading to the release of the contents of the secretory granules ensures release of fully processed, active proteins. This is important for both maximum production for in vitro purposes and for the possible use of cells for in vivo purposes.

All cells secrete proteins through a constitutive, non-regulated secretory pathway. A subset of cells are able to secrete proteins through a specialized regulated secretory pathway. Proteins destined for secretion by either mechanism are targeted to the endoplasmic reticulum and pass through the golgi apparatus. Constitutively secreted proteins pass directly from the golgi to the plasma membrane in vesicles, fusing and releasing the contents constitutively without the need for external stimuli. In cells with a regulated pathway, proteins leave the golgi and concentrate in storage vesicles or secretory granules. Release of the proteins from secretory granules is regulated, requiring an external stimuli. This external stimuli, defined as a secretagogue, can vary depending on cell type, optimal concentration of secretagogue, and dynamics of secretion. Proteins can be stored in secretory granules in their final processed form for long periods of time. In this way a large intracellular pool of mature secretory product exists which can be released quickly upon secretogogue stimulation.

A cell specialized for secreting proteins via a regulated pathway can also secrete proteins via the constitutive secretory pathway. Many cell types secrete proteins by the constitutive pathway with little or no secretion through a regulated pathway. As used herein, "secretory cell" defines cells specialized for regulated secretion, and excludes cells that are not specialized for regulated secretion. The regulated secretory pathway is found in secretory cell types such as endocrine, exocrine, neuronal, some gastrointestinal tract cells and other cells of the diffuse endocrine system.

(i) Glucose Responsive Cells

For delivery of some peptide hormones or factors, it may be desirable to cause the polypeptide to be released from cells in response to changes in the circulating glucose concentration. The most obvious example of a secretory cell type that is regulated in this fashion is the β-cell of the pancreatic islets of Langerhans, which releases insulin in response to changes in the blood glucose concentration. Engineering of primary β-cells for production of products other than insulin is not practical. Instead, a preferred vehicle may be one of the several cell lines derived from islet β-cells that have emerged over the past two decades. While early lines were derived from radiation- or virus-induced tumors (Gazdar et al., 1980, Santerre et al., 1981), more recent work has centered on the application of transgenic technology (Efrat et al., 1988, Miyazaki et al., 1990). A general approach taken with the latter technique is to express an oncogene, most often SV40 T-antigen, under control of the insulin promoter in transgenic animals, thereby generating β-cell tumors that can be used for propagating insulinoma cell lines (Efrat et al., 1988, Miyazaki et al., 1990). While insulinoma lines provide an advantage in that they can be grown in essentially unlimited quantity at relatively low cost, most exhibit differences in their glucose-stimulated insulin secretory response relative to normal islets. These differences can be quite profound, such as in the case of RINm5F cells, which were derived from a radiation-induced insulinoma and which in their current form are completely lacking in any acute glucose-stimulated insulin secretion response (Halban et al., 1983, Shimuzu et al., 1988). RIN 1046-38 cells are also derived from a radiation-induced insulinoma but can be shown to be glucose responsive when studied at low passage numbers (Clark et al., 1990). This response is maximal at subphysiological glucose concentrations and is lost entirely when these cells are cultured for more than 40 passages (Clark et al., 1990). GLUT-2 and glucokinase are expressed in low passage RIN 1046-38 cells but are gradually diminished with time in culture in synchrony with the loss of glucose-stimulated insulin release (Ferber et al., 1994). Restoration of GLUT-2 and glucokinase expression in RIN 1046-38 cells by stable transfection restores glucose-stimulated insulin secretion (Ferber et al., 1994), and the use of these genes as a general tool for engineering of glucose sensing has been described in a previously issued patent (Newgard, U.S. Pat. No. 5,427,940). RIN 1046-38 cells transfected with the GLUT-2 gene alone are maximally glucose responsive at low concentrations of the sugar (approximately 50 $\mu$M), but the threshold for response can be shifted by preincubating the cells with 2-deoxyglucose, which when converted to 2-deoxyglucose-6-phosphate inside the cell serves as an inhibitor of low $K_m$ hexokinase, but not glucose activity (Ferber et al., 1994).

Recently, Asafari et al. have reported on the isolation of a new insulinoma cell line called INS-1 that retains many of the characteristics of the differentiated β-cell, most notably a relatively high insulin content and a glucose-stimulated insulin secretion response that occurs over the physiological range (Asfari et al., 1992). This line was isolated by propagating cells freshly dispersed from an X-ray induced insulinoma tumor in media containing 2-mercaptoethanol. Consistent with the finding of physiological glucose responsiveness, a recent report indicates that INS-1 cells express GLUT-2 and glucokinase as their predominant glucose transporter and glucose phosphorylating enzyme, respectively (Marie et al., 1993). INS-1 cells grow very slowly and require 2-mercaptoethanol. It remains to be determined whether glucose responsiveness and expression of GLUT-2 and glucokinase are retained with prolonged culturing of these cells.

Cell lines derived by transgenic expression of T-antigen in β-cells (generally termed β TC cells) also exhibit variable phenotypes (Efrat et al., 1988, Miyazaki et al., 1990, Whitesell et al., 1991 and Efrat et al., 1993). Some lines have little glucose-stimulated insulin release or exhibit maximal responses at subphysiological glucose concentrations (Efrat et al., 1988, Miyazaki et al., 1990, Whitesell et al., 1991), while others respond to glucose concentrations over the physiological range (Miyazaki et al., 1990 and Efrat et al., 1993). It appears that the near-normal responsiveness of the latter cell lines is not permanent, since further time in culture results in a shift in glucose dose response such that the cells secrete insulin at subphysiological glucose concentrations (Efrat et al., 1993). In some cases, these changes have been correlated with changes in the expression of glucose transporters and glucose-phosphorylating enzymes. Miyazaki et al. isolated two classes of clones from transgenic animals expressing an insulin promoter/T-antigen construct. Glucose-unresponsive lines such as MIN-7 were found to express GLUT-1 rather than GLUT-2 as their major glucose transporter isoformn, while MIN-6 cells were found to express GLUT-2 and to exhibit normal glucose-stimulated insulin secretion (Miyazaki et al., 1990). More recently, Efrat and coworkers demonstrated that their cell line bTC-6, which exhibits a glucose-stimulated insulin secretion response that resembles that of the islet in magnitude and concentration dependence, expressed GLUT-2 and contained a glucokinase:hexokinase activity ratio similar to that of the normal islet (Efrat et al., 1993). With time in culture, glucose-stimnulated insulin release became maximal at low, subphysiological glucose concentrations. GLUT-2 expression did not change with time in culture, and glucokinase activity actually increased slightly, but the major change was a large (approximately 6-fold) increase in hexokinase expression (Efrat et al., 1993). Furthermore, overexpression of hexokinase I, but not GLUT-1, in well-differentiated MIN-6 cells results in both increased glucose metabolism and insulin release at subphysiological glucose concentrations. Similar results have been obtained upon overexpression of hexokinase I in normal rat islets (Becker et al., 1994b). These results are all consistent with the observations of Ferber, et al. described above in showing that a high hexokinase:glucokinase ratio will cause insulin-secreting cells to respond to glucose concentrations less than those required to stimulate the normal β-cell.

(ii) Non-glucose Responsive Cells

An alternative to insulinoma cell lines are non-islet cell lines of neuroendocrine origin that are engineered for insulin expression. The foremost example of this is the AtT-20 cell, which is derived from ACTH secreting cells of the anterior pituitary. A decade ago, Moore et al. demonstrated that stable transfection of AtT-20 cells with a construct in which a viral promoter is used to direct expression of the human proinsulin cDNA resulted in cell lines that secreted the correctly processed and mature insulin polypeptide (Moore et al., 1983). Insulin secretion from such lines (generally termed AtT-20ins) can be stimulated by agents such as forskolin or dibutyryl cAMP, with the major secreted product in the form of mature insulin. This suggests that these cells contain a regulated secretory pathway that is similar to that operative in the islet β-cell (Moore et al., 1983, Gross et al., 1989). More recently, it has become clear that the endopeptidases that process proinsulin to insulin in the islet β-cell, termed PC2 and PC3, are also expressed in AtT-20ins cells (Smeekens et al., 1990, Hakes et al., 1991). AtT-20ins cells do not respond to glucose as a secretagogue (Hughes et al., 1991). Interestingly, AtT-20 cells express the glucokinase gene (Hughes et al., 1991, Liang et al., 1991) and at least in some lines, low levels of glucokinase activity (Hughes et al., 1991 and 1992, Quaade et al., 1991), but are completely lacking in GLUT-2 expression (Hughes et al., 1991 and 1992). Stable transfection of these cells with GLUT-2, but not the related transporter GLUT-1, confers glucose-stimulated insulin secretion, albeit with maximal responsiveness at subphysiological glucose levels, probably because of a non-optimal hexokinase:glucokinase ratio (Hughes et al., 1992, 1993).

The studies with AtT-20ins cells are important because they demonstrate that neuroendocrine cell lines that normally lack glucose-stimulated peptide release may be engineered for this function. Other cell lines that are characterized as neuroendocrine, but lacking in endogenous glucose response include PC12, a neuronal cell line (ATCC CRL 1721) and GH3, an anterior pituitary cell line that secretes growth hormone (ATCC CCL82.1). It is not possible to determine whether such cell lines will gain glucose responsiveness by engineering similar to that described for the AtT-20ins cell system without performing the experiments. However, these lines do exhibit other properties important for this invention such as a regulated secretory pathway, expression of endopeptidases required for processing of prohormones to their mature hormone products, and post-translational modification enzymes. In sum, all neuroendocrine cell lines are useful for the essential aspect of this invention, which is the production of heterologous products in a cell line in which the natural product (insulin, growth hormone, ACTH, etc.) has been eliminated. Some or all of these lines will also be useful for glucose-regulated product delivery, using the methods described in U.S. Pat. No. 5,427,940 to generate such responsiveness.

(iii) Methods for Blocking Endogenous Protein Production

Blocking expression of an endogenous gene product is an important modification of host cells according to the present invention. The targeted endogenous gene encodes a protein normally secreted by the host cell. Blocking expression of this endogenous gene product, while engineering high level expression of genes of interest, represents a unique way of designing cells for protein production.

Cells generated by this two-step process express heterologous proteins, including a variety of natural or engineered proteins (fusions, chimeras, protein fragments, etc.). Cell lines developed in this way are uniquely suited for in vivo cell-based delivery or in vitro large-scale production of defined peptide hormones with little or no contaminating or unwanted endogenous protein production.

Four basic approaches are contemplated for blocking of expression of an endogenous gene in host cells. First, constructs are designed to homologously recombine into particular endogenous gene loci, rendering the endogenous gene nonfunctional. Second, constructs are designed to randomly integrate throughout the genome, resulting in loss of expression of the endogenous gene. Third, constructs are designed to introduce nucleic acids complementary to a target endogenous gene. Expression of RNAs corresponding to these complementary nucleic acids will interfere with the transcription and/or translation of the target sequences. And fourth, constructs are designed to introduce nucleic acids encoding ribozymes—RNA-cleaving enzymes—that will specifically cleave a target mRNA corresponding to the endogenous gene.

Antisense. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucdeotide may provide more convenient restriction sites for the remaining portion of the construct and, therefore, would be used for the rest of the sequence.

Ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al,, 1990; Sioud et al., 1992). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Homologous Recombination. Another approach for blocking of endogenous protein production involves the use of homologous recombination. Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, a target gene is selected within the host cell. Sequences homologous to the target gene are then included in a genetic construct, along with some mutation that will render the target gene inactive (stop codon, interruption, etc.). The homologous sequences flanking the inactivating mutation are said to "flank" the mutation. Flanking, in this context, simply means that target homologous sequences are located both upstream (5') and downstream (3') of the mutation. These sequences should correspond to some sequences upstream and downstream of the target gene. The construct is then introduced into the cell, thus permitting recombination between the cellular sequences and the construct.

As a practical matter, the genetic construct will normally act as far more than a vehicle to interrupt the gene. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, a heterologous gene that is to be expressed in the cell also may advantageously be included within the construct. The arrangement might be as follows:

vector●5'-flanking sequence●heterologous gene●selectable marker gene●flanking sequence-3'●vector . . . Thus, using this kind of construct, it is possible, in a single recombinatorial event, to (i) "knock out" an endogenous gene, (ii) provide a selectable marker for identifying such an event and (iii) introduce a heterologous gene for expression.

Another refinement of the homologous recombination approach involves the use of a "negative" selectable marker. This marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired "knock out" phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

In a particular aspect of this embodiment, the negative selectable maker is GLUT-2. It is also contemplated that GLUT-5 would function in a similar manner to GLUT-2. Therefore, the selection protocols described are intended to refer to the use of both GLUT-2 and GLUT-5.

In a first embodiment, a target gene within a GLUT-2⁻ host cell is selected as the location into which a selected gene is to be transferred. Sequences homologous to the target gene are included in the expression vector, and the selected gene is inserted into the vector such that target gene homologous sequences are interrupted by the selected gene or, put another way, such the target gene homologous sequences "flank" the selected gene. In preferred embodiments, a drug selectable marker gene also is inserted into the target gene homologous sequences. Given this possibility, it should be apparent that the term "flank" is used broadly herein, namely, as describing target homologous sequences that are both upstream (5') and downstream (3') of the selected gene and/or the drug selectable marker gene. In effect, the flanking sequences need not directly abut the genes they "flank."

The construct for use in this embodiment is further characterized as having a functional GLUT-2 gene attached thereto. Thus, one possible arrangement of sequences would be:

5'-GLUT-2●flanking target sequences●selected gene●drug- selectable marker gene●flanking target sequences-3●. . .

Of course, the GLUT-2 could come at the 3'-end of the construct and the selected gene and drug-selectable marker genes could exchange positions.

Application of a drug to such cells will permit isolation of recombinants, but further application of Streptozotocin (glucopyranose, 2-deoxy-2-[3-methyl-e-nitrosourido-D]; STZ) to such cells will result in killing of non-homologous recombinants because the incorporated GLUT-2 gene will produce GLUT-2 transporter, rendering the cells susceptible to STZ treatment (the original cell was GLUT-2⁻).

On the other hand, site-specific recombination, relying on the homology between the vector and the target gene, will result in incorporation of the selected gene and the drug selectable marker gene only; GLUT-2 sequences will not be introduced in the homologous recombination event because they lie outside the flanking sequences. These cells will be drug resistant and but not acquire the GLUT-2 sequences and, thus, remain insensitive to STZ. This double-selection procedure (drug$^{res}$/STZ$^{res}$) should yield recombinants that lack the target gene and express the selected gene. Further screens for these phenotypes, either functional or immunologic, may be applied.

A modification of this procedure is one where no selected gene is included, i.e., only the selectable marker is inserted into the target gene homologous sequences. Use of this kind of construct will result in the "knock-out" of the target gene only. Again, proper recombinants are screened by drug resistance and STZ resistance (the original cell was GLUT-2⁻).

Random Integration. Though lacking the specificity of homologous recombination, there may be situations where random integration will be used as a method of knocking out a particular endogenous gene. Unlike homologous recombination, the recombinatorial event here is completely random, i.e., not reliant upon base-pairing of complementary nucleic acid sequences. Random integration is like homologous recombination, however, in that a gene construct, often containing a heterologous gene and a selectable marker, integrates into the target cell genomic DNA via strand breakage and reformation.

Because of the lack of sequence specificity, the chances of any given recombinant integrating into the target gene are greatly reduced. Also possible is integration into a second loci, resulting in the loss of expression of the gene of interest. This second locus could encode a transcription factor needed for expression of the first gene, a locus control region needed for the expression of the first gene, etc. As a result, it may be necessary to "brute force" the selection process. In other words, it may be necessary to screen hundreds of thousands of drug-resistant recombinants before a desired mutant is found. Screening can be facilitated, for example, by examining recombinants for expression of the target gene using immunologic or even functional tests; expression of the target gene indicate recombination elsewhere and, thus, lack of suitability.

(iv) Methods for Increasing Production of Recombinant Peptides from Secretory Cells The present invention also contemplates augmenting or increasing the capabilities of cells to produce biologically active polypeptides. This can be accomplished, in some instances, by overexpressing the proteins involved in protein processing, such as the endoproteases PC2 and PC3 (Steiner et al., 1992) or the peptide amidating enzyme, PAM (Eipper et al., 1992a) in the case of amidated peptide hormones.

Expression of proteins involved in maintaining the specialized phenotype of host cells, especially their secretory capacity, is important. Engineering the overexpression of a cell type-specific transcription factor such as the Insulin Promoter Factor 1 (IPF1) found in pancreatic β-cells (Ohlsson et al., 1993) could increase or stabilize the capabilities of engineered neuroendocrine cells. Insulin promoter factor 1 (IPF-1; also referred to as STF-1, IDX-1, PDX-1 and βTF-1) is a homeodomain-containing transcription factor proposed to play an important role in both pancreatic development and insulin gene expression in mature β cells (Ohlsson et al., 1993, Leonard et al., 1993, Miller et al., 1994, Kruse et al., 1993). In embryos, IPF-1 is expressed prior to islet cell hormone gene expression and is restricted to positions within the primitive foregut where the pancreas will later form. Indeed, mice in which the IPF-1 gene is disrupted by targeted knockout do not form a pancreas (Jonsson et al., 1994). Later in pancreatic development, as the different cell types of the pancreas start to emerge, IPF-1 expression becomes restricted predominantly to β cells. IPF-1 binds to TAAT consensus motifs contained within the FLAT E and P1 elements of the insulin enhancer/promoter, whereupon, it interacts with other transcription factors to activate insulin gene transcription (Peers et al., 1994).

Stable overexpression of IPF-1 in neuroendocrine β cell lines will serve two purposes. First, it will increase transgene expression under the control of the insulin enhancer/promoter. Second, because IPF-1 appears to be critically involved in β cell maturation, stable overexpression of IPF-1 in β cell lines should cause these mostly dedifferentiated β-cells to regain the more differentiated function of a normal animal β cell. If so, then these redifferentiated β cell lines could potentially function as a more effective neuroendocrine cell type for cell-based delivery of fully processed, bioactive peptide hormones.

Also, further engineering of cells to generate a more physiologically-relevant regulated secretory response is claimed. Examples would include engineering the ratios of glucokinase to hexokinase in rat insulinoma cells that also overexpress the Type II glucose transporter (GLUT-2) such that a physiologically-relevant glucose-stimulated secretion of peptide hormones is achieved. Other examples include engineering overexpression of other signalling proteins known to play a role in the regulated secretory response of neuroendocrine cells. These include cell surface proteins such as the β-cell-specific inwardly rectifying potassium channel (BIR; Inagaki et al., 1995), involved in release of the secretory granule contents upon glucose stimulation, the sulfonylurea receptor (SUR), and ATP sensitive channel. Other cell surface signalling receptors which help potentiate the glucose-stimulated degranulation of β-cells including the glucagon-like peptide I receptor (Thorens, 1992) and the glucose-dependent insulinotropic polypeptide receptor (also known as gastric inhibitory peptide receptor) (Usdin, 1993) can be engineered into neuroendocrine cells. These β-cell-specific signaling receptors, as well as GLUT-2 and glucokinase, are involved in secretory granule release in response to glucose. In this way, glucose stimulated release of any heterologous peptide targeted to the secretory granule can be engineered. Alternatively, other cell surface signaling proteins involved in non-glucose-stimulated release of secretory granule contents can be engineered into neuroendocrine cells. Examples would include releasing factor receptors such as Growth Hormone Releasing Factor Receptor (Lin et al., 1992) and Somatostatin or Growth Hormone Releasing Hormone Receptor (Mayo, 1992).

One potential target for genetic engineering to improve cell characteristics for protein production is hexokinase I. It now has been determined that intefering with hexokinase I function reduces the growth rate of cells. The following is a discussion of engineering of hexokinases according to the present invention.

Mitochondrial Binding. Low $K_m$ hexokinases are distinguished from glucokinase in that they are allosterically regulated by glucose-6-phosphate and by binding to mitochondria (Wilson, 1968; 1973; 1985; 1995). Micromolar concentrations of glucose-6-phosphate inhibit the activities of hexokinases I, II, and III, but appreciable inhibition of glucokinase requires glucose-6-phosphate concentrations in excess of 10 mM. Binding of hexokinases I and II to mitochondria alters their kinetic properties (Wilson, 1968; 1985; 1995), while glucokinase does not appear to be capable of binding to mitochondria at all (Becker et al. 1996).

When bound to mitochondria, hexokinase I undergoes an increase in affinity (a decrease in $K_m$) for its substrate ATP (Wilson, 1985). In addition, the enzyme becomes far less inhibitable by glucose-6-phosphate, as indicated by a several-fold increase in $K_i$ for this ligand (Wilson, 1985). Studies with hexokinase I have revealed the existence of two types of mitochondrial binding sites (Kabeer and Wilson, 1994). Glucose-6-phosphate causes displacement of a proportion of mitochondrially-bound hexokinase from one type of site. The enzyme that remains bound to mitochondria after glucose-6-phosphate treatment is considered to occupy the second site, from which it can be removed by treatment with 0.5 M KSCN.

It has been known for some time that limited digestion of hexokinase I with chymotrypsin yields an enzyme fragment that retains catalytic activity but that loses its capacity for mitochondrial binding, and that enzyme treated in this manner is lacking in a portion of its N-terminal domain (Polakis and Wilson, 1985). The N-terminal sequences of both hexokinases I and II are relatively hydrophobic, and it has been shown that the hydrophobic N-terminus of hexokinase I is capable of insertion into the lipid bilayer of the mitochondrial membrane (Xie and Wilson, 1988).

Subsequently, Gelb et al., (1992) demonstrated that a chimeric protein consisting of the N-terminal 15 amino acids of hexokinase I fused to chloramphenicol acetyltransferase was capable of binding to rat liver mitochondria, and that this binding was competitive with authentic hexokinase I (Gelb et al. 1992). Although Gelb et al. (1992) have suggested that the first 15 amino acids of hexokinase are sufficient to target such a chimeric protein to mitochondria, these studies were not designed to attempt to alter metabolic regulation in target cell lines. Thus, the elements required to effect displacement of endogenous hexokinase from its mitochondrial binding site were not unequivocally identified in the study of Gelb and co-authors as discussed below.

While the results of Gelb et al. (1992) argue for the importance of this small N-terminal segment in targeting of hexokinase to mitochondria, others have suggested that other regions of the molecule may also be important in stabilizing the interaction (Polakis and Wilson, 1985; Felgner and Wilson, 1977; Smith and Wilson, 1991). This is based on studies showing that hexokinase I binding to mitochondria is stabilized by $Mg^{2+}$, an effect likely reflecting electrostatic interactions between the enzyme and the outer mitochondrial membrane (i.e., not involving the N-terminal 15 amino acids that are intercalated into the membrane). Therefore, the mitochondrial binding regions of HK have not been clearly identified to date, and there is even less information available on the issue of HK displacement.

At least part of hexokinase binding to mitochondria is via interactions with members of a family of proteins known as voltage-dependent anion channels (VDAC) or porins (Fiek et al., 1982; Linden et al., 1982). These porins form a channel through which metabolites such as ATP and various anions traverse the outer mitochondrial membrane. Binding of hexokinases to porin thus may ensure a supply of intramitochondrially-generated ATP as substrate.

Constructs of the present invention may comprise the N-terminal 15 amino acids of a hexokinase enzyme, preferably hexokinase I or II, since this segment should be easily expressed in cells and retained as a stable peptide. Constructs comprising the entire N-terminal domain of either hexokinase I or hexokinase II, or the intact, full-length hexokinase I or II proteins that have been rendered inactive by site-directed mutagenesis of amino acids that are important for the enzyme's catalytic function are also contemplated. Constructs based upon hexokinase I will be particularly, or even exclusively, preferred in certain embodiments.

The reason for preferring the N-terminal domain construct is that this element seems to comprise a complete structural domain, based upon studies in which this domain can be expressed in bacteria and shown to bind glucose-6-phosphate (Wilson, 1994; Arora et al., 1993; White and Wilson, 1987; White and Wilson, 1990). This suggests that the intact N-terminal domain should fold and form a structure analogous to its structure in the full-length hexokinase I or II protein. As the present inventors contemplate that this structure mediates attachment of the intact hexokinase protein to mitochondria, the intact, correctly folded N-terminal domain is a preferred embodiment of this invention.

For embodiments involving the N-terminal domain, a segment comprising amino acids 1–455 is preferred because of a naturally occurring NcoI restriction enzyme site in the DNA sequence corresponding to amino acid 482. This NcoI site allows the fragment encoding the N-terminal domain to be easily isolated and subcloned, and also allows direct fusion of the N-terminal domain of hexokinase to the intact functional sequence of glucokinase via an NcoI site located at the AUG start codon of this gene.

Of course, it will be understood that peptides, polypeptides and protein domains of any intermediate length between about 15 amino acids and about 455 amino acids, and longer proteins, may be used in displacing endogenous hexokinase from the mitochondria. Accordingly, constructs comprising about 20, about 50, about 100, about 150, about 200, about 300 or about 400 amino acids in length may be used for these purposes. It is also contemplated that an intact hexokinase protein that is rendered catalytically inactive will interact with mitochondria in a manner identical to the active proteins. Expression of such a HK variant is therefore another method for inhibiting endogenous HK (Baijal and Wilson, 1992). Inactivated, hexokinase proteins include those that have been subjected to chemical mutagenesis and also those produced using molecular biological techniques and recombinant protein production.

The identification of appropriate polypeptide regions and/ or particular amino acid sites that may be targeted in order to inactivate hexokinase will be known to those of skill in the art. The crystal structure of certain hexokinase enzymes is available. Coupling the crystal structure information with a comparison of the primary sequence information for various distinct hexokinases will allow one to identify those regions and sites that are important for hexokinase activity, such as the binding sites for ATP, glucose and glucose-6-phosphate. This has been discussed in detail in various publications, such as Printz et al. (1993), incorporated herein by reference, which information can be used in connection with preparing mutants and variants for use herewith. Deletion of certain amino acids or peptide segments, as may be achieved by molecular biological manipulation, is another contemplated method for preparing inactive hexokinases.

The enzyme glycerol kinase is another protein thought to bind to mitochondria via porins or VDACs (Adams et al., 1991). Glycerol kinase catalyzes formation of glycerol phosphate from glycerol, using ATP as phosphate donor. Thus, expression of glycerol kinase in cell lines represents an alternative to expression of inactive hexokinase proteins or fragments thereof which is also contemplated for use in the displacement of endogenous low-$K_m$ hexokinases from their normal mitochondrial binding site.

A particularly powerful method of inhibiting hexokinase within a mammalian cell involves the displacement of hexokinase from the mitochondria and the concomitant provision of inactive glucokinase. This is advantageously achieved by providing to the cell a hexokinase-glucokinase chimera or fusion protein, in which the hexokinase portion is capable of binding to the mitochondria and yet does not exhibit hexokinase catalytic activity, and in which the glucokinase portion is catalytically active. Chemically-fused polypeptides are a possibility, but recombinant proteins are naturally most preferred for use in this manner. The identification of appropriate hexokinase fragments for use in such a chimera has been described herein above.

In terms of the glucokinase portions of these fusion proteins, any glucokinase-derived sequence that contains enough primary sequence information to confer glucokinase catalytic activity to the chimera will be useful in this context. However, it will often be preferred to use the entire glucokinase enzyme as this is more straightforward in terms of methodology. Again, one may look to the extensive information available in various published references in order to assist with the identification of appropriate glucokinase enzymes or fragments thereof.

At this point, a discussion of the kinetic properties of hexokinase and glucokinase is relevant. It will be understood that in providing a functional equivalent of a hexokinase or glucokinase enzyme, one would desire to provide a protein that has substantially the same kinetic parameters as the native enzyme. Equally, in providing a hexokinase mutant that is devoid of catalytic activity, one would provide an enzyme that is either completely inactivated or whose kinetic parameters have been shifted so that it is, in fact, distinct from the native enzyme.

Table 0, below, sets forth a comparison of glucokinase with hexokinases I–III. This information may be used in order to determine whether any particular variant is "equivalent", and also, to confirm that any inactive mutants have indeed been properly disabled.

TABLE 0

A Comparison of Glucokinase With Hexokinases

|  | GK | HK 1-111 |
|---|---|---|
| Km glucose | 5–12 mM | 0.02–0.13 mM |
| Km ATP | ~0.5 mM | 0.2–0.5 mM |
| Ki G-6-P | 60 mM | 0.2–0.9 mM |
| Molecular weight | 52 kd | ~100 kd |
| Substrate preference |  |  |
| Glucose | 1 | 1 |
| Mannose | 0.8 | 1–1.2 |
| 2-Deoxyglucose | 0.4 | 1–1.4 |
| Fructose | 0.2 | 1.1–1.3 |

The activity of glucose as a substrate is taken as 1. The other numbers are expressed in relation to the activity of glucose as a substrate.

Trehalose-6-Phosphate Metabolism. In Baker's yeast, glucose phosphorylation is also catalyzed by a family of hexokinases that are related in sequence and function to the mammalian hexokinase gene family. Yeast cells, however, contain other genes involved in carbohydrate metabolism for which there are no mammalian counterparts. The trehalose-6-phosphate synthase/trehalose-6-phosphate phosphatase complex is an example of such an activity.

The trehalose-6-phosphate synthase/phosphatase complex catalyzes the formation of trehalose, a disaccharide of two glucose molecules (α-D-glucopyranosyl (1-1) α-D-glucopyranoside) by first forming trehalose-6-phosphate by condensation of two molecules of glucose-6-phosphate and then using its phosphatase activity to remove the phosphate groups to generate free trehalose (Bell et al., 1992). Trehalose is thought to represent a form of storage polysaccharide in yeast, bacteria and other lower organisms, but neither the trehalose-6-phosphate synthase enzyme complex nor its products trehalose-6-phosphate or free trehalose are known to be present in mammalian cells.

Blazquez et al. have demonstrated that trehalose-6-phosphate can inhibit the activity of hexokinases from a variety of different organisms, including rat brain, which expresses predominantly hexokinase I (Blasquez et al., 1993). This has led to the suggestion that trehalose-6-phosphate may be an important regulator of glycolytic flux in yeast cells. Consistent with this notion, the yeast gene known as cif-1 was originally cloned from yeast that are unable to grow in glucose (Blasquez et al., 1993) and subsequently shown to be identical to the smallest subunit (56 kD) of the trehalose phosphate synthase/trehalose-6-phosphate phosphatase complex (Bell et al., 1992). Cells lacking in the CIF-1 gene product exhibit rapid depletion of ATP, presumably because they are unable to produce trehalose-6-phosphate that normally serves to moderate yeast hexokinase activity. It is believed that the 56 kDa CIF-1 gene product encodes the trehalose phosphate synthase activity (Bell et al., 1992).

One of the three general methods described in this application for inhibiting low $K_m$ hexokinase activity in mammalian cells is to express an enzyme, such as yeast trehalose-6-phosphate synthase, that will allow trehalose-6-phosphate to accumulate. This will have two effects. First, the accumulated trehalose-6-phosphate will serve to allosterically inhibit endogenous low $K_m$ hexokinase activity. Second, where trehalose-phosphate synthase is used, this enzyme will divert glucose-6-phosphate into trehalose-6-phosphate at low, non-stimulatory glucose concentrations where low Km hexokinases but not glucokinases are active, thereby "short-circuiting" metabolic signalling for insulin secretion, which is thought to require ATP produced via further glucose metabolism (Newgard and McGarry, 1995).

A currently preferred gene for use in these aspects is the *S. cerevisiae* gene encoding trehalose-6-phosphate synthase (TPS1). Genes from several other organisms encoding treholose-6-phosphate synthase have been isolated and the amino acid sequences deduced. These include *E. coli* (Accession # X69160), *S. pombe* (# Z29971), *Mycobactelium laprae* (# U15187) and *Aspergillus niger* (# U07184). It is contemplated that any of the foregoing or other biological functional equivalents thereof may be used in the context to the present invention.

Hexokinase Inhibition at Nucleic Acid Level. Several different ribozyme motifs have been described with RNA cleavage activity (reviewed in Symons, 1992). Examples that would be expected to function equivalently for the down regulation of low $K_m$ hexokinases include sequences from the Group I self splicing introns including Tobacco Ringspot Virus (Prody et al., 1986), Advocado Sunblotch Viroid (Palukaitis et al., 1979 and Symons, 1981), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994), hairpin ribozyme structures (Berzal-Herranz et al., 1992 and Chowrira et al., 1993) and Hepatitis Delta virus based ribozymes (Perrotta and Been, 1990). The general design and optimization of ribozyme directed RNA cleavage activity has been discussed in detail (Haseloff and Gerlach, 1988, Symons, 1992, Chowrira et al., 1994, and Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Perriman et al., 1992 and Thompson et al., 1995). The frequency of this dinucleotide occurring in any given RNA is statistically 3 out of 16. Therefore, for a given target messenger RNA of 1000 bases, 187 dinucleotide cleavage sites are statistically possible. The message for low $K_m$ hexokinases targeted here are greater than 3500 bases long, with greater than 500 possible cleavage sites.

The large number of possible cleavage sites in the low $K_m$ hexokinases coupled with the growing number of sequences with demonstrated catalytic RNA cleavage activity indicates that a large number of ribozymes that have the potential to downregulate the low $K_m$ hexokinases are available. Designing and testing ribozymes for efficient cleavage of a target RNA is a process well known to those skilled in the art. Examples of scientific methods for designing and testing ribozymes are described by Chowrira et aL, (1994) and Lieber and Strauss (1995), each incorporated by reference. The identification of operative and preferred sequences for use in hexokinase-targeted ribozymes is simply a matter of preparing and testing a given sequence, and is a routinely practiced "screening" method known to those of skill in the art.

Combination of Inhibitory Methods. Any of the three general methods of HK inhibition described above (Mitochondrial HK displacement, trehalose-6-phosphate generation and anti-HK ribozymes) may be combined with one another and/or with other engineering methods. It is particularly contemplated that these methods could be used in combination with glucokinase overproduction. Glucokinase overproduction alone is even thought to be a useful method of inhibiting hexokinase, as set forth below.

Low $K_m$ hexokinases, including hexokinases I and II that are present at high levels in mammalian cell lines, are inhibited by glucose-6-phosphate. Thus, this invention also relates to methods for maintaining glucose-6-phosphate at high levels in cell lines. The preferred method for achieving consistently high levels of glucose-6-phosphate in cells is to overexpress glucokinase in such lines.

Expression of glucokinase is considered advantageous for two distinct reasons. First, as described in U.S. Pat. No. 5,427,940 expression of glucokinase is part of an advantageous method for engineering of glucose-stimulated insulin secretion in cell lines. Glucokinase expression is herein shown to have the added benefit of maintaining high levels of glucose-6-phosphate to keep low $K_m$ hexokinases in an inhibited state. This advantage would become particularly relevant at glucose concentrations in the physiological range (4–9 mM), because glucokinase is active at these levels. Also, while glucokinase is a member of the hexokinase gene family, it is not itself inhibited by glucose-6-phosphate.

Advantages of Hexokinase Inhibition in Mammalian Cells. The various aspects of this invention focus specifically on reducing the levels of low $K_m$ hexokinase activity in mammalian cells. A particular type of target cell is a neuroendocrine cell. There are at least two significant achievements accomplished by the hexokinase inhibition of the present invention, as set forth below.

In addition to the regulation of insulin secretion by glucose, the hexokinase gene family may also be important in the regulation of cell growth and proliferation. As described above, increases in low $K_m$ hexokinase activity usually correlate with the transformation of cells from a normal to cancerous phenotype. However, the correlation has not been proven to exist as a cause and effect relationship. In addition, increases in mitotic activity are not universally linked to induction of low $K_m$ hexokinases. The activity of these enzymes did not increase in preneoplastic mouse beta cell lines over-expressing simian virus 40 large T antigen (Tag) (Radvanyi et al., 1993); nor are they universally elevated in fully transformed mouse β cells (Efrat et al., 1993).

The reduction of hexokinase activity in a cell line by any suitable method, including any of the novel methods disclosed herein, is contemplated to be of use in inhibiting cell growth. Hexokinase I was discovered to be a regulator of cell growth during the inventors' studies in which a RIN cell line (86/X4) that contains a disrupted allele of the HKI gene was surprisingly found to grow about one-half as fast as clones containing the normal compliment of two HKI wild-type genes.

A relationship between low $K_m$ hexokinase activity and cellular growth rates has three important implications relative to the application of cell-based therapies. First, from the perspective of iterative genetic engineering, an untimely or unregulated decrease of hexokinase activity will potentially hinder the growth and selection of clones possessing desired genotypes and traits. A cell line that over-expresses hexokinase I from a regulatable promoter may provide the optimal genetic background for engineering of gene targets. For example, a RIN cell line could be developed that transgenically expresses hexokinase under the control of the tetracycline (Tet)-resistance operon regulatory system (Gossen and Bujard, 1992). This expression system allows powerful transcription of gene products and permits the ablation of gene expression in the presence of Tet and Tet derivatives. Efrat et al. (1995) have demonstrated the feasibility of using this expression system to regulate large Tag gene expression. The expression of Tag caused transformation and expansion of mouse beta cells. A decrease of Tag expression, by the in vitro or in vivo administration of Tet, led to an inhibition of cellular proliferation.

A RIN or neuroendocrine cell line that expresses HKI from a repressible promoter could be further engineered to express high levels of human insulin, glucokinase, and GLUT-2. In addition, such a cell line would be an ideal host for the ablation or down regulation of low $K_m$ hexokinases. Such engineering could be pursued without the hindering complication of slowed growth. Following a series of desired genetic manipulations, the growth of the cells and the glucose sensing ability could be modulated by down regulating hexokinase expression.

A second implication of low $K_m$ hexokinase as a regulator of cellular growth concerns the use of engineered cells for in vivo therapies. It is envisioned that cell-based delivery will be conducted by maintenance of the cells in vivo in a perm-selective device. It is contemplated that cells with reduced levels of low $K_m$ hexokinase activity will survive for longer periods of time in devices or capsules as a consequence of their reduced growth rates.

A third implication of low $K_m$ hexokinases as regulators of cellular growth involves the creation of novel β-cell lines. The over-expression of HKI by introduction of exogenous DNA into a primary beta cell could be an essential ingredient of the transformation process. NIH-3T3 cells, an immortalized cell line, showed increases in glycolysis and growth rates following transfection with low $K_m$ hexokinase (Fanciulli et al., 1994). In a preferred embodiment, hexokinase I would need to be under the control of a promoter that can be down regulated. Such transcriptional regulation would allow the subsequent modulation of growth and glucose sensing.

A second important reason for reducing hexokinase activity is that it will contribute to the development of engineered cells that exhibit glucose-regulatable protein secretion, the most important aspect of which is presently the physiologically regulated release of insulin. Insulin release from the β-cells of the islets of Langerhans in the pancreas is prominently regulated by the circulating glucose concentration. Glucose stimulates insulin release over the physiological range of glucose concentrations (approximately 4–9 mM), with the amount of insulin secreted being proportional to the rate of glucose metabolism (Newgard and McGarry, 1995).

Glucose phosphorylation appears to play an important role in regulating glucose metabolism and insulin responsiveness (Meglasson and Matschinsky, 1986). Thus, while islet extracts contain approximately equal amounts of high $K_m$ glucokinase and low $K_m$ hexokinase activities (Meglasson and Matchinsky, 1986; Hughes et al., 1992), the hexokinases appear to be inhibited in intact islets, presumably by glucose-6-phosphate, allowing the glucokinase activity to be predominant. Since glucokinase has a $K_m$ for glucose (approximately 6–8 mM) that is within the physiological range, it is ideally suited for regulating glycolytic flux and insulin release in proportion to the extracellular glucose concentration.

The concept of a regulatory role for glucokinase, which has been developed over several years (Meglasson and Matchinsky, 1986; Matshchinsky, 1990), is supported by recent genetic and molecular studies, in which reduced expression of glucokinase was shown to result in less robust glucose-stimulated insulin secretion (Froguel et al., 1993; Efrat et al., 1994). Islet β-cells are also equipped with a specialized glucose transporter, GLUT-2, which like glucokinase is the high $K_m$ member of its gene family.

One of the present inventors has shown that GLUT-2 and glucokinase work in tandem as the "glucose sensing apparatus" of the β-cell (U.S. Pat. No. 5,427,940; Newgard, 1990). U.S. Pat. No. 5,427,940, incorporated herein by reference, describes methods for conferring glucose sensing in neuroendocrine cells and cell lines by transfection of such cells with one or more genes selected from the insulin gene, the glucokinase gene and the GLUT-2 glucose transporter gene, so as to provide an engineered cell having all three of these genes.

The overexpression of low $K_m$ hexokinases is known to exert a dominant effect on the glucose concentration threshold for insulin secretion. Overexpression of a low $K_m$ hexokinase from yeast in islet β-cells of transgenic animals results in increased rates of low $K_m$ glucose metabolism and enhanced insulin release at subphysiological glucose concentrations (Epstein et al., 1992; Voss-McGowan et al., 1994). Similar changes were noted upon overexpression of hexokinase I in isolated rat islets (Becker et al., 1994a) or in aIll-differentiated insulinoma cell line called MIN-6 (Ishihara et al., 1994).

It has been shown that the neuroendocrine cell lines that are contemplated for use in engineering artificial β-cells generally have significantly higher low $K_m$ hexokinase activity than normal islet 3-cells (Hughes et al., 1992; Efrat et al., 1993; Hughes et al., 1993; Ferber et al., 1994; Knaack et al., 1994), and that glucose metabolism in such cells is highly active at low glucose concentrations. As the glucokinase:hexokinase activity ratio is a critical determinant of the glucose response threshold in insulin secreting neuroendocrine cells, and as an imbalance in favor of hexokinase can cause insulin secretion to occur at glucose concentrations that are below the physiological threshold, it is evident that the most preferred artificial β cells should be further engineered to reduce hexokinase activity. The application of the methods of the present invention to the development of improved insulin secreting cells thus represents a significant advance.

Inhibition Levels. As defined herein, the degree of inhibition of hexokinase that is preferred is that necessary to achieve a glucose responsive insulin secretion in the physiologic range of 1.0 to 20 mM glucose. It will be understood by those working in this field that the absolute level of inhibition is difficult to predict. Measurements of hexokinase and glucokinase in freshly isolated islets as well as cell lines varies dramatically. Ratios of HK to GK can vary from 2.8 (Burch et al., 1981) to 0.8 (Liang et al., 1990) to 0.5 (Hosokawa et al., 1995) in fresh islets all with "normal" glucose stimulated insulin secretion. Reports of incorporated herein by reference cell lines with "normal" secretion shows an HK to GK ratio of 0.6 (Efrat et al., 1993) in the range of the fresh islets. These discrepancies illustrate the difficulties in specifying absolute numbers of glucokinase and hexokinase activities, hence the preference for using glucose responsive insulin secretion ranges as a meaningful parameter in this characterizing the cells invention.

(v) Methods for Re-engineering Engineered Cells

In many situations, multiple rounds of iterative engineering will be undertaken in generating the final cell lines. The events that may be conducted as separate construction events include blocking expression of endogenous gene products by molecular methods (including targeting of both copies of the endogenous gene), introducing a heterologous gene, and further modification of the host cell to achieve high level expression. The particular difficulty in performing multiple steps like this is the need for distinct selectable markers. This is a limitation in that only a few selectable markers are available for use in mammalian cells and not all of these work sufficiently well for the purposes of this invention.

The present invention therefore contemplates the use of the Cre/Lox site-specific recombination system (Sauer, 1993, available through Gibco/BRL, Inc., Gaithersburg, Md.) to rescue specific genes out of a genome, most notably drug selection markers. It is claimed as a way of increasing the number of rounds of engineering. Briefly, the system involves the use of a bacterial nucleotide sequence knows as a LoxP site, which is recognized by the bacterial Cre protein. The Cre protein catalyzes a site-specific recombination event. This event is bidirectional, i.e., Cre will catalyze the insertion of sequences at a LoxP site or excise sequences that lie between two LoxP sites. Thus, if a construct containing a selectable marker also has LoxP sites flanking the selectable marker, introduction of the Cre protein, or a polynucleotide encoding the Cre protein, into the cell will catalyze the removal of the selectable marker. If successfully accomplished, this will make the selectable marker again available for use in further genetic engineering of the cell. This technology is explained in detail in U.S. Pat. No. 4,959,317, which is hereby incorporated by reference in its entirety.

It also is contemplated that a series of different markers may be employed in some situations. These markers are discussed in greater detail, below.

B. Proteins

A variety of different proteins can be expressed according to the present invention. Proteins can be grouped generally into two categories—secreted and non-secreted—discussions of each are detailed below. There are some general properties of proteins that are worthy of discussion at this juncture.

First, it is contemplated that many proteins will not have a single sequence but, rather, will exists in many forms. These forms may represent allelic variation or, rather, mutant forms of a given protein. Second, it is contemplated that various proteins may be expressed advantageously as "fusion" proteins. Fusions are generated by linking together the coding regions for two proteins, or parts of two proteins. This generates a new, single coding region that gives rise to the fusion protein. Fusions may be useful in producing secreted forms of proteins that are not normally secreted or producing molecules that are immunologically tagged. Tagged proteins may be more easily purified or monitored using antibodies to the tag. A third variation contemplated by the present invention involves the expression of protein fragments. It may not be necessary to express an entire protein and, in some cases, it may be desirable to express a particular functional domain, for example, where the protein fragment remains functional but is more stable, or less antigenic, or both.

(i) Secreted Proteins

Expression of several proteins that are normally secreted can be engineered into neuroendocrine cells. The cDNA's encoding a number of useful human proteins are available. Examples would include soluble CD-4, Factor VIII, Factor IX, von Willebrand Factor, TPA, urokinase, hirudin, interferons, TNF, interleukins, hematopoietic growth factors, antibodies, albumin, leptin, transferin and nerve growth factors.

Peptide Hormones. Peptide hormones claimed herein for engineering in neuroendocrine cells are grouped into three classes with specific examples given for each. These classes are defined by the complexity of their post-translational processing. Class I is represented by Growth Hormone, Prolactin and Parathyroid hormone. A more extensive list of human peptides that are included in Class I is given in Table 1. These require relatively limited proteolytic processing followed by storage and stimulated release from secretory granules. Class II is represented by Insulin and Glucagon. A more extensive list of human peptide hormones that are included in Class II are given in Table 2. Further proteolytic processing is required, with both endoproteases and carboxypeptidases processing of larger precursor molecules occurring in the secretory granules. Class III is represented by Amylin, Glucagon-like Peptide I and Calcitonin. Again, a more extensive list of Class III human peptide hormones is given in Table 3. In addition to the proteolytic processing found in the Class II peptides, amidation of the C-terminus is required for proper biological function. Examples of engineering expression of all three of these classes of peptide hormones in a neuroendocrine cell are found in this patent.

TABLE 1

Class I Human Peptide Hormones

Growth Hormone
Prolactin
Placental Lactogen
Luteinizing Hormone
Follicle-stimulating Hormone
Chorionic Gonadotropin
Thyroid-stimulating Hormone

TABLE 2

Human Peptide Hormones Processed by
Endoproteases from Larger Precursors

Adrenocorticotropin (ACTH)
Angiotensin I and II
β-endorphin
β-Melanocyte Stimulating Hormone (β-MSH)
Cholecystokinin
Endothelin I
Galanin
Gastric Inhibitory Peptide (GIP)
Glucagon
Insulin
Lipotropins
Neurophysins
Somatostatin

TABLE 3

Amidated Human Peptide Hormones

Calcium Metabolism Peptides:
    Calcitonin
    Calcitonin Gene related Peptide (CGRP)

β-Calcitonin Gene Related Peptide
Hypercalcemia of Malignancy Factor (1–40) (PTH-rP)
Parathyroid Hormone-related protein (107–139) (PTH-rP)
Parathyroid Hormone-related protein (107–111) (PTH-rP)
Gastrointestinal Peptides:
  Cholecystokinin (27–33) (CCK)
  Galanin Message Associated Peptide, Preprogalanin (65–105)
  Gastrin I
  Gastrin Releasing Peptide
  Glucagon-like Peptide (GLP-1)
  Pancreastatin
  Pancreatic Peptide
  Peptide YY
  PHM
  Secretin
  Vasoactive Intestinal Peptide (VIP)
Pituitary Peptides:
  Oxytocin
  Vasopressin (AVP)
  Vasotocin
Enkephalins:
  Enkephalinamide
  Metorphinamide (Adrenorphin)
Alpha Melanocyte Stimulating Hormone (alpha-MSH)
Atrial Natriuretic Factor (5–28) (ANF)
Amylin
Amyloid P Component (SAP-1)
Corticotropin Releasing Hormone (CRH)
Growth Hormone Releasing Factor (GHRH)
Luteinizing Hormone-Releasing Hormone (LHRH)
Neuropeptide Y
Substance K (Neurokinin A)
Substance P
Thyrotropin Releasing Hormone (TRH)

(ii) Non-Secreted Proteins

Expression of non-secreted proteins can be engineered into neuroendocrine cells. Two general classes of such proteins can be defined. The first are proteins that, once expressed in cells, stay associated with the cells in a variety of destinations. These destinations include the cytoplasm, nucleus, mitochondria, endoplasmic reticulum, golgi, membrane of secretory granules and plasma membrane. Non-secreted proteins are both soluble and membrane associated. The second class of proteins are ones that are normally associated with the cell, but have been modified such that they are now secreted by the cell. Modifications would include site-directed mutagenesis or expression of truncations of engineered proteins resulting in their secretion as well as creating novel fusion proteins that result in secretion of a normally non-secreted protein.

Cells engineered to produce such proteins could be used for either in vitro production of the protein or for in vivo, cell-based therapies. In vitro production would entail purification of the expressed protein from either the cell pellet for proteins remaining associated with the cell or from the conditioned media from cells secreting the engineered protein. In vivo, cell-based therapies would either be based on secretion of the engineered protein or beneficial effects of the cells expressing a non-secreted protein.

The cDNA's encoding a number of therapeutically useful human proteins are available. These include cell surface receptors, transporters and channels such as GLUT-2, CFTR, leptin receptor, sulfonylurea receptor, β-cell inward rectifying channels, etc. Other proteins include protein processing enzymes such as PC2 and PC3, and PAM, transcription factors such as IPF1, and metabolic enzymes such as adenosine deaminase, phenylalanine hydroxylase, glucocerebrosidase.

Engineering mutated, truncated or fusion proteins into neuroendocrine cells also is contemplated. Examples of each type of engineering resulting in secretion of a protein are given (Stoller and Mains, 1989; Ferber et al., 1991; Mains et al., 1995). Reviews on the use of such proteins for studying the regulated secretion pathway are also cited (Burgess and Kelly, 1987; Chavez et al., 1994).

C. Genetic Constructs

Also claimed in this patent are examples of DNA expression plasmids designed to optimize production of the heterologous proteins. These include a number of enhancers/promoters from both viral and mammalian sources that drive expression of the genes of interest in neuroendocrine cells. Elements designed to optimize messenger RNA stability and translatability in neuroendocrine cells are defined. The conditions for the use of a number of dominant drug selection markers for establishing permanent, stable neuroendocrine cell clones expressing the peptide hormones are also provided, as is an element that links expression of the drug selection markers to expression of the heterologous polypeptide.

(i) Vector Backbone

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding a particular gene is not believed to be important, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the gene of interest. The use of other viral or mammalian cellular or bacterial phage promoters which are well-known in the art to achieve expression of a gene of interest is contemplated as well, provided that the levels of expression are sufficient for a given purpose.

By employing a promoter with well-known properties, the level and pattern of expression of the gene product following transfection can be optimized. Further, selection of a promoter that is regulated in response to specific physiologic signals can permit inducible expression of the gene product. Tables 4 and 5 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 4 and Table 5). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 4

ENHANCER

Immunoglobulin Heavy Chain
Immunoglobulin Light Chain
T-Cell Receptor
HLA DQ α and DQ β
β-Interferon
Interleukin-2
Interleukin-2 Receptor
Gibbon Ape Leukemia Virus
MHC Class II 5 or HLA-DRα
β-Actin
Muscle Creatine Kinase
Prealbumin (Transthyretin)
Elastase I
Metallothionein
Collagenase
Albumin Gene
α-Fetoprotein
α-Globin
β-Globin
c-fos
c-HA-ras
Insulin Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40 or CMV
Polyoma
Retroviruses
Papilloma Virus
Hepatitis B Virus
Human Immunodeficiency Virus

TABLE 5

| Element | Inducer |
|---|---|
| MT II | Phorbol Ester (TFA) Heavy metals |
| MMTV (mouse mammary tumor virus) | Glucocorticoids |
| β-Interferon | poly(rI)X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TFA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2 kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988;, Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

(ii) Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. The inventors have employed the human Growth Hormone and SV40 polyadenylation signals in that they were convenient and known to function well in the target cells employed. Also contemplated as an element of the expression cassette is a terminator. These elements can serve to enhance message levels and to minimize read through from the cassette into other sequences.

(iii) Selectable Markers

In certain embodiments of the invention, the delivery of a nucleic acid in a cell may be identified in vitro or in vivo by including a marker in the expression construct. The marker would result in an identifiable change to the transfected cell permitting easy identification of expression. Usually the inclusion of a drug selection marker aids in cloning and in the selection of transformants, for example, neomycin, puromycin, hygromycin, DHFR, GPT, zeocin and histidinol. Alternatively, enzymes such as herpes simplex virus thymidine kinase (tk) (eukaryotic) or chioramphenicol acetyltransferase (CAT) (prokaryotic) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iv) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988; Jang et al., 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

D. Bioreactors and Large Scale Cultures

The ability to produce biologically active polypeptides is increasingly important to the pharmaceutical industry. Over the last decade, advances in biotechnology have led to the production of important proteins and factors from bacteria, yeast, insect cells and from mammalian cell culture. Mammalian cultures have advantages over cultures derived from the less advanced lifeforms in their ability to post-translationally process complex protein structures such as disulfide-dependent folding and glycosylation. Neuroendocrine cell types have added unique capacities of endoproteolytic cleaving, C-terminal amidation and regulated secretion. Indeed, mammalian cell culture is now the preferred source of a number of important proteins for use in human and animal medicine, especially those which are relatively large, complex or glycosylated.

Development of mammalian cell culture for production of pharmaceuticals has been greatly aided by the development in molecular biology of techniques for design and construction of vector systems highly efficient in mammalian cell cultures, a battery of useful selection markers, gene amplification schemes and a more comprehensive understanding of the biochemical and cellular mechanisms involved in procuring the final biologically-active molecule from the introduced vector.

However, the traditional selection of cell types for expressing heterologous proteins has generally been limited to the more "common" cell types such as CHO cells, BHK cells, C127 cells and myeloma cells. In many cases, these cell types were selected because there was a great deal of preexisting literature on the cell type (e.g., "cookbook" methods for transfection of the cells) or the cell was simply being carried in the laboratory at the time the effort was made to express a peptide product. Frequently, factors which affect the downstream (in this case, beyond the T-75 flask) side of manufacturing scale-up were not considered before selecting the cell line as the host for the expression system. Also, development of bioreactor systems capable of sustaining very high density cultures for prolonged periods of time have not lived up to the increasing demand for increased production at lower costs.

The present invention will take advantage of the biochemical and cellular capacities of secretory cells as well as of recently available bioreactor technology. Growing cells according to the present invention in a bioreactor allows for large scale production and secretion of complex, fully biologically-active polypeptides into the growth media. By designing a defined media with low contents of complex proteins and using a scheme of timed-stimulation of the secretion into the media for increased titer, the purification strategy can be greatly simplified, thus lowering production cost.

(i) Anchorage-Dependent Versus Non-Anchorage-Dependent Cultures

Animal and human cells can be propagated in vitro in two modes: as non-anchorage dependent cells growing freely in suspension throughout the bulk of the culture; or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. Large scale suspension culture based on microbial (bacterial and yeast) fermentation technology has clear advantages for the manufacturing of mammalian cell products. The processes are relatively simple to operate and straightforward to scale up. Homogeneous conditions can be provided in the reactor which allows for precise monitoring and control of temperature, dissolved oxygen, and pH, and ensure that representative samples of the culture can be taken.

However, suspension cultured cells cannot always be used in the production of biologicals. Suspension cultures are still considered to have tumorigenic potential and thus their use as substrates for production put limits on the use of the resulting products in human and veterinary applications (Petricciani, 1985; Larsson, 1987). Viruses propagated in suspension cultures as opposed to anchorage-dependent cultures can sometimes cause rapid changes in viral markers, leading to reduced immunogenicity (Bahnemann, 1980). Finally, sometimes even recombinant cell lines can secrete considerably higher amounts of products when propagated as anchorage-dependent cultures as compared with the same cell line in suspension (Nilsson, 1987). For these reasons, different types of anchorage-dependent cells are used extensively in the production of different biological products.

The current invention includes cells which are anchorage-dependent of nature. RIN cells, e.g., are strictly anchorage-dependent, and when grown in suspension, the cells will attach to each other and grow in clumps, eventually suffocating cells in the inner core of each clump as they reach a size that leaves the core cells unsustainable by the culture conditions. Therefore, an efficient means of large-scale culture of anchorage-dependent cells is needed in order to effectively take advantage of these cells' capacity to secrete heterologous proteins.

(ii) Reactors and Processes for Suspension

Large scale suspension culture of mammalian cultures in stirred tanks was undertaken. The instrumentation and controls for bioreactors adapted, along with the design of the fermentors, from related microbial applications. However, acknowledging the increased demand for contamination control in the slower growing mammalian cultures, improved aseptic designs were quickly implemented, improving dependability of these reactors. Instrumentation and controls are basically the same as found in other fermentors and include agitation, temperature, dissolved oxygen, and pH controls. More advanced probes and autoanalyzers for on-line and off-line measurements of turbidity (a function of particles present), capacitance (a function of viable cells present), glucose/lactate, carbonate/bicarbonate and carbon dioxide are available. Maximum cell densities obtainable in suspension cultures are relatively low at about $2-4 \times 10^6$ cells/ml of medium (which is less than 1 mg dry cell weight per ml), well below the numbers achieved in microbial fermentation.

Two suspension culture reactor designs are most widely used in the industry due to their simplicity and robustness of operation - the stirred reactor and the airlift reactor. The stirred reactor design has successfully been used on a scale of 8000 liter capacity for the production of interferon (Phillips et al., 1985; Mizrahi, 1983). Cells are grown in a stainless, steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easy, has good mass transfer of gasses and generates relatively low shear forces.

Most large-scale suspension cultures are operated as batch or fed-batch processes because they are the most straightforward to operate and scale up. However, continuous processes based on chemostat or perfusion principles are available.

A batch process is a closed system in which a typical growth profile is seen. A lag phase is followed by exponential, stationary and decline phases. In such a system, the environment is continuously changing as nutrients are depleted and metabolites accumulate. This makes analysis of factors influencing cell growth and productivity, and hence optimization of the process, a complex task. Productivity of a batch process may be increased by controlled feeding of key nutrients to prolong the growth cycle. Such a fed-batch process is still a closed system because cells, products and waste products are not removed.

In what is still a closed system, perfusion of fresh medium through the culture can be achieved by retaining the cells with a fine mesh spin filter and spinning to prevent clogging. Spin filter cultures can produce cell densities of approximately $5 \times 10^7$ cells/ml. A true open system and the simplest perfusion process is the chemostat in which there is an inflow of medium and an outflow of cells and products. Culture medium is fed to the reactor at a predetermined and constant rate which maintains the dilution rate of the culture at a value less than the maximum specific growth rate of the cells (to prevent washout of the cells mass from the reactor). Culture fluid containing cells and cell products and byproducts is removed at the same rate. These perfused systems are not in commercial use for production from mammalian cell culture.

(iii) Non-perfused attachment systems.

Traditionally, anchorage-dependent cell cultures are propagated on the bottom of small glass or plastic vessels. The restricted surface-to-volume ratio offered by classical and traditional techniques, suitable for the laboratory scale, has created a bottleneck in the production of cells and cell products on a large scale. In an attempt to provide systems that offer large accessible surfaces for cell growth in small culture volume, a number of techniques have been proposed: the roller bottle system, the stack plates propagator, the spiral film bottles, the hollow fiber system, the packed bed, the plate exchanger system, and the membrane tubing reel. Since these systems are non-homogeneous in their nature, and are sometimes based on multiple processes, they suffer from the following shortcomings—limited potential for scale-up, difficulties in taking cell samples, limited potential for measuring and controlling the system and difficulty in maintaining homogeneous environmental conditions throughout the culture.

Despite these drawbacks, a commonly used process of these systems is the roller bottle. Being little more than a large, differently shaped T-flask, simplicity of the system makes it very dependable and, hence, attractive. Fully automated robots are available that can handle thousands of roller bottles per day, thus eliminating the risk of contamination and inconsistency associated with the otherwise required intense human handling. With frequent media changes, roller bottle cultures can achieve cell densities of close to $0.5 \times 10^6$ cells/cm$^2$ (corresponding to $10^9$ cells/bottle or $10^7$ cells/ml of culture media).

(iv) Cultures on Microcarriers

In an effort to overcome the shortcomings of the traditional anchorage-dependent culture processes, van Wezel (1967) developed the concept of the microcarrier culturing systems. In this system, cells are propagated on the surface of small solid particles suspended in the growth medium by slow agitation. Cells attach to the microcarriers and grow gradually to confluency of the microcarrier surface. In fact, this large scale culture system upgrades the attachment dependent culture from a single disc process to a unit process in which both monolayer and suspension culture have been brought together. Thus, combining the necessary surface for the cells to grow with the advantages of the homogeneous suspension culture increases production.

The advantages of microcarrier cultures over most other anchorage-dependent, large-scale cultivation methods are several fold. First, microcarrier cultures offer a high surface-to-volume ratio (variable by changing the carrier concentration) which leads to high cell density yields and a potential for obtaining highly concentrated cell products. Cell yields are up to $1-2 \times 10^7$ cells/ml when cultures are propagated in a perfused reactor mode. Second, cells can be propagated in one unit process vessels instead of using many small low-productivity vessels (i.e., flasks or dishes). This results in far better utilization and a considerable saving of culture medium. Moreover, propagation in a single reactor leads to reduction in need for facility space and in the number of handling steps required per cell, thus reducing labor cost and risk of contamination. Third, the well-mixed and homogeneous microcarrier suspension culture makes it possible to monitor and control environmental conditions (e.g., pH, pO$_2$, and concentration of medium components), thus leading to more reproducible cell propagation and product recovery. Fourth, it is possible to take a representative sample for microscopic observation, chemical testing, or enumeration. Fifth, since microcarriers settle out of suspension easily, use of a fed-batch process or harvesting of cells can be done relatively easily. Sixth, the mode of the anchorage-dependent culture propagation on the microcarriers makes it possible to use this system for other cellular manipulations, such as cell transfer without the use of proteolytic enzymes, cocultivation of cells, transplantation into animals, and perfusion of the culture using decanters, columns, fluidized beds, or hollow fibers for microcarrier retainment. Seventh, microcarrier cultures are relatively easily scaled up using conventional equipment used for cultivation of microbial and animal cells in suspension.

(v) Microencapsulation of Mammalian Cells

One method which has shown to be particularly useful for culturing mammalian cells is microencapsulation. The mammalian cells are retained inside a semipermeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. Lim (1982) describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquified by treating the droplet in a chelating agent to remove the calcium ions. Other methods use cells in a calcium solution to be dropped into a alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150–1500 μm in diameter, are easily retained in a perfused reactor using a fine-meshed screen. The ratio of capsule volume to total media volume can kept from as dense as 1:2 to 1:10. With intracapsular cell densities of up to $10^8$, the effective cell density in the culture is $1-5 \times 10^7$.

The advantages of microencapsulation over other processes include the protection from the deleterious effects of shear stresses which occur from sparging and agitation, the ability to easily retain beads for the purpose of using perfused systems, scale up is relatively straightforward and the ability to use the beads for implantation.

(vi) Perfused Attachment Systems

Perfusion refers to continuous flow at a steady rate, through or over a population of cells (of a physiological nutrient solution). It implies the retention of the cells within the culture unit as opposed to continuous-flow culture which washes the cells out with the withdrawn media (e.g., chemostat). The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential. The current use of perfused culture is in response to the challenge of growing cells at high densities (i.e., $0.1-5 \times 10^8$ cells/ml). In order to increase densities beyond $2-4 \times 10^6$ cells/ml (or $2 \times 10^5$ cells/cm$^2$), the medium has to be constantly replaced with a fresh supply in order to make up for nutritional deficiencies and to remove toxic products. Perfusion allows for a far better control of the culture environment (pH, pO$_2$, nutrient levels, etc.) and is a means of significantly increasing the utilization of the surface area within a culture for cell attachment.

Microcarrier and microencapsulated cultures are readily adapted to perfused reactors but, as noted above, these culture methods lack the capacity to meet the demand for cell densities above $10^8$ cells/ml. Such densities will provide for the advantage of high product titer in the medium (facilitating downstream processing), a smaller culture system (lowering facility needs), and a better medium utilization (yielding savings in serum and other expensive additives). Supporting cells at high density requires extremely efficient perfusion techniques to prevent the development of non-homogeneity. This means the use of highly sophisticated procedures and apparati and has, until recently, been confmed to a relatively small scale.

(vii) CelliGen™ Bioreactor System

The development of a perfused packed-bed reactor using a bed matrix of a non-woven fabric has provided a means for maintaining a perfusion culture at densities exceeding $10^8$ cells/ml of the bed volume (CelliGen™, New Brunswick Scientific, Edison, N.J.; Wang et al., 1992; Wang et al., 1993; Wang et al., 1994). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 μm to 100 μm, providing for a high internal volume with pore volumes corresponding to 1 to 20 times the volumes of individual cells.

In comparison to other culturing systems, this approach offers several significant advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and produced in low-protein medium which facilitates subsequent purification steps. Also, the unique design of this reactor system offers an easier way to scale up the reactor. Currently, sizes up to 30 liter are available. One hundred liter and 300 liter versions are in development and theoretical calculations support up to a 1000 liter reactor. This technology is explained in detail in WO 94/17178 (Aug. 4, 1994, Freedman et al.), which is hereby incorporated by reference in its entirety.

A number of culturing parameters, used in conjunction with the CelliGen™ system, have been demonstrated to play a role in increased production. For example, the CelliGen™ Plus reactor system, including the use of non-woven polyester fiber matrix (preferably, Fibra-Cel™) and centrifugal lift impeller (preferably, Fibra-Cel™) are system components that give improved yields. Also, several media formulations have been employed with improved performance. For example, use of serum free medium is preferred, as is the use of cholesterol rich lipid extract (0.01% to 0.10%, volume to volume), ascorbic acid (from between about 0.001 to 0.100 mM), glutamate (rather than 2 mM glutamine) at 2 to 20 mM, preferably 4 mM, alpha ketoglutarate (rather than 2 mM glutamine) at 2 to 20 mM, preferably 4 mM, and the absence of growth promoting factors.

E. In Vivo Delivery and Treatment Protocols

It is proposed that engineered cells of the present invention may be introduced into animals with certain needs, such as animals with insulin-dependent diabetes. In the diabetic treatment aspects, ideally cells are engineered to achieve glucose dose responsiveness closely resembling that of islets. However, other cells will also achieve advantages in accordance with the invention. It should be pointed out that the experiments of Madsen and coworkers have shown that implantation of poorly differentiated rat insulinoma cells into animals results in a return to a more differentiated state, marked by enhanced insulin secretion in response to metabolic fuels (Madsen et al., 1988). These studies suggest that exposure of engineered cell lines to the in vivo milieu may have some effects on their response(s) to secretagogues.

The preferred methods of administration involve the encapsulation of the engineered cells in a biocompatible coating. In this approach, the cells are entrapped in a capsular coating that protects the contents from immunological responses. One preferred encapsulation technique involves encapsulation with alginate-polylysine-alginate. Capsules made employing this technique generally have a diameter of approximately 1 mm and should contain several hundred cells.

Cells may thus be implanted using the alginate-polylysine encapsulation technique of O'Shea and Sun (1986), with modifications, as later described by Fritschy et al. (1991). The engineered cells are suspended in 1.3% sodium alginate and encapsulated by extrusion of drops of the cell/alginate suspension through a syringe into $CaCl_2$. After several washing steps, the droplets are suspended in polylysine and rewashed. The alginate within the capsules is then reliquified by suspension in 1 mM EGTA and then rewashed with Krebs balanced salt buffer.

An alternative approach is to seed Amicon fibers with cells of the present invention. The cells become enmeshed in the fibers, which are semipermeable, and are thus protected in a manner similar to the micro encapsulates (Altman et al., 1986). After successful encapsulation or fiber seeding, the cells may be implanted intraperitoneally, usually by injection into the peritoneal cavity through a large gauge needle (23 gauge).

A variety of other encapsulation technologies have been developed that are applicable to the practice of the present invention (see, e.g., Lacy et al., 1991; Sullivan et al., 1991; WO 91/10470; WO 91/10425; WO 90/15637; WO 90/02580; U.S. Pat. No. 5,011,472; U.S. Pat. No. 4,892,538; and WO 89/01967; each of the foregoing being incorporated by reference).

Lacy et. al. (1991) encapsulated rat islets in hollow acrylic fibers and immobilized these in alginate hydrogel. Following intraperitoneal transplantation of the encapsulated islets into diabetic mice, normoglycemia was reportedly restored. Similar results were also obtained using subcutaneous implants that had an appropriately constructed outer surface on the fibers. It is therefore contemplated that engineered cells of the present invention may also be straightforwardly "transplanted" into a mammal by similar subcutaneous injection.

Sullivan et. al. (1991) reported the development of a biohybrid perfused "artificial pancreas", which encapsulates islet tissue in a selectively permeable membrane. In these studies, a tubular semi-permeable membrane was coiled inside a protective housing to provide a compartment for the islet cells. Each end of the membrane was then connected to an arterial polytetrafluoroethylene (PTFE) graft that extended beyond the housing and joined the device to the vascular system as an arteriovenous shunt. The implantation of such a device containing islet allografts into pancreatectomized dogs was reported to result in the control of fasting glucose levels in 6/10 animals. Grafts of this type encapsulating engineered cells could also be used in accordance with the present invention.

The company Cytotherapeutics has developed encapsulation technologies that are now commercially available that will likely be of use in the application of the present invention. A vascular device has also been developed by Biohybrid, of Shrewsbury, Mass., that may have application to the technology of the present invention.

Implantation employing such an encapsulation technique are preferred for a variety of reasons. For example, transplantation of islets into animal models of diabetes by this method has been shown to significantly increase the period of normal glycemic control, by prolonging xenograft survival compared to unencapsulated islets (O'Shea and Sun, 1986; Fritschy et al., 1991). Also, encapsulation will prevent uncontrolled proliferation of clonal cells. Capsules containing cells are implanted (approximately 1,000–10,000/animal) intraperitoneally and blood samples taken daily for monitoring of blood glucose and insulin.

An alternate approach to encapsulation is to simply inject glucose-sensing cells into the scapular region or peritoneal cavity of diabetic mice or rats, where these cells are reported to form tumors (Sato et al., 1962). Implantation by this approach may circumvent problems with viability or function, at least for the short term, that may be encountered with the encapsulation strategy. This approach will allow testing of the function of the cells in experimental animals but obviously is not applicable as a strategy for treating human diabetes.

Engineering of primary cells isolated from patients is also contemplated as described by Dr. Richard Mulligan and colleagues using retroviral vectors for the purposes of introducing foreign genes into bone marrow cells (see, e.g., Cone et al., 1984; Danos et al., 1988). The cells of the bone marrow are derived from a common progenitor, known as pluripotent stem cells, which give rise to a variety of blood borne cells including erythrocytes, platelets, lymphocytes, macrophages, and granulocytes. Interestingly, some of these cells, particularly the macrophages, are capable of secreting peptides such as tumor necrosis factor and interleukin 1 in response to specific stimuli. There is also evidence that these cells contain granules similar in structure to the secretory granules of β-cells, although there is no clear evidence that such granules are collected and stored inside macrophages as they are in β-cells (Stossel, 1987).

It may ultimately be possible to use the present invention in combination with that previously described by the one of the present inventors (U.S. Pat. No. 5,427,940, incorporated herein by reference) in a manner described for clonal cells to engineer primary cells that perform glucose-stimulated insulin secretion. This approach would completely circumvent the need for encapsulation of cells, since the patient's own bone marrow cells would be used for the engineering and then re-implanted. These cells would then develop into their differentiated form (i.e., the macrophage) and circulate in the blood where they would be able to sense changes in circulating glucose by secreting insulin.

Alternatively, it may be desirable to introduce genetic constructs to cells in vivo. There are a number of way in which nucleic acids may introduced into cells. Several methods are outlined below.

(i) Adenovirus

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization or adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlemneyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

(ii) Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact_sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

(iii) Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

(iv) Non-Viral Vectors

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. As described above, the preferred mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benveniendy and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectanine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

(v) Pharmaceutical Compositions

Where clinical applications are contemplated, it will be necessary to prepare pharmaceutical compositions—either gene delivery vectors or engineered cells—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors and cells of the present invention are advantageously administered in the form of injectable compositions either as liquid solutions or suspensions; solid forms suitable for solution in, or suspension in, liquid prior to injection also may be prepared. These preparations also may be emulsified. A typical composition for such purposes comprises a 50 mg or up to about 100 mg of human serum albumin per milliliter of phosphate-buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

F. EXAMPLES

Example 1

Homologous Recombination

A. Hexokinase I Targeted Disruption

Methods

Construction of gene replacement vector. A 15 kB clone, containing a portion of the rat hexokinase I (HKI) gene encompassing exon 1, about 0.2 kB of intron 1 and about 14.8 kB of sequence upstream of exon 1, was employed. Sequence and maps of this clone aided in the mapping of the HKI gene and in the isolation of homologous isogenic sequences from RIN genomic DNA. The novel 1082 base sequence of the non-transcribed rat HKI genomic DNA as well as the first 170 bases of HKI transcribed DNA (Schwab and Wilson, 1989) is given as SEQ ID NO: 13. A plasmid vector providing positive and negative selection, pPolIIshort-neobPA-HSV-tk, is derived from the pGEM3Zf (+) backbone and contains a neomycin phosphotransferase gene (positive selection) and two tandem copies of herpes simplex virus thymidine kinase gene (HSV-tk) that provide negative selection in the presence of ganciclovir (Ishibashi et al., 1993). pPolllshort-neobPA-HSV-tk was modified to create pAT9 by creating a unique NotI site 5' of the Neo cassette (FIG. 1). A 873 base pair fragment was amplified from RIN genomic DNA using oligos (TTTCCCCTCGAGCACCGCCCGGAACAGTACC, SEQ ID NO: 16 and GTTGCGCCTCGAGCATGCTGACGGTGGGGG, SEQ ID NO: 17) to provide a short arm of homology to the HKI gene. The sequence extends 5' from the first methionine of exon 1 and is flanked by engineered XhoI sites.

In addition, a 1121 base fragment was amplified from RIN genomic DNA using oligos (GTTGGACTCGAGAGTCACCTAAGGGCCTATG, SEQ ID NO: 18 and GTTGCGCCTCGAGCATGCTGACGGTGGGGG, SEQ ID NO: 17), providing a longer short arm to serve as a positive control for screening for homologous recombinants by PCR™. The 873 and 1121 base pair PCR™ fragments were restricted with XhoI and subcloned into pAT9 at a unique XhoI site which is flanked by the Neo cassette and the copies of HSV-tk (FIG. 1), generating pAT21 and pAT22, respectively.

Southern blot analysis in RIN 1046-38 genomic DNA with a probe within intron 1 revealed a 16 kB KpnI fragment. This fragment was enriched by sucrose density ultracentrifugation, modified with adapters to create flanking Not I sites, and subcloned into lambda Dash II (Stratagene, La Jolla, Calif.). Recombinant phages containing the fragment were isolated by plaque screening. The 16 kB NotI fragment was cloned into the unique Not I site of pAT22 to provide a long arm of homology to the HKI gene (FIG. 1), generating pAT23, the HK1 replacement vector.

Cell culture, electrolporation, and drug selection. Various cell lines derived from the rat insulinoma RIN 1046-38 line (Clark et al., 1990) were grown in Medium 199 with Earle's salts, containing 11 mM glucose and 5% fetal bovine serum. Exogenous DNA was introduced into the cells by electroporation. RIN cell lines were grown to 50% to 75% confluence, harvested by trypsinization, washed once with phosphate-buffered saline (PBS), and resuspended in PBS for counting. For each electroporation, $1 \times 10^7$ cells were pelleted by centrifugation at 1000 rpm for 2 minutes and resuspended in 0.4 ml cold Electroporation Buffer (137 mM NaCl, 6.1 mM glucose, 5 mM KCl, 0.7 mM $Na_2HPO4$, 20 mM Hepes, pH 7.0). DNA was added to the cell suspension to achieve a final concentration of 30–50 micrograms per ml. DNA was electroporated into cells in a 2 mm cuvette at 170 volts and 510 microFaradies using an Electro Cell Manipulator 600 (BTX, Inc., San Diego, Calif.) Cells were plated in non-selective medium and cultured for 2 to 3 days. Medium containing G418 at a final concentration of 500 micrograms per ml was used for 14 days to select for clones integrated with the neomycin resistance marker. Following positive selection in G418, ganciclovir (Syntex Inc., Palo Alto, Calif.) at a final concentration of 6 $\mu$M was used to selectively kill clones expressing HSV-tk. Ganciclovir was applied for 3 days; cells were then maintained in medium containing G418.

PCR™ assay for targeted recombinants. Following positive selection in G418 and negative selection in ganciclovir, clones were grown until visible by the naked eye. Individual colonies were picked, dispersed in trypsin, and divided between duplicate cultures into 96-well plates. Following 10 to 15 days in culture, cells of one duplicate were rinsed in PBS and lysed by incubation at 37° C. for 8 to 12 hours in fifty microliters of Lysis Buffer (16.6 mM ammonium sulfate, 67 mM Tris-HCl, 6.7 mM $MgCl_2$, 5.0 mM 2-mercaptoethanol, 6.7 $\mu$M EDTA, 1.7 $\mu$M SDS, 50 $\mu$g/ml proteinase K, pH 8.8), (Willnow and Herz, 1994). Five microliters of lysate were used as a template in a twenty-five microliter polymerase chain reaction (PCR™) in 16.6 mM ammonium sulfate, 67 mM Tris-HCl, 6.7 mM MgCl2, 5.0 mM 2-mercaptoethanol, 6.7 $\mu$M EDTA, 1 mM each dNTP, 80 $\mu$g/ml BSA, 0.8 $\mu$g/ml of each primer, and 2.5 units Taq DNA polymerase. The amplification program consisted of 92° C., 40 seconds, 57° C. 40 seconds, 75° C., 1 minute (40 cycles) and a final extension for 5 minutes at 75° C. The oligonucleotides used to amplify disrupted HKI included a primer in the 3' end of the Neo cassette (5'GATTGGGAAGACAATAGCAGGCATGC3' SEQ ID NO:19, primer 1, FIG. 1 Ishibashi et al., 1993) and a primer in the HKI gene upstream of the putative recombination site (5'AGTCGCCTCTGCATGTCTGAGTTC3' SEQ ID NO:20, primer 3, FIG. 1). The plasmid pAT22, containing the longer short arm of homology, served as a positive control in this PCR™ reaction. A second control PCR™ reaction was also included using primer 1 and a primer in the HK1 gene downstream of the recombination site (5'CTTGAGCTCTTACATGGTGTCACG3' SEQ ID NO:21, primer 2, FIG. 1). This control PCR™ reaction should detect both homologous and random integrants of the HK1 replacement vector. Recombinants detected in the first screen were confirmed in a second PCR™ reaction for which no positive control plasmid exists. The absence of such a control negates the possibility of a false positive due to contamination. The primers in this secondary screen were primer 1 and primer 4 (5'TCCCCAGGCGTGGGGTAGAAG3' SEQ ID NO:22), an oligonucleotide upstream of the recombination site in the HKI gene (FIG. 1). PCR™ products analyzed either by gel electrophoresis or a slot blot assay. For electrophoresis, reaction products were fractionated in 1% agarose gels in Tris-borate/EDTA buffer (9 mM Tris-borate, 0.2 mM EDTA). DNA was visualized by staining in ethidium bromide. For slot-blots, reaction products were denatured in 0.5 N NaOH, 1.5 M NaCl, neutralized in 1.0 M Tris-HCl, pH 7.5, 1.5 M NaCl, and transferred to a nylon membrane using a 96-well blot apparatus (Scheichller and Schuell, Keene, N. H.). DNA was cross-linked to the membrane and HKI amplified products were detected by hybridization with $^{32}$P-labelled oligonucleotides complementary to HKI and internal to primers used in the amplification reaction. Positive clones were replated in 96-well dishes to obtain densities of one cell per well. These clones were allowed to grow and assayed by PCR™ with the primers described above. This cycle of dilution cloning was repeated until all clones of a plating were positive in the assay.

Genomic Southern analysis. RIN clones that were positive by PCR™ for a disrupted allele of HKI were assayed by genomic Southern. Genomic DNA was isolated using reagents and protocols of the QIAamp Blood Kit (catalog number 29104, Qiagen, Inc., Chatsworth Calif.) Five to ten micrograms of DNA were digested with enzymes as indicated and fractionated through 0.8% agarose gels using TEAN buffer (0.04 M Tris-HCI, 0.025 M sodium acetate, 0.018 M NaCl, 25 mM EDTA, pH 8.15). Electrophoresis was conducted for 12 to 16 hours at 25 to 35 volts with recirculation of the buffer. DNA was visualized by staining with ethidium bromide. DNA in the gel was denatured for 30 minutes in 0.5 N NaOH, 1.5 M NaCl. Following neutralization in 1 M Tris-HCl, pH 7.5, 1 M NaCl for 30 minutes, DNA was transferred to a nylon membrane (Hybond-N+, Amersham) in 10×SSC (1X: 0.15 M NaCl, 0.015 M sodium citrate) and cross-linked to the membrane by ultraviolet radiation (UV Stratalinker 2400, Stratagene, Inc.). Radiolabelled probes ($^{32}$P) for hybridization to and detection of genomic fragments were synthesized as directed using the rediprime Random Primer Labelling Kit (RPN 1633, Amersham Life Sciences). Membranes were prehybridized and hybridized in Rapid-hyb Buffer (NIF939, Amersham Life Sciences). All incubations and washes were performed in a Micro-4 Hybridization Oven (Hybaid imited). Membranes were exposed to X-OMAT, AR5 film (Kodak) to obtain autodiongraphic signals.

Results

Prior to construction of a gene replacement vector, a comparison was made of the copy number of HKI alleles in rat versus RIN genomic DNA. DNA was digested with XbaI, Southern blotted, and probed with a radiolabelled fragment from intron 1 of the HKI gene. Autoradiography revealed equivalent signals derived from the rat and RIN HKI gene fragments. Presumably, these signals correspond to diploidy of the HKI gene in both the rat and RIN genomes. This conclusion is supported by data that show RIN-derived cell lines to have maintained a diploid state in their chromosomes. Karyotype analysis of RIN 1046-38 showed a distribution of 35 to 40 chromosomes with the normal rat compliment being 42 chromosomes.

The HKI replacement vector (FIG. 1) was transfected into RIN cells in three separate electroporations (EP): EP81, EP86, EP95. These electroporations differ from each other in their temporal distributions, the identity of the parental cell line, and the number of clones screened from each (Table 6). EP81 was derived from a low passage RIN 1046-38 cell line. Of the 500 colonies screened, none were positive for disruption of an HKI allele. RIN-52/17, a RIN 1046-38 derived clone, was the parental line in EP86. One positive clone was detected in a screen of about 970 colonies. RIN-52/9, a cell line that expresses high levels of rat glucokinase and is resistant to hygromycin, was used as a parental line in EP95. About 3200 clones were screened by PCR™ for the presence of a disrupted HKI allele. None were positive.

Potentially, the loss of an HKI allele could result in a growth disadvantage and thereby lead to a lower frequency of detecting HKI gene replacement events. To negate a potential metabolic disadvantage conferred by loss of HKI activity, efforts were made to create parental cell lines that overexpress rat glucokinase. Such parental lines could potentially serve two functions—first, to prevent metabolic stress should phosphorylation of glucose became rate-limiting in transformed cell lines with diminished HKI activity; and second, to restore a high $K_m$ glucose-phosphorylating activity to the RIN lines to shift glucose-responsive insulin secretion towards a more physiological range. RIN-52/17, the parental cell line in EP86, had previously been electroporated with a plasmid conferring hygromycin resistance and containing a copy of the rat glucokinase (GK) cDNA. RIN-52/17 was hygromycin resistant and was thought to express moderate levels of glucokinase from the transgene. Subsequent data confirmed resistance to hygromycin, but disproved expression of GK from the transgene (Table 6). About 1000 individual clones were screened from EP86. From this screen one clone, 86/X4, was positive by PCR™. Clone 86/X4 was initially identified by amplification with primer 1 and primer 3. The molecular weight of the amplified product was equal to that derived from the plasmid control. Confirmation of this clone as containing a disrupted HKI allele was obtained by amplification with primer 1 and primer 4. No plasmid control exists for this PCR™ reaction, therefore, the product is not the result of contamination.

TABLE 6

Electroporation (EP) of RIN Cell Lines with a HK1 Replacement Vector

| EP | Parental line | DrugR,Parental | Transgene | Clones screened | +by PCR ™ |
|---|---|---|---|---|---|
| 81 | RIN 1047-38 | (−) | (−) | 500 | 0 |
| 86 | RIN 52-17 | HygroR | (−) | 970 | 1 |
| 95 | RIN 52-9 | HygroR | rat GK | 3200 | 0 |

Targeted disruption of HK1 was attempted in various RIN lines, in the absence of presence of high levels of expression of rat glucokinase (GK) from a transgene. Cells expressing the transgene were first selected for resistance to hygromycin (HygroR) and then assayed by Western blotting for expression of exogenous rat GK.

The original positive culture of 86/X4 was passaged several times prior to dilutional plating for assessing the purity of the clonal population. 197 individual colonies were cultured in 96-well plates, allowed to grow to 50–70% confluence, trypsinized, and split into cuplicate cultures. Cells from one set of cultures were lysed and screened by PCR™ using primers 1 and 3 (FIG. 1) and then reaction products were analyzed by a slot assay. Two clones were confirmed as containing a disrupted allele of HKI. This result demonstrates two things. First, the original culture that was identified as 86/X4 was a polyclonal rather than a monoclonal population. Second, the clone containing the disrupted allele of HKI seems to have a growth disadvantage compared to other cells in the population. This latter possibility is supported by observations of the growth rates of the purified HKI replacement clone. The pure 86/X4 grows significantly slower (about one-half as fast) than clones randomly integrated with the replacement vector.

Additional data verifying the identity of clone 86/X4 were derived by analysis of genomic DNA by Southern blotting (FIG. 2). DNA was digested with EcoRI and NotI, blotted, and hybridized with a probe upstream of the recombination site (hatched rectangle, FIG. 1). DNA from RIN 1046-38 cells (lane 1) and from RIN-52/17 randomly integrated with pAT23 (lane 2) produce a predicted signal of about 5.5 kB in the autoradiograph. This signal corresponds to a homozygous, wild-type HKI gene. Clone 86/X4 produces two autoradiographic signals in the genomic Southern (lane 3): a 5.5 kB signal corresponding to a wild-type allele and an additional signal (about 4.6 kB), indicative of a HKI allele that has homologously recombined with the replacement vector.

B. Insulin Knockout

Methods

Construction of gene replacement vector. The rat insulin I gene (Genbank accession number J00747) provided a template from which to create primers for amplifying sequences from RIN genomic DNA. A 590 base pair fragment 3' of the rat insulin gene and corresponding to positions 4830 to 5420 was amplified by polymerase chain reaction (PCR™), subcloned, and used as radiolabelled probe. RIN genomic Southerns using this probe revealed a BglII fragment of about 12 kB that extends three prime from position 1176. This fragment was enriched by sucrose density ultracentrifugation and subcloned into BamHI sites of lambda Dash II vector (Stratagene). Recombinant phages containing the fragment were isolated by plaque screening. A portion of this fragment extending from an internal SpeI site to a NotI site provided by the lambda Dash vector was used to provide a long arm of homology to RIN DNA in the context of a replacement vector (FIG. 3). A short arm of homology to RIN DNA (five prime of the rat insulin I gene) was derived by amplification of a fragment corresponding to nucleotides 1822 to 2860. This fragment, flanked by XhoI sites, was cloned into the replacement vector (FIG. 3).

The plasmid backbone (pSL9), used for creating a rat insulin I (RINS-1) replacement vector, provided several features designed to enhance and complement disruption of the rat insulin I gene. First, positive selection for integration of exogenous DNA into the RIN genome was provided by the gene encoding neomycin phosphotransferase. The expression of this gene is linked to the expression of human insulin by an internal ribosome entry site (IRES). This allows disruption of the rat insulin gene to be coupled to expression of human insulin cDNA. Secondly, negative selection, to allow enrichment of targeted over random integration events, was provided by the expression of the type 2 rat glucose transporter (GLUT-2). The presence of a functional GLUT-2 renders cells susceptible to streptozotocin (STZ) toxicity (Schnedl et al., 1994). Thirdly, a unique PacI site at the distal end of the long arm of homology was used to linearize the vector prior to electroporation into RIN cells (FIG. 3).

Cell culture. electroporation, and drug selection. Culture conditions are as described above except that following positive selection in G418, (1 mM for 2.5 h) was used to selectively kill clones expressing a functional Glut-2 transporter.

PCR™ assay for targeted recombinants. Following positive selection in G418 and negative selection in STZ, clones were cultured for about 3–4 weeks. Cells in each well were dispersed in trypsin and divided between duplicate cultures into 96-well plates. Following 10 to 15 days in culture, cells of one duplicate were rinsed in PBS and lysed by incubation at 37° C. for 8 to 12 hours in 50 ttl of Lysis Buffer (16.6 mM ammonium sulfate, 67 mM Tris-HCl, 6.7 mM $MgCl_2$, 5.0 mM 2-mercaptoethanol, 6.7 $\mu$M EDTA, 1.7 $\mu$M SDS, 50 $\mu$g/ml proteinase K, pH 8.8) (Willnow and Herz, 1994). Five microliters of lysate were used as a template in a 25 $\mu$l PCR™ in 16.6 mM ammonium sulfate, 67 mM Tris-HCl, 6.7 mM $MgCl_2$, 5.0 mM 2-mercaptoethanol, 6.7 $\mu$M EDTA, 1 mM each dNTP, 80 $\mu$g/ml 5 BSA, 0.8 $\mu$g/ml of each primer, and 2.5 units Taq DNA polymerase. The amplification program consisted of 40 cycles at 92° C., 40 seconds, 57° C. 40 seconds, 75° C., 1 minute and a final extension for 5 minutes at 75° C., and was performed in a 96-well thermocycler (HB-96V, MJ Research, Inc., Watertown, Mass.) The oligonucleotides used to amplify disrupted RINS-1 included a primer in the 3'-end of the Neo cassette (5'-CAACCGGTGGGACATTTGAGTTGC-3' SEQ ID NO:23, primer 1, FIG. 3) and a primer in the RINS-1 gene upstream of the putative recombination site (5'-CCAAGTCATTATAGAATCATAGTC-3' SEQ ID NO:24, primer 2, FIG. 3). The plasmid pRD1 was created to serve as a positive control in the PCR™ reaction. The backbone of pSL9 was ligated to an insert encompassing all of the short arm of homology and extending an additional 200 base pairs 5'. PCR™ products were analyzed using a slot-blot apparatus (part number 27560, Scheicher and Schuell). Reaction products were denatured in 0.5 N NaOH, 1.5 M NaCl, neutralized in 1.0 M Tris-HCl, pH 7.5, 1.5 M NaCl, and transferred to a nylon membrane. DNA was cross-linked to the membrane and RINS-1 amplified products were detected by hybridization with $^{32}$P-labelled oligonucleotides complementary to RINS-1 and internal to primers used in the amplification reaction. Positive clones were replated in 96-well dishes to obtain densities of one cell per well. These clones were allowed to grow and assayed by PCR™ with the primers described above. This cycle of dilution cloning was repeated until all clones of a plating were positive in the assay.

RIN clones that were positive by PCR™ for a disrupted allele of RINS-1 were assayed by genomic Southern. Genomnic DNA was isolated using reagents and protocols of the QIAamp Blood Kit (catalog number 29104, Qiagen, Inc., Chatsworth, Calif.). Five to ten micrograms of DNA was digested with enzymes as indicated and fractionated through 0.8% agarose gels using a TEAN buffer ( 0.04 M Tris-HCl, 0.025 M sodium acetate, 0.018 M NaCl, 25 mM EDTA, pH 8.15). Electrophoresis was conducted for 12 to 16 hours at 25 to 35 volts with recirculation of the buffer from the positive to the negative electrode. DNA was visualized by staining with ethidium bromide. DNA in the gel was denatured for 30 minutes in 0.5 N NaOH, 1.5 M NaCl. Following neutralization in 1 M Tris-HCl, pH 7.5, 1

M NaCl for 30 minutes, DNA was transferred to a nylon membrane (Hybond-N+, Amersham, Chicago, Ill.) in 10X SSC (1X: 0.15 M NaCl, 0.015 M sodium citrate) and cross-linked to the membrane by ultraviolet radiation (UV Stratalinker 2400, Stratagene, Inc.). Radiolabelled probes (32P) were synthesized as directed using the rediprime Random Primer Labelling Kit (RPN 1633, Amersham Life Sciences). Membranes were prehybridized and hybridized in Rapid-hyb Buffer (NIF939, Amersham Life Sciences). All incubations and washes were performed in a Micro-4 Hybridization Oven (Hybaid Limited). Membranes were exposed to X-OMAT, ARS film (Kodak) to obtain autoradiographic signals.

EXAMPLE 2

Engineering Novel Functions into Cells

A. Human Insulin Expression

Materials and Methods

Expression plasmid construction, general design. Initial expression plasmids were based on pCB6 and pCB7 (Brewer, 1994). These plasmids utilize the strong promoter/enhancer of the human Cytomegalovirus (CMV) immediate-early regulatory sequence to express inserted genes of interest. Efficient polyadenylation of transcribed messenger RNA is directed by the human growth hormone polyadenylation sequence. pCB6 encodes the Neomycin resistance gene conferring resistance to the neomycin analog G418, while pCB7 encodes the hygromycin resistance gene. Both resistant markers are transcribed by the SV40 early promoter.

A second expression plasmid was constructed with many of the same elements as pCB6. The open reading frame of the neomycin resistance gene was amplified with the polymerase chain reaction from pCB6 (Brewer, 1994) using oligos (CCGGATCCCATGATTGAACAAGAT, SEQ ID NO:25 and CCAAGATCTCGCTCAGAAGAACTC, SEQ ID NO:26). The resulting 816 bp amplified product was restricted with BamHI and BglII and subcloned into the BamHI site of pCMV8, generating pCMV8/NEO/hGH PolyA. pCMV8 was derived from pCMV4 (Anderson et al., 1989) following removal of the alpha mosaic virus 4 RNA translational enhancer and replacing it with the 5' leader sequence of the adenovirus tri-partite leader (+14 to +154 of major late transcript) fused to a hybrid intron composed of the adenovirus major late transcript 5'-donor site and a 3'-splice site from a variable region immunoglobulin gene on a 409 bp EcoRI/PstI fragment (SEQ ID NO: 14, Kaufman and Sharp, 1982). Secondly, a portion of the gene encoding the 5'-transcribed leader of the human Glucose Regulated Protein 78 (GRP78) was amplified using the polymerase chain reaction from pThu6.5 (corresponding to bases 372 to 594, Ting and Lee, 1988) using oligos (CCGGATCCAGGTCGACGCCGGCCAA, SEQ ID NO:27 and CGAGATCTTGCCAGCCAGTTGG, SEQ ID NO:28), generating SEQ ID NO:11. The 5'-leader of human GRP 78 has been shown to direct internal initiation of translation allowing for construction of functional polycistronic genes in mammalian cells (Macejak and Sarnow, 1991). The 235 bp amplified product (SEQ ID NO: 11) was restricted with BamHI and BglII and subcloned into the BamHI site of pCMV8/NEO/hGH PolyA generating pCMV8/IRES/NEO/hGH PolyA (FIG. 4B). Unique restriction endonuclease sites exist (5'-SalI/XbaI/BamHI-3') for subcloning fragments into this expression plasmid between the CMV promoter/intron and the internal ribosome entry site/NEO elements. cDNA's or other open reading frames cloned into these sites are transcribed from the CMV promoter into a bicistronic message containing the cDNA as the upstream open reading frame and neomycin resistance (NEO) as the downstream open reading frame. Both open reading frames are translated efficiently, linking neomycin drug resistance and expression of the upstream gene of interest.

A final expression plasmid was designed for expression of genes of interest. The 5' elements found in pCMV8 composed of the 5' leader sequence of the adenovirus tri-partite leader (+14 to +154 of major late transcript) fused to a hybrid intron composed of the adenovirus major late transcript 5' donor site and a 3' splice site from a variable region immunoglobulin gene (SEQ ID NO: 14, Kaufman and Sharp, 1982) was removed by endonuclease restriction by SnaBi and BamHI and ligated into SnaBI and BglII restricted pCB6 (Brewer, 1994), generating pCB6/intron (FIG. 4A). SnaB1 cuts uniquely in both plasmids at identical positions in the CMV promoter sequence. pCB6/intron has several unique endonuclease restriction sites for subcloning fragments downstream of the intron sequence and upstream of the hGH PolyA sequence (5'-XbaI/KpnI/MluI/ClaI/BspDI/XbaIlBamHI-3'). The neomycin resistance gene is transcribed using the SV40 promoter from an independent transcriptional unit encoded on the plasmid (Brewer, 1994).

Human insulin expression plasmid. A human insulin cDNA contained on a 515 base EcoRI fragment (SEQ ID NO: 1, Bell et al., 1979) was ligated into the EcoRI site of pBluescript (Stratagene, Inc., La Jolla, Calif.), generating pBS/INS. pBS/INS was digested with HinDIII, located 5' of the insulin open reading frame, and BamHI, located 3' of the Insulin open reading frame. The resulting 542 base fragment was ligated into pCB6 that had been restricted with HinDIII and BamHI, generating pCB6/INS. Stable transfectants from this plasmid are selected in G418. The same 542 base HinDIII/BamHI fragment was also ligated into HinDIII/BamHI digested pCB7 generating pCB7/INS. Stable transfectants from this plasmid are selected in hygromycin.

Second and third insulin expression plasmids were also constructed. pCB6/INS was digested with BglII and BamHI and the resulting 549 base fragment containing the human insulin cDNA (SEQ ID NO: 1) was ligated into the BamHI site pCMV8IRES/NEO/hGH PolyA and pCMV8/IRES/PURO/hGH PolyA, generating pCMV8/INS/IRES/NEO and pCMV8/INS/IRES/PURO, respectively. The CMV promoter drives transcription of a bicystronic massager RNA with human insulin encoded in the upstream open reading frame and the neomycin resistance gene encoded in the downstream open reading frame. Stable transfectants from this plasmid are selected in G418.

Alternative promoterlenhancers utilized in human insulin expression plasmids. The rat insulin 1 promoter fragment was isolated from pAC/RIP (a derivative of pACCMV.pLpA in which the rat insulin 1 promoter was substituted for the CMV promoter, Becker et al., 1994) as a KpnI/HinDIII fragment (SEQ ID NO: 12) corresponding to bases −412 to +1 relative to the start site of transcription. This fragment was ligated into KpnI/HinDIII digested pBlueScript (Stratagene, Inc.), generating pBS/RIP.pBS/RIP was digested with KpnI, treated with Klenow fragment to blunt the end, then digested with EcoRI, generating a 450 base pair fragment containing the rat insulin 1 promoter. This fragment was ligated into pCMV8/INS/IRES/NEO that had been previously digested with SpeI, treated with Klenow and then digested with EcoRI, generating pRIP8/INS/IRES/NEO.

The rat insulin I promoter fragment (441 base pair KpnI/HinDIII fragment, SEQ ID NO: 12) was also ligated into both KpnI and HinDIII digested pCB6/INS and pCB7/INS generating pCB6/RIP.INS and pCB7/RIP.INS, respectively. The CMV promoter fragment of both of these plasmids was removed by digesting with SpeI and BgMII (removing bases −585 to +1 of the CMV promoter), treating with Klenow fragment and ligating to close, generating pRIP6/INS and pRIP7/INS. Stable transformants of pRIP6/INS are selected in G418 while stable transformants of pRIP7/INS are selected in hygromycin.

The rat insulin 1 gene promoter fragment (RIP) was also modified in an attempt to strengthen its transcriptional activity. The principal modification involved the attachment of varying numbers of mutant Far-FLAT minienhancers (FFE minienhancer) (German, et al., 1992) to different positions within an intact RIP or to a RIP truncated at −205 (−205RIP). FFE minienhancers were constructed by generating oligonucleotides corresponding to the region of RIP between −247 and −196 (top strand, 5'-GATCCCTTCATCAGGCCATCTGGCCCCTTGTTA ATAATCGACTGACCCTAGGTCTAA-3' SEQ ID NO:29; bottom strand, 5'-GATCTTAGACCTAGGGTCA GTCGAT-TATTAACAAGGGGCCAGATGGCCTGATGAAGG-3', SEQ ID NO:30). The underlined sequences at the ends of the oligonucleotides are BamHI and BglII recognition sites. The oligonucleotides were annealed and ligated in the presence of restriction enzymes BamHI and BglII. Since BamHI and BglII produce compatible DNA ends but can no longer be digested by BamHI or BglII, the only multimers that escaped BamHI and BglII digestion were ligated head-to-tail. FFE minienhancer dimers, trimers, etc. were separated by polyacrylamide gel electrophoresis and blunt-end cloned into the transient transfection vector, pBS/RIP/hGH, at either a XhoI site immediately upstream of −415 of the intact RIP, into an AvrII site at −206 of an intact RIP, or into an ApaI site immediately upstream of −205RIP. The number and orientation of FFE minienhancer repeats were verified by DNA sequencing. The stable transfection vector, pFFE3/RIP8/INS/IRES/NEO containing three copies of FFE minienhancers (FFE3, SEQ ID NO:15), was generated by inserting a blunt-ended KpnI/HindIII FFE3/RIP into pCMV8/INS/IRES/NEO in which the CMV promoter was removed with SpeI and SacI. pFFE6/RIP8/INS/IRES/NEO was constructed by inserting an ApaI/blunt-endedHindIII FFE6/RIP fragment into pRIP8/hGH polyA in which RIP was removed by ApaI/EcoRV. A BglII/StuI INS/IRES/NEO fragment was then inserted into pFFE6/RIP8/hGH polyA to complete pFFE6/RIP8/INS/IRES/NEO.

The rat insulin 1 gene intron (RIPi) was obtained by polymerase chain reaction from rat genomic DNA using oli0onucleotides CTCCCAAGCTTAAGTGACCAGCTACAA, SEQ ID NO:31 and GGGCAACCTAGGTACTGGACCTTCTATC, SEQ ID NO:32. These oligos produced a 185 bp product containing the 119 base pair RIPi (Cordell et al., 1979) and a HindIII site on the 5'-end and a BamHI site on the 3'-end. The PCR™ product was digested with HinDIII and BamHI and ligated into pNoTA/T7, whereupon it was removed with XbaI blunt-ended with Klenow, treated with HinDIII and inserted into EcoRV/HinDIII digested pRIP8/INS/IRES/NEO to generate pRIP8/RIPi/INS/IRES/NEO. pFFE6/RIP8/RIPi/INS/IRES/NEO was constructed by replacing the 5' adenovirus-immunoglobulin hybrid intron/INS/IRES of pFFE6/RIP8/INS/IRES/NEO with RIPi/INS/IRES from pRIP8/RIPi/INS/IRES/NEO. p(RIE)3/-85RIP/RIPi/INS/IRES/NEO contained three copies of the rat insulin 1 gene enhancer (RIE) fused to RIP truncated at −85. This plasmid was constructed by replacing a BsgRI/HinDIII RIP fragment from pRIP8/RIPi/INS/IRES/NEO with an ApaI/HinDIII (RIE)3-85RIP fragment. Both the BsgRI and ApaI restriction sites were blunt-ended by Klenow polymerase.

The 2,000 base pair Class III human insulin-linked polymorphic region (ILPR), a region demonstrated to enhance transcriptional activity of the human insulin promoter (Kennedy et al., 1995), was obtained from the phage lambda clone 1-H1-3 (Owerbach and Aagard, 1984). A PstI/NcoI fragment containing the ILPR was treated with Klenow and inserted into a blunt-ended boI site immediately upstream of RIP to make pILPR/RIP8/INS/IRES/NEO. Orientation of the 14 bp repeats in the ILPR with respect to RIP was determined by DNA sequencing.

The human glyceraldehyde-3-phosphate dehydrogenase promoter (GAPDH) was isolated by the polymerase chain reaction from human genomic DNA using oligos (GGGTCTAGAGGACCTGTTCCCACCG, SEQ ID NO:33 and GCCGAATTCGAGGAGCAGAGAGCGAAGC, SEQ ID NO:34). These oligos generated a 1143 base product corresponding to bases −1121 to +22 of the published sequence (Ercolani et al., 1988) with the introduction of a unique XbaI site at the 5' end and a unique EcoRI site at the 3' end. The PCR™ product was digested with PstI (located at position −735 relative to start site of transcription), treated with Klenow, and then digested with EcoRI. The resulting 757 base fragment was ligated into pCMV8/INS/IRES/NEO that had been previously digested with SpeI, treated with Klenow and then digested with EcoRI, generating pGAPDH8/INS/IRES/NEO.

The Rous Sarcoma Virus Long Terminal Repeat (RSV) was isolated from pREP4 (Invitrogen, Inc., San Diego, Calif.). A 637 base pair SalI/PvuII fragment containing RSV was isolated, treated with Klenow to blunt the ends and ligated into pCMV8/INS/IRES/NEO that had been previously digested with SpeI and EcoRI and treated with Klenow, generating pRSV8/INS/IRES/NEO.

Bioreactor Inoculation and Culture. EP18/3E1 cells were grown, split, and maintained in RPMI-1640 medium with 2 mM glutamine (JRH Bioscience, Lenexa, Kans.) supplemented with 5% fetal calf serum (JRH) and 0.125 $\mu$g/ml G418 (Gibco BRL, Gaithersburg, Md.) in T75 culture flasks as described previously. A large scale bioreactor (Celligen Plus™, New Brunswick Scientific (NBS), Edison, N.J.) with dissolved oxygen electrode, pH electrode (both Ingold), and 4-gas proportional-integral-derivative (P-I-D) controller is set up for perfusion culture with a packed bed of polyester discs (Fibra-Cel®, Sterilin, England) and a centrifugal lift impeller (Cell Lift™, NBS). The reactor has a working volume of 1.25 liters and a packed bed volume of 0.7 liters containing 70 grams of polyester discs. Cells are trypsinized and seeded into the reactor containing the same media composition as the maintenance media at a density of approximately $10^6$ cells per ml of working volume. After transfer, the cells are allowed to seed onto the bed material for 8 h with a low impeller speed of 50 rpm and no media perfusion. After seeding, the impeller speed is brought up to 80 rpm and the culture is maintained with no perfusion for approximately 75 hours. Media perfusion is started and the flow rate is brought from 0 working volumes per day (WV/d) to 4 WV/d over the course of the following 500 hours. The perfusion rate is thereafter maintained constant at 4 WV/d. The perfusion media is RPMI-1640 with 2 mM glutamine which is then supplemented with 2 g/l glucose (final concentration of 4 g/l), 0.10% fraction V bovine serum albumin, 10 $\mu$g/ml human apo-transferrin, 50 $\mu$M each of ethanolamine and o-phosphorylethanolamine, and 0.10% cholesterol rich lipids from adult bovine serum (Clark and Chick, 1990) (all Sigma Chemicals, St. Louis, Mo.). The perfusion media contains no fetal calf serum or other full sera. At approximately 600 hours of culture, the media was further enriched with glucose to a final concentration of 6 g/l. The impeller speed was increased to 100 rpm after 200 hours of culture, to 120 rpm after 300 hours, and to 150 rpm after 700 hours. The culture temperature is maintained at 37° C., the dissolved oxygen level at 80% (indexed relative to saturation of air in 37° C. phosphate-buffered saline), and the pH at 7.4. Glucose levels in the reactor are maintained in the range of 1–3 g/l by adjusting the perfusion rate and the glucose concentration in the fresh perfusion media. Cultures have been maintained successfully for as long as 2000 hours in the bioreactor under similar conditions.

Media samples were collected once daily and quantitatively analyzed for insulin secreted into the media by ELISA as previously described. Selected samples were qualitatively analyzed for insulin processing by HPLC analysis as previously described. Ammonia and lactate levels are monitored in the daily samples and analyzed using an automated analyzer (IBI Biolyzer, Johnson & Johnson, New Brunswick, N.J.).

At the end of the culture, the reactor is opened and a representative number of polyester discs are sampled for quantitation of DNA and insulin content.

Cyclically Stimulated Secretion in the Bioreactor. At a point during the culture when the oxygen controller output has stabilized around 60, the culture is cyclically stimulated with addition of a 10X concentrated secretion-stimulation cocktail once every 24 hours. The addition of the cocktail yields final medium concentrations of 10 mM each of leucine, argine, and glutamine, 100 $\mu$M IBMX, and 100 $\mu$M carbachol (all from Sigma). At the beginning of every cycle, approximately one-tenth of the working volume is replaced with the 10X cocktail while the perfusion of fresh media is left unchanged. At 4 l/d of perfusion, e.g., the remaining concentration of cocktail after 24 h is less than 2% relative to the initial concentration due to the continuous dilution by the perfusion. Six samples were taken every 30 minutes, then four samples every hour.

Stable transfection of cell lines. Cells were transfected by electroporation as described above for the Hexokinase 1 knockout electroporations.

Insulin message primer extension analysis. Total RNA from RIN cell lines grown in vitro was isolated using RNAzol B RNA Isolation Reagent (Cinna/Biotex Laboratories Int.). Total RNA from RIN cell lines grown in vivo as tumors was isolated using TriReagent (Molecular Research Center, Inc.). Ten $\mu$g total RNA was hybridized to a 5' digoxigenin-labeled oligo (GC-CAGCAGGGGCAGGAGGCGCATCCACAGGGCCAT, SEQ ID NO:35, Genosys Biotechnologies, Inc.) in 0.25 M KCl at 68° C. for 15 min. This oligo hybridizes to the first 35 bases of the endogenous rat insulin I as well as the human insulin open reading frames. Primer extension reactions were then carried out with 2.5 units AMV Reverse Transcriptase in the supplied buffer (Promega, Inc.) supplemented with 0.8 mM dNTP's (Pharmacia, Inc.) and 100 $\mu$g/ml Actinomycin D (Sigma Chemical Co.) at 42° C. for one hour. Extension products were precipitated, resuspended in 40% water/60% Formamide, heated to 100° C. for 5 min and run on a 8% acrylamide/7M urea/1X TBE denaturing gel. Electrophoresed products were transferred to Qiabrane Uncharged Nylon Membrane (Qiagen, Inc.) using a Transphor Unit, TE50X (Hoefer, Inc., San Francisco, Calif.). Digoxigenin-labeled products were detected using the Genius 7 Non radioactive Detection System (Boehringer Mannheim) followed by exposure to Xomat-AR auto radiography film (Kodak). Primer extension of endogenous rat insulin I message generates a 91 base product (Cordell et al., 1979), the human insulin transgene expressed from pCB6 generates a 101 base product and the human insulin transgene expressed from pRIP7 generates a 68 base product. Primer extension of the human insulin transgene expressed from pCMV8/INS/IRES/NEO generates a primary signal of 280 bases with three other minor premature termination signals of approximately 190, 130 and 115 bases.

Northern analysis. Total RNA was isolated as described above for the primer extension protocol. Ten $\mu$g total RNA was resolved on methyl mercury/ 1.5% agarose gels as described (Bailey and Davidson, 1976). Gels were subsequently stained with ethidium bromide (1 $\mu$g/ml in 0.5 M ammonium carbonate) to visualize RNA for integrity and loading consistency. RNA was electro transferred to nylon membranes as described for the primer extension protocol. Membranes were hybridized with digoxigenin-labeled RNA probes using the Genius Non-Radioactive Nucleic Acid Labeling and Detection System for filter hybridizations as described (Boehringer Mannheim). Full-length digoxigenin-labeled antisense probes corresponding to human insulin, rat glyceraldehyde 3-phosphate dehydrogenase (GAPDH) (corresponding to bases 21 to 1162 of published sequence, Fort et al., 1985) and the neomycin resistance gene (control template supplied in Genius 4 Kit) were made using Genius 4 RNA Labeling Kit (Boehringer Mannheim) using either T7 or T3 Polymerase. Exposures of chemiluminescent detected membranes were performed using Xomat-AR autoradiography film (Kodak). In some cases, blots were hybridized with a $^{32}$P-labeled cRNA probe for human insulin.

Stimulated insulin secretion assay. Four million RIN cells were seeded in 9 ml media in 25 cm$^2$ flasks (butyrate-treated cells were seeded at 10$^6$ cells). Cells were then cultured with daily media changes for one week with or without 1 mM butyrate until cells reached 70–80% confluency. Prior to assay, cells were incubated 2 times for twenty minutes at 37° C. in RPMI media lacking glucose and supplemented with 0.1% BSA and 20 mM HEPES, pH 7.2. The basal incubation of cells was for 1 h at 37° C. in 4 ml RPMI containing 0 mM glucose, 0.1% BSA, 20 mM HEPES and 100 $\mu$M diazoxide (Sigma Chemical Co.). Basal secretion samples were collected and aliquotted for insulin immunoassays and HPLC analysis of insulin species. This was followed by the stimulated incubation of cells for 1 hour at 37° C. in 4 ml RPMI with 5 mM glucose, 0.1% BSA, 20 mM HEPES, 10 mM each leucine, arginine and glutamine, 100 $\mu$M carbachol (Sigma Chemical Co.) and 100 $\mu$M IBMX. Stimulated secretion samples were then collected and aliquotted. Cells were returned to a basal incubation for 1 hour at 37° C. in 4 ml RPMI containing 0 mM glucose, 0.1% BSA, 20 mM HEPES and 100 $\mu$M diazoxide.

Cells were then collected for determination of insulin content and cell number by addition of EDTA to the media to a final concentration of 2 mM and pipetting up and down to remove cells. Twenty percent of the cell suspension was taken for determination of DNA content. The remainder of the sample was centrifuged at 220×g for 5 minutes to pellet the cells. The cell pellet was resuspended in 0.5 ml cold 0.1 M acetic acid/0.1% BSA and sonicated on ice (Setting 2, Sonic Dismembranator 50, Fisher Scientific, Pittsburgh, Pa.). The sonicate was aliquotted for insulin immunoassays and HPLC analysis of insulin species.

Determination of DNA content and cell number. RIN cells are pelleted and PBS removed. 0.5 ml of DNA extraction buffer (2.0 M NaCl, 2.0 mM EDTA, 40 mM Phosphate buffer, pH 7.4) is added to RIN samples and the RIN cells are sonicated, on ice, for 30 seconds at ~30% power (Fisher 50 watt sonicator). Four microliters of sonicate are then diluted into 1 ml fresh DNA assay dye solution (TNE - 10 mM Tris, 1 mM EDTA, 0.1 M NaCl, pH 7.4, containing 0.1 µg/ml Hoechst dye 33258 (Polysciences or Molecular Probes), with calf thymus DNA as a standard (Clontech Inc.). Samples are read using a DNA fluorimeter (Hoeffer Scientific Instruments, Model TKO100). Six Pg genomic DNA per $10^6$ cells was used for the conversion from DNA content to cell number values.

HPLC analysis of insulin processing intermediates. Acid/ethanol extracts of whole cells or conditioned media was prepared and analyzed by high performance liquid chromatography as described (Halban et al., 1986, Sizonenko and Halban, 1991). Immunoreactive insulin (IRI) species were quantitated by radioimmunoassay as described (Halban et al., 1986).

Tumor formation of transfected RIN cell lines in nude rats. Six to 8 week old athymic Fisher nude rats (Strain F344/Ncr-rnu from National Cancer Institute, Fredrick, Md.) were housed in a sterile isolation facility with free access to sterile standard laboratory chow and water. Three million cells were injected subcutaneously at two different locations in 100 µl PBS using a 1.0 cc U-100 insulin syringe (Bectin Dickenson). Tumors were excised once they were palpable, excess fat and associated tissue dissected away. Samples frozen prior to processing. Body weight and bleeds for blood glucose determination were taken prior to injecting cells and throughout the course of the experiment. Blood glucose was measured using an IBI Biolyzer (Kodak, Eastman Chemical Co.).

Results

Rat insulinoma cells have been engineered to produce high levels of human insulin. The RIN cell line was derived from a radiation-induced tumor (Gazdar et al., 1980). The insulin secretory characteristics of the parental cells used in these studies, RIN 1046-38, have been described and shown to exhibit abnormal sensitivity to glucose (Clark et al., 1990 and Ferber et al., 1994). These cells secrete insulin at glucose concentrations of 50 µM, secreting 2–10 ng rat insulin/million cells/hour. This level of insulin is well below levels produced by primary rat or human islets (Rhodes and Halban, 1988 and Marchetti et al., 1994) or other reported rodent insulinoma lines (Asafari et al., 1992, Knaack et al., 1994). RIN 1046-38 cells were stably transfected with an expression plasmid containing a human insulin cDNA driven by the human cytomegalovirus promoter (pCB6/INS). One clone, R5C.I-17, was selected based on high insulin secretion and further characterized. FIG. 4A. shows the total immunoreactive insulin content as measured by RIA of R5C.I-17 versus the parental RIN cell line. R5C.I-17 has a total insulin content of 450 ng per million cells, 3-fold above parental RIN.

Chronic culture of rat insulinoma cells in sodium butyrate has been shown to increase endogenous insulin message, content and secretion (Swarovsky et al., 1994). To determine if similar increases would result from a human insulin transgene in rat insulinoma cells, R5C.I-17 cells were cultured for 7 days in 1.0 mM sodium butyrate. Cell growth was retarded but continued over the course of the week. Insulin content was determined at the end of the week and showed a 3-fold increase per cell above the untreated cells (FIG. 4A), consistent with data on the increase in content of endogenous insulin (Swarovsky et al., 1994). This higher level of human insulin content suggests that the RIN 1046-38 cells are capable of synthesizing and storing more human insulin. Sodium butyrate treatment to transiently induce insulin production in the large scale bioreactor.

To increase the level of production of human insulin, R5C.I-17 cells were stably transfected a second time with pRIP7/INS. This expression plasmid utilizes the rat insulin 1 promoter driving expression of human insulin. EP11.3E9 was identified based on an increased insulin production above R5C.I-17 and characterized further. The insulin content of EP11.3E9 is 1400 ng per million cells, four times higher than its parent, R5C.I-17 or RIN (FIG. 4A).

Human insulin, like endogenous rat insulin, is secreted via the regulated pathway in the engineered RIN cell lines. Insulin secretion values for a one hour pre-incubation in buffer alone (basal values) followed by a one hour incubation in a cocktail of IBMX, glucose and amino acids (stimulated levels) are shown in FIG. 4B. Low basal insulin secretion is seen from R5C.I-17 and EP11/3E9, even with the human insulin transgene constitutively expressed by the CMV promoter. A higher basal secretion is seen from the butyrate-treated R5C.I-17 cells. However, in all lines, insulin release was significantly increased following stimulation to levels of 150, 425 and 450 ng per million cells per hour from R5C.I-17, butyrate-treated R5C.I-17 and EP11/3E9, respectively. Stimulated insulin release per hour ranges from 25 to 35% of the intracellular stores for all four RIN lines, a value consistent with primary islet data (Curry, 1986 and Li et al., 1994). R5C.I-17 has maintained its insulin output through more than 100 population doublings without drug selection (approximately one year in culture).

Results from transgenic animals (Schnetzler et al., 1993) and from cell lines (Halban and Wollheim, 1980) have supported the idea of a physiological set point for insulin production in β-cells. However, a threshold or upper limit on insulin production in the current engineered RIN cells has not been observed.

Human proinsulin is efficiently processed to mature insulin by rat insulinoma cells. Intracellular insulin species were isolated from parental RIN, R5C.I-17 and EP11/3E9 cells by acid extraction. Separation by HPLC of the insulin species produced by these cells was done as described (Halban et al., 1986, Sizonenko and Halban, 1991). The analysis indicates that human insulin produced by the rat insulinoma is efficiently processed to mature insulin with very low detectable levels of pro-insulin or other processing intermediates (FIG. 5A, FIG. 5B, FIG. 5C). Processing of human insulin is slightly less efficient compared to the processing of rat insulin at these levels of production. While the percentage of intracellular rat proinsulin and intermediates is 3 to 4% of total rat insulin in all cell lines examined, the percentage of intracellular human proinsulin and intermediates is 8% in R5C.I-17 and approaches 18% in EP11/3E9. The ability of RIN cell lines to efficiently process proinsulin to mature insulin in these engineered lines demonstrates the maintenance of the high levels of expression of the endoproteases PC2 and PC3, known to be responsible for insulin processing (Vollenweider et al., 1995). This is an important feature of the RIN cell lines being developed.

Expression of human insulin transgene is stable in vivo. RIN cells injected subcutaneously into a nude rat will form tumors. These tumors can then be excised and analyzed for gene expression. As has been seen previously, the majority of the tumor mass is RIN cell in origin with only small numbers of cells being host-derived in the form of endothelium, fibroblasts, etc. (Schnedl et al., 1994). This allows for a convenient model for analysis of both endogenous and transgene expression in RIN cells in vivo. In the absence of any restraint of tumor growth, time points are restricted to one to two months because RIN cells secrete increasing amounts of rat, and in our studies human insulin, leading to hypoglycemia. Blood glucose levels were monitored throughout the course of the experiment.

One and a half million R5C.I-17 cells were injected subcutaneously at two sites per animal. The animals quickly become hypoglycemic in 8 to 10 days following this dose of cells (FIG. 6). Following the onset of hypoglycemia, animals are maintained on glucose in their drinking water as well as IP glucose injections prior to surgery. One animal demonstrated a blood glucose rebound following removal of both tumors. This rebound after two days of exogenous insulin-induced hypoglycemia is followed by the rapid removal of the exogenous insulin source.

Nine tumor masses in all were isolated from four animals between days 13 and 31. These tumors ranged in size from 40 to 200 mg in wet weight. RNA was isolated from tumors and expression of several gene products was analyzed and compared to uninjected cells maintained in tissue culture (in vitro). Primer extension analysis was used to compare the rat and human insulin signals in the same samples. The same primer hybridizes efficiently to both messages, but upon primer extension gives two different size products which can easily be resolved and quantitated. The results of this analysis are shown in FIG. 7. The same amount of starting RNA was used in each reaction from either cells maintained in vitro or from tumors, but contamination of non-RIN cells may cause the rat and human insulin signals to be underrepresented in the tumor samples. No attempt was made to correct for this. The signal for the human insulin transgene driven by the CMV promoter was very constant throughout the time points examined. No diminution of signal was apparent, suggesting the in vivo environment had no deleterious effects over the course of this experiment. Subsequent experiments have analyzed tumors at time points of 48 days (versus 31 days here) with no diminution in CMV driven/human insulin transgene expression.

To further test the stability of the CMV driven transgenes in vivo, engineered RIN cells were implanted into nude rats and transgene expression assessed with time. Several independent cell lines were implanted into multiple animals, expressing at least three different transgenes. The use of independent cell lines with different integration sites should give an unbiased answer to the issue of CMV promoter stability in RIN cells in this particular model. Longer time points of 48 days have been analyzed with no reduction in CMV driven expression. The in vivo model of implanting RIN cells into nude rats is limited by the uncontrolled growth of the RIN cells as a tumor. All the RIN lines used here make endogenous rat insulin, with some also making human insulin so that the animals quickly become hypoglycemic. Efforts were made to maintain the animals blood glucose by administering glucose in the drinking water or by i.p. injections, allowing analysis of tumors at longer time points. Alternatively, lower doses of cells can be injected initially ($3 \times 10^5$ rather than $3 \times 10^6$) which is how a 48-day tumor was generated and analyzed for maintenance of gene expression. Unfortunately, this lower dose of injected cells leads to a more sporadic tumor growth, making it harder to generate samples for analysis.

Surprisingly, endogenous insulin expression increased in all nine in vivo samples examined. This was unexpected since all nine tumors were excised following periods of extreme hypoglycemia, conditions known to down regulate pancreatic β-cell insulin message (Giddings et al., 1982 and Brunstedt and Chan, 1982). Comparison of the ratio of rat to human insulin signals changed from 0.73+/−0.6 for several in vitro samples to 1.87+/−0.17 for the nine tumor samples. The 0.73 in vitro ratio correlates very well with the ratio of rat to human insulin (1 part rat to 1.5 parts human) observed for the R5C.I-17 cell line (see FIG. 5 for mass ratios). The increased rat to human message signal in tumors is paralleled by an increased rat to human insulin content in tumors subjected to acid extraction and HPLC separation of the insulin species.

A similar result was obtained following injection of the high human insulin producing cell line, EP11/3E9, into nude rats. Animals became hypoglycemic while maintaining body weight over the course of the experiment (FIG. 6). Nine tumors were isolated between days 15 and 28 following injection. Primer extension analysis of RNA isolated from the tumors allows for separation of three insulin messages in the EP11/3E9 line. Extension of the endogenous rat insulin message and the human insulin message driven by the CMV promoter produced the identical pattern as seen in R5C.I-17, the parent cell line to EP11/3E9. A third extension product results from expression of the human insulin transgene message by the rat insulin 1 promoter. Primer extension analysis on the tumor samples as well as the cell lines maintained in vitro show human insulin driven by the CMV promoter is stable throughout the course of the in vivo experiment. Again, endogenous rat insulin is upregulated in the in vivo environment, even in the face of hypoglycemia. The human insulin transgene driven by the rat insulin promoter is expressed throughout the course of the in vivo experiment.

In vivo potency of engineered RIN cell lines. When the engineered RIN lines are growing as tumors in the nude rats, their secreted insulin eventually impacts on the blood glucose levels of the healthy animals causing hypoglycemia (FIG. 6). While parental RIN cells have endogenous rat insulin outputs that eventually lead to hypoglycemia, RIN cells engineered to overexpress human insulin should induce hypoglycemia either faster with the same number of cells or require a smaller tumor mass. We measured the tumor mass needed to induce the initial hypoglycemia in a nude rat as an indicator of in vivo potency of the engineered RIN cells.

Tumors were removed from the nude rats injected with either the R5C.I-17, EP11/3E9 or parental RIN 1046-38 at the first sign of hypoglycemia. The time between injection of a constant number of cells to hypoglycemia varied from 12 to 13 days for R5C.I-17 and EP11/3E9 (FIG. 6) to 28 days for the parental cells. All of the lines grow at the same rates in vitro. A plot of the tumor mass versus the in vitro stimulated insulin secretion values for these lines (FIG. 4B) is shown in FIG. 8. The higher the in vitro insulin output (both rat and human insulin), the smaller the tumor mass needed to cause hypoglycemia.

Endogenous GLUT-2 expression in RIN cells is lost in vivo. The expression of several other genes in the tumor samples was analyzed and compared to RIN cells maintained in vitro. The results of the analysis of both endogenous genes and introduced transgenes is shown in FIG. 9. RNA from two independent tumor samples from day 24 and day 25 were combined (in vivo sample) and compared to RNA from R5C.I-17 cells maintained in tissue culture (in vitro sample). Message levels of endogenous glucokinase, hexokinase I, amylin, GAPDH, sulfonylurea receptor and IPF1, as well as message levels of human insulin and the neomycin resistance transgenes, were relatively unchanged following 24 to 25 days of in vivo passage of R5C.I-17 cells. In contrast, the message level of endogenous GLUT-2 detected in R5C.I-17 cells maintained in vitro is completely absent in tumors at the 24/25 day time point. This result was duplicated on a separate analysis for confirmation (GLUT-2 a and b, FIG. 9). Analysis of individual tumors from day 13 through day 31 demonstrated expression of GLUT-2 was already absent at the earliest time point analyzed and remained absent throughout the remainder of the experiment.

Loss of in vivo GLUT-2 expression could have serious consequences for the performance of cell lines designed for insulin delivery to animals or patients with diabetes. Stable transfection of insulin producing cell lines with the GLUT-2 cDNA has been shown to confer glucose-stimulated insulin secretion (GSIS), while transfection of the same cells with a related transporter, GLUT-1, has no such effect (Hughes et al., 1992, 1993; Ferber et al., 1994; U.S. Pat. No. 5,427,940). Furthermore, loss of GLUT-2 expression has been documented in a large number of rodent models of type II diabetes (NIDDM) in which β-cell failure involving loss of GSIS is a cause of hyperglycemia (Johnson et al., 1990; Orci et al., 1990; Thorens et al., 1990; Unger, 1991). Endogenous GLUT-2 expression is apparently down-regulated or extinguished under diverse physiological conditions. In addition to the studies cited above, in which animals were hypoglycemic, implantation of normal islets from db/- mice into diabetic, hyperinsulinemic db/db mice or db/- mice rendered diabetic and hypoinsulinemic by injection of the β-cell cytotoxin, streptozotocin, resulted in loss of GLUT-2 expression in the transplanted islets (Thorens, 1992b). These results suggest that loss of GLUT-2 may also be responsible for impaired glucose responsive insulin release in human islets transplanted into patients with Type I or II diabetes (Scharp et al., 1994). Reduced GLUT-2 suppression in the face of hyperglycemia is surprising in light of recent studies demonstrating that the GLUT-2 promoter is activated by glucose in hepatocytes or the insulinoma cell line INS-1 (Waeber et al., 1994). Overall, these studies strongly imply that the GLUT-2 promoter is adversely effected by various metabolic perturbations in vivo, and that this promoter element is not appropriate for use in directing stable expression of heterologous genes in cell lines.

FIG. 10 illustrates that GLUT-2 expression can, in fact, be maintained in RIN cells implanted into nude rats for relatively prolonged periods of time if the gene is stably transfected under the control of a viral promoter such as CMV. A RIN 1046-38 clone expressing high levels of rat GLUT-2 driven by the CMV promoter was generated using pCB7/GLUT-2 (clone EP49/206) as previously described (Ferber et al., 1994). Animals injected with RIN EP49/206 form solid tumors and become hypoglycemic, much as reported for animals receiving cells containing only the endogenous GLUT-2 gene. Unlike the untransfected cells, however, GLUT-2 mRNA levels are maintained at a high, constant level over the two time points sampled, 16 and 34 days (FIG. 10A). These particular cells also were stably transfected with plasmids containing the human insulin and glucokinase cDNAs under control of CMV, and transcript levels for these other transgenes were maintained in a stable fashion, analogous to GLUT-2. These results indicate that cell lines transfected with multiple genes under control of a strong viral promoter like CMV are able to maintain stable expression of all transgenes for prolonged periods of time when transplanted into animals. These results are surprising and would not have been expected in light of previous studies from other groups who have reported that strong viral promoters such as CMV or RSV are often down-regulated in the in vivo environment (Palmer et al., 1989 and 1991, Scharfmann et al., 1991, Challita and Kohn, 1994).

Increased insulin production using expression plasmids containing an internal ribosome binding site. A new insulin expression plasmid was designed that links the expression of the drug selection marker to the expression of insulin. The plasmid, pCMV8/INS/IRES/NEO, utilizes the CMV promoter to drive a bicistronic message containing the human insulin open reading frame upstream of the neomycin resistance open reading frame. Placed between the two reading frames is a portion of the 5'-transcribed leader of the gene encoding human Glucose Regulated Protein 78 (GRP78; Ting and Lee, 1988). The 5'-leader of human GRP 78 has been shown to direct internal initiation of translation (Internal Ribosome Entry Site, IRES) allowing for construction of functional polycistronic genes in mammalian cells (Macejak and Sarnow, 1991). In order to generate Neo-resistant cells with this plasmid, the human insulin message must also be present, increasing the number of RIN clones that express human insulin protein. Since internal initiation of translation by IRES elements is less efficient than normal 5' cap-dependent initiation (Macejak and Sarnow, 1991), cells must express high levels of the bicistronic transgene in order to survive drug selection. In this way, it should be possible to directly select with G418 clones expressing high levels of human insulin.

Twenty-nine independent G418 resistant clones from an electroporation of parental RIN 1046-38 cells with pCMV8/INS/IRES/NEO were screened for insulin content following acid extraction as described. The results are shown in FIG. 11 with the insulin content of R5C.I-17 (450 ng/million cells, FIG. 4A) used for comparison. Twenty-nine out of 29 clones expressed detectable levels of human insulin with at least 10 out of 29 of the clones (34%) expressing levels of human insulin more than 2-times that of R5C.I-17. RNA was isolated from the 5 highest insulin producing clones and human insulin message analyzed using primer extension. Starting inputs of 10 and 3 μg of RNA from these 5 clones, as well as from a polyclone from this electroporation, were compared to 10 μg of RNA from R5C.I-17. In the 5 monoclones as well as the polyclone, high levels of human insulin message were detected at the expected size of 280 base pairs with three other minor premature termination signals of approximately 190, 130 and 115 bases. Even with 3 μg of input RNA, the human insulin signal is still comparable to the signal from 10 μg of RNA from R5C.I-17, a level of human insulin message in these clones in line with the higher levels of insulin protein.

One clone, EP18/3E1 has been further characterized. The insulin content of EP18/3E1 is 1300 ng per million cells with a stimulated insulin secretion rate of 500 ng/million cells/ hour. These levels of insulin are comparable to those achieved in EP11/3E9. our highest insulin producing clone to date (FIG. 4). However, in contrast to previous insulin producing clones, EP18/3E1 and other high insulin producing clones (FIG. 11) were generated from one round of electroporation using a single expression plasmid. The utility of the expression plasmid pCMV8/INS/IRES/NEO is in both the high numbers of positive clones and the higher insulin outputs of individual clones. Also, only one drug selection marker was used as opposed to two in generating EP11/3E9.

Introduction of a second human insulin trangene into R5C.I-17 cells produced 11/3E9, a cell line with higher insulin production. Similarly, a second insulin construct was expressed in 18/3E1 cells to produce clones with increased insulin output. The construct consists of the human insulin gene linked to the puromycin resistance gene and the transcription of the bicistronic message produced is controlled by the CMV promoter. Colonies of cells that grew after selection in 2 ug/ml of puromycin were screened for increased insulin output. FIG. 12A demonstrates the expression of human insulin RNA of both bicistronic transgenes, and the increased insulin content for 5 selected clones. The cell line EP111/220 exhibited the highest cellular insulin content (FIG. 12B) and secreted the most insulin. The EP111/220 clone when incubated with the stimulation cocktail of mixed nutrients and secretagogues (as for FIG. 5B) secreted 0.99 µg insulin/$10^6$ cells-hour. Currently, EP111/220 represents the highest documented insulin secretion of our cells engineered with human insulin.

The insulin content and secretory output of human islets may be estimated from reports in the literature. The average human pancreas contains about 0.9 g of islets (K. Saito et al., 1978) which equals $9 \times 10^8$ cells (Finegood et al., 1995), and the average human pancreas contains 200 U of insulin (with a 3-fold range; Wrenshall et al., 1952). Thus, when in situ, the insulin content of the average human islets approximately 0.22 U/$10^6$ cells, or 8 µg/$10^6$ cells. Freshly isolated human islets are reported (Eizirik et al., 1992 and 1994) to contain 8–10 µg/6 µg DNA (6 µg=$10^6$ cells). The same authors report that after one week of culture human islets contain 4–5 µg/6 µg DNA and with stimulation secrete 459 ng/6 µg DNA/h. Freshly isolated rat islets, for comparison, are reported to contain 4–8 µg insulin/6 µg DNA, and with stimulation secrete 0.2 to 2 µg insulin/6 µg DNA (Tokuyama et al., 1995; Rhodes and Halban, 1988; Nielsen, 1985). The functionally-normal mouse β-cell lines secrete 400–800 ng insulin/h upon stimulation, and contain 3–10 µg insulin/$10^6$ cells (Miyazaki et al., 1990; Radvanyi et al., 1993; Knaack et al., 1994). The values presented for human islet insulin content and secretion are expected to represent the higher end of the range, because human islets are known to be less potent than rodent islets, both in vitro (Smith et al., 1991) and in vivo (Jansson et al., 1995). The cell line EP111/220 has an insulin content that appears to be 60–75% of the value presented for cultured human islets, while insulin secretion appears to surpass that of cultured human islets.

The humanized β-cell lines generated in these studies exhibit a number of unique characteristics. First they express only one of the two rodent insulin genes (Fiedorek et al., 1990 and the inventors' data), which will be advantageous in knockout development of complete insulin-humanized β-cell lines. Second, the present engineered lines have the capability to increase insulin secretion 10- to 20-fold in response to stimuli. This characteristic is similar to that of β-cell lines derived from SV40-T antigen transgenic mice such as MIN6 (Miyazaki et al., 1990), and OHC (Radvanyi et al., 1993) cell lines as well as normal β-cells (Curry, 1986). Third, these cells maintain essentially normal processing of human proinsulin, even though the exogenous protein is in excess of endogenous rat protein. Normal processing is not present in INS-1 (Neerman-Arbez et al., 1993) and βTC cells (Nagamatsu and Steiner, 1992) two β-cell lines that have been examined for this property. Finally, the present cell lines demonstrate that iterative introduction of the insulin gene provides an approach whereby human insulin output can be stably achieved which (at minimum) matches that of cultured human islets.

Analysis of other promoter/enhancer elements for drivinu insulin expression. Several other enhancer/promoters were compared to the CMV enhancer/promoter for their ability to direct transcription of the same bicistronic message (5'-intron/hINScDNA/IRES/NEO/hGH/3'-polyA) in stably transfected RIN38 cells. These promoters include the rat insulin 1 gene promoter (RIP), modified RIP (FFE/RIP), RIP linked with the rat insulin 1 gene intron (RIP/RIPi) in place of the hybrid adenovirus/immunoglobulin 5'-intron, the Rous Sarcoma Virus Long Terminal Repeat (RSV), the human glyceraldehyde-3-phosphate dehydrogenase promoter (GAPDH), and the mouse metallothionein promoter (MT). Expression plasmids were constructed by removing the CMV promoter found in pCMV8/INS/IRES/NEO and replacing it with the promoter to be tested. In this way, message levels and insulin outputs from the RIN clones constructed with the various promoters can be compared directly.

RIP activity is approximately 30- to 50-fold lower than that of the CMV promoter in transiently transfected RIN38 cells. However, in stably transfected RIN38 cells, RIP activity is much closer to the activity of the CMV promoter. The level of human insulin (hINS) mRNA derived from pRIP8/hINS/IRES/NEO is, on average, approximately only 3- to 5-fold lower than levels obtained from stable RIN38 lines containing pCMV8/hINS/IRES/NEO. The Northern blot depicted in FIG. 13 demonstrates this result as the level of hINS mRNA from two pRIP8/hINS/IRES/NEO RIN lines, 2.18 and 2.38, is only 3-fold lower than the level of hINS MRNA from the pCMV8/hINS/IRES/NEO RIN line, EP18/3E1. As stated earlier, the EP18/3E1 line has a very high insulin content, approximately equivalent to that of a normal human β-cell. Therefore, in addition to the CMV promoter, RIP offers another choice as a strong transcriptional activator.

RIP also was modified in an attempt to make it an even stronger transcriptional activator. The principal modification made to RIP was the attachment of Far-FLAT mini-enhancers (FF mini-enhancer). The FF mini-enhancer is located between −247 and −198 of RIP and contains several cis-acting regulatory elements crucial for RIP activity in b cells (Karlsson et al., 1987; Karlsson et al., 1989). The FF mini-enhancer region contains both the Far box (−239 to −230) and the FLAT element (−222 to −208) which further consists of two adjacent regulatory motifs, FLAT F and FLAT E. When isolated from the rat insulin 1 gene promoter and multimerized to yield 5 linked copies, the FF mini-enhancer is almost as active as an intact RIP in transiently transfected β-cells (German et al., 1992). Three base changes in the FLAT E motif at positions −209, −211, and −213 can further increase the activity of the FF minienhancer (now called FFE minienhancer) approximately 3-fold in transiently transfected β-cells (German et al., 1992). A transient transfection system with RIN38 cells was set up for initial screening of modified RIP promoter/enhancers. Results from the transient transfections utilizing a human growth hormone (hGH) reporter gene demonstrated that two modified RIP enhancer/promoters were 5-fold more active than RIP. The two modified RIP enhancer/promoters consisted of an intact RIP (−415 to +1) to which either three or six copies of FFE minienhancers had been attached just upstream of −415 of RIP (the FFE sixmer is in the reverse orientation with respect to RIP). Coexpression of the RIP transcription factor, IPF-1, along with either pFFE3/RIP/hGH or pFFE6/RIP/hGH produced an 8-fold increase in activity over that of RIP alone.

To test whether or not the FFE-modified RIP enhancer/promoters would increase RIP activity in stably transfected RIN38 cells to the same extent as was demonstrated in transiently transfected RIN38 cells, FFE3/RIP was placed into the 5'-intron/hINScDNA/IRES/NEO/hGH/3'-polyA stable-transfection vector. A large number of RIN38 cell lines containing pFFE3/RIP8/INS/IRES/NEO were analyzed for FFE3/RIP activity. A number of clonal lines expressed higher human insulin mRNA than was observed for the best pRIP8/INS/IRES/NEO lines. Phosphoimager analysis of the Northern blot shown in FIG. 13 demonstrated that FFE3/RIP clones 4.17 and 4.32 produced approximately 2-fold more hINS than the highest-producing RIP lines 2.18 and 2.38. Therefore, these data demonstrate that RIP activity was enhanced in stable RIN lines by the addition of 3 FFE mini-enhancers, although not to the same extent as was shown in the transient transfection system. pFFE6/RIP8/INS/IRES/NEO is currently being introduced stably into RIN38 cells. Attempts to stably coexpress IPF-lare also underway and are discussed below.

A second modification to RIP occurred by placing the rat insulin 1 gene intron (RIPi) immediately downstream of the transcriptional start site. It was previously noted that RIP activity was significantly increased in transgenic mice and, to a lesser extent, in cultured β-cells when combined with RIPi. A large number of stable RIN38 lines transfected with pRIP8/RIPi/INS/IRES/NEO were established and examined for hINS MRNA levels. As was observed for the FFE3 minienhancer, on average, the addition of RIPi to RIP yielded a modest but significant increase in hINS MRNA levels. The RIP/RIPi line, 2.65, expressed a level of hINS mRNA equivalent to the CMV promoter line, 18/3E1, and three times more hINS mRNA than the 2.18 and 2.38 RIP lines (FIG. 13). Since the addition of either RIPi or the FFE mini-enhancers enhance RIP activity, then combining both RIPi and FFE mini-enhancers with RIP could result in an additive increase of overall RIP strength. To test this idea, pFFE6/RIP8/RIPi/INS/IRES/NEO has been constructed and transfected into RIN38 cells. p(RIE)3/-85RIP/RIPi/INS/IRES/NEO, a plasmid which contains both RIPi and three full-length rat insulin 1 gene enhancers instead of mini-enhancers, has also been constructed and transfected into RIN38 cells. Analysis of these cell lines will soon be underway.

Other RIP derivatives have either been constructed or are currently undergoing construction. These include pILPR/RIP8/INS/IRES/NEO and pRIP8(O2)7/RIPi/INS/IRES/NEO. The human Class III insulin-linked polymorphic region (ILPR) is composed of 139 tandemly-repeated 14 bp sequences and lies immediately upstream of the human insulin gene promoter/enhancer (Owerbach and Aagaard, 1984). It has recently been demonstrated that the presence of the Class III ILPR significantly increases the transcriptional activity of the human insulin promoter/enhancer (Kennedy et al., 1995). Likewise, fusing the Class III ILPR to RIP may also increase RIP activity. pRIP8(O2)7 is a RIP that has been altered by inserting seven copies of the operator site [(O2)7] from the *E. coli* tetracycline (tet)-resistance operon between the RIP enhancer and promoter at position -85. The tetracycline-resistance operon regulatory system (Gossen and Bujard, 1992) is a binary system in which a transactivator protein is also required. The transactivator is a combination of the tet repressor (tetR), which binds very tightly to tet operator sites, fused to the transcriptional activation domain of virion protein 16 (VP16) from herpes simplex virus. Both pRIP8(O2)7/RIPi/INS/IRES/NEO and an expression plasmid containing the tetR-VP16 transactivator will be stably transfected into RIN38 cells. Precedence for this type of scheme was recently demonstrated when the activity of the already potent CMV promoter was increased another 10-fold by inserting seven tet operator sites between the enhancer and promoter followed by cotransfection with the tetR-VP16 transactivator.

The transcriptional activity of promoters other than CMV, RIP, and RIP derivatives also has been analyzed. Stable RIN38 lines were established which contained the promoter from the Rous Sarcoma Virus Long Terminal Repeat (RSV) driving the standard hINS/IRES/NEO stable transfection vector. In general, the RSV promoter produced hINS mRNA levels roughly equivalent to those produced by RIP. Therefore, the RSV promoter, like the CMV promoter, RIP, and RIP derivatives, acts as a strong transcriptional activator in RIN cells in culture. The human glyceraldehyde-3-phosphate dehydrogenase promoter (GAPDH) was also tested in stably transfected RIN38 cell lines and found to be a weak transcriptional activator. In most GAPDH promoter lines, hINS mRNA was either barely or not detectable by Northern blot analysis.

Promoter stability in vivo. As described earlier for the CMV and RIP promoters, the activity for some of the RIP derivatives, RSV, and GAPDH promoters was analyzed in vivo by subcutaneous injection of engineered RIN 1046-38 lines into athymic Fisher nude rats. In vivo activity of RIP was also reanalyzed, but this time without the presence of a CMV driven transgene as was the case for RIN line EP11/3E9. Time points were again restricted to one to two months as most of the animals developed hypoglycemia by two weeks after injection. The data from these experiments is summarized below.

In vivo RIP activity was examined for two independent RIN lines containing the pRIP8/INS/IRES/NEO transgene. Each line was injected into two individual nude rats. Animals containing either line became hypoglycemic between one to two weeks after injection. Tumors were excised at different intervals, homogenized, and analyzed for hINS mRNA levels by Northern blotting. The amount of hINS mRNA remained constant out to the longest examined time points, 31 days for line 2.18 and 36 days for line 2.38. Therefore, RIP activity remained stable throughout the length of the experiment. The same results were obtained for the modified RIP promoter/enhancers, RIP/RIPi and FFE3/RIP. Both RIP/RIPi and FFE3/RIP produced constant levels of hINS mRNA out to the longest time point of 49 days.

The activity of the RSV promoter appears to be attenuated in vivo. Despite the formation of medium to large tumors, neither animal injected with the 3.4 line became hypoglycemic even after 36 days. Presumably, if analyzed at later time points, these animals would become hypoglycemic due to the endogenous expression of rat insulin from the engineered RIN lines. Both animals injected with the 3.34 line eventually did become hypoglycemic but it took much longer (20 to 30 days) than it did for the RIP and modified RIP lines (10 to 15 days). These data suggest that although the RSV enhancer/promoter is a strong transcriptional activator in cultured RIN cells, it may be unsuitable to direct the expression of a linked transgene in RIN cells in an in vivo situation. Further in vivo testing of RSV promoter activity utilizing a transgene other than the human insulin cDNA is presently underway.

GAPDH promoter activity remained stable in vivo out to the longest time point of 22 days. Both animals injected with the 4.5 line (the GAPDH line that produced the highest level of insulin mRNA) started to become hypoglycemic by 13 to 15 days. This result was somewhat surprising based on the relatively low abundance of HINS mnRNA expressed in this line.

A concern with the use of the viral promoters is their long-term stability of expression in vivo. There are numerous reports concerning loss of transgene expression in vivo, either following introduction of genes in vivo with recombinant viruses or introduction of genes into cells ex vivo followed by implantation of the cells in vivo (Palmer et al., 1989 and 1991, Scharfinann et al., 1991, Challita and Kohn, 1994). This second scenario is analogous to the proposed use of the cell lines being developed here for therapeutic use.

Interestingly, the RSV promoter driving transgenes in RIN clones appear to be attenuated in vivo. The mechanism for this attenuation is not clear. Evidence suggests that some of the problems with long term stability of expression of transgenes driven by viral promoters is due to immune recognition and ultimately rejection of the engineered cells (Dai et al., 1995, Yang et al., 1994). Immune recognition could be directed against the transgene product itself or against other antigens expressed following introduction of the transgenes (i.e., low level viral protein expression from recombinant viral transductions). However, in these studies using nude rats, there is no immune rejection of the implanted cells.

Cell growth, insulin content, and processing in bioreactors. The oxygen gas controller output is monitored throughout the run. It is an indirect indication of the cells' oxygen consumption rate. It rises steadily from around −40 at 0 hours to around 60 at approximately 500 hours where it stabilizes for the rest of the run. The rate of increase of the controller output correlates with an expected growth rate of the culture, and maximum level of 60 is consistent with achieving a cell density of $1.1-2.3 \times 10^8$ cells per ml of bed volume. The cell densities are confirmed at the end of the culture. With a surface-to-volume ratio of 120 $cm^2/cm^3$, the polyester disc bed yields a surface cell density comparable to that obtainable in two dimensional T flask culture. It is important to note that the growth and the sustained densities in the reactor are achieved using a serum free media. High density cultures have been maintained problem free for up to 2000 hours in serum free medium. This observation is novel and very useful in the design of a bulk process for production of biological pharmaceuticals.

Cells harvested from the reactor at the end of culture by trypsinization, plated onto T75 culture flasks, and assayed for insulin secretion performance after 24 hours of culture, show no significant difference relative to sister cells maintained in T75 flask culture, suggesting that the bioreactor milieu is not changing the cells' phenotype in any detectable fashion and that the cells quickly readapt to culture in tissue culture flasks.

HPLC separation of samples collected mid-run at around 550 hours of culture showed effective insulin processing. The ratio of mature human insulin to human proinsulin was 92:8. This efficient processing is obtained from a culture that has reached a steady state of oxygen uptake, indicating no overall growth, and that is sustained in a serum free medium.

The bioreactor data indicates that the steady state environment in the reactor allows for growth of up to approximately $2 \times 10^8$ cells per ml bed, while maintaining pathways crucial for complete processing and storage of insulin.

B. Glucagon Expression and Protein Processing in RIN Cells.

Materials and Methods

Rat glucagon cDNA isolation. Total rat pancreatic RNA was reverse transcribed into total cDNA using AMV Reverse Transcriptase as recommended by the supplier (Promega, Inc., Madison, Wis.). A rat glucagon cDNA corresponding to bases 10 to 904 of the published sequence (Heinrich et at., 1984) was amplified with the polymerase chain reaction from the pancreatic cDNA using oligos (CCACCTGTCTACACCTCCTCTC, SEQ ID NO: 36 and GTAATCCAGGTGTCGTGACTGC, SEQ ID NO:37). The resulting 895 base PCR™ product was ligated into pNoTA/T7 as recommended by supplier (5 Prime to 3 Prime, Inc., Boulder, Colo.), generating pNoTAT7/Glucagon.

Cell culture. RIN 1046-38 (Gazdar et al., 1980, and Clark et al., 1990), RIN 1027-B2 and RIN 1046-44 (Philippe et al., 1987) were grown in Medium 199 with Earle's salts, containing 11 mM glucose and supplemented with 5% fetal calf serum, 100 milliunits/ml penicillin and 100 μg/ml streptomycin. AtT-20-derived cell lines were cultured as described (Hughes et al., 1992). Cells were passaged once a week using 0.05 % trypsin-EDTA solution and kept under an atmosphere of 95% air and 5% $CO_2$ at 37° C.

Northern analysis. Northern analysis of glucagon transcripts in cell lines was done as described above for human insulin message using a digoxigenin-labeled antisense probe generated from pNoTAT7/Glucagon using T7 polymerase as recommended by supplier (Boehringer Mannheim, Inc.).

Results

Endogenous glucagon message is expressed in a subset of cell lines. Glucagon, a 29-amino acid peptide hormone involved in the regulation of glucose and fatty acid metabolism (Unger and Orci, 1981), is proteolytically processed from preproglucagon, a large polypeptide precursor. Expression of the message for preproglucagon is found in a number of cell types, most notably alpha cells of the pancreas and L cells of the intestine. Preproglucagon posttranslational processing differs in these cell types, giving rise to predominantly glucagon from the alpha cells and Glucagon-like Peptides I and II (GLP-I and II) from L cells (Mojsov et al., 1986). The reason for this differential production in alpha cells and L cells is due to differential levels of expression of the endoproteases PC2 and PC3 (Rouille et al., 1995). The expression of these endoproteases is known to vary in other cell types as well (Day et al., 1992), giving rise to cell-specific posttranslational processing of POMC into distinct hormone peptides.

Rat insulinoma cells have been shown to express the glucagon message (Philippe et al., 1987). A series of RIN cell derivatives all originating from the same original insulinoma (Gazdar et al., 1980) were screened for expression of endogenous glucagon message. Northern analysis of various cell lines probed for glucagon message demonstrated that several cell lines do not express endogenous glucagon message including the RIN 1046-38 line used in this patent, AtT-20 cells (a rat pituitary derived cell line serving as a negative control) and an independent RIN line, RIN 1027-B2 (Philippe et al., 1987). However, RIN 1046-44 cells, again independently derived from the same original insulinoma, does express the glucagon message (Philippe et al., 1987). The majority of permanent clones we have developed from the RIN 1046-38 parental line do not express the glucagon message. However, occasional clones of RIN 1046-38, such as EP53/114, engineered to overexpress rat glucokinase, now expresses significant levels of endogenous glucagon message. Expression of glucagon is not related to the glucokinase transgene expression (or any other specific transgene), as other clones overexpressing glucokinase do not express endogenous glucagon.

Expression of the endogenous glucagon message in RIN 1046-38 cells does suggest that it is possible to express a glucagon transgene in these cells. Construction of a glucagon expression plasmid by cloning the preproglucagon open reading frame of pNoTAT7/glucagon into pCMV8/IRES/NEO/hGHPolyA followed by transfection into RIN 1046-38 would result in high-level expression of the glucagon transgene message. Examples of this for several other genes including human insulin, human growth hormone and rat amylin are given herein.

Post-translational processing of preproglucagon into glucagon is dependent upon the specialized functions found in cells with a regulated secretory pathway. This is true in the endogenous cells that normally make glucagon (pancreatic alpha cells) and, as demonstrated in this patent, is true for RIN 1046-38 cells. Expression of preproglucagon transgenes in a variety of cell lines has demonstrated cell-specific differences in processing (Drucker et al., 1986). RIN 1046-38 cells have the capacity to produce, process, store and secrete human insulin as demonstrated in the above example. This includes high endogenous expression of PC2 and PC3, endoproteases involved in processing both insulin and glucagon.

RIN 1046-38 cells also should process preproglucagon into GLP-I and II. Final maturation of GLP-1 involves C-terminal amidation by peptidylglycine alpha-amidating monooxygenase (PAM), discussed in further detail below. Engineering RIN cells to predominantly produce glucagon or GLP-1 is possible by molecular engineering. Processing of preproglucagon to glucagon is predominantly by the action of PC2, while processing to GLP-1 is predominantly by PC3. Overexpression of either a PC2 or PC3 transgene could result in predominant expression one peptide hormone over another. Alternatively, mutations can be induced in the glucagon transgene such that the dibasic amino acid residues recognized by PC2 and PC3 are altered such that only glucagon or GLP-1 is capable of being processed to the mature, biologically active polypeptide.

C. Human Insulin Disulfide Mutant Production

Materials and Methods

Human insulin disulfide mutant expression plasmid. The human insulin open readings frame was amplified with the polymerase chain reaction from a human insulin cDNA using oligos 1 and 2 (CCGGGGATCCTTCTGCCATGGCCC, SEQ ID NO:38 and GGGCTAGATCTAGTTGCTGTAGTTCTCCAGCTGGTAGAGGGAGCAGATGCTAGTACTGCATTGTTCCAC, SEQ ID NO:39) generating a 358 base product (SEQ ID NO:3). Oligo 1 introduces a BamHI site 7 bases upstream of the initiator methionine of insulin. Oligo 2 introduces a BglII site just downstream of the insulin stop codon and introduces two point mutations into the insulin coding region. These mutations change cysteine at position 96 and cysteine at position 109 to serines (SEQ ID NO:4). Both of these amino acid substitutions are in the insulin A chain and disrupt the two disulfide bonds normally formed between the A and B chains. The mutated insulin protein should be expressed, targeted to the regulated secretory pathway and proteolytically processed to human insulin A, B and C chain. Upon stimulated secretion, the three peptide chains would be released by the cell without the normal disulfide bonds between the A and B chain. As a control, the wild-type human insulin open reading frame was amplified with the polymerase chain reaction from a human insulin cDNA using oligos 1 and 3 (CCGGGGATCCTTCTGCCATGGCCC, SEQ ID NO:38 and GGGCTAGATCTAGTTGCAGTAGTTCTC, SEQ ID NO:40). Again, Oligo 1 introduces a BamHI site 7 bases upstream of the initiator methionine of insulin. Oligo 2 introduces a BglII site just downstream of the insulin stop codon without introducing any changes into the insulin coding sequence. The resulting 358 base pair PCR™ products were cloned directly into pNoTA/T7 (Prime PCR™ Cloner Cloning System, 5 Prime to 3 Prime, INC.) generating pNoTA/T7/mutINS and pNoTA/T7/wtINS. These plasmids were subsequently restricted with BamHI and BglII endonucleases and ligated into BamHI digested pCMV8/IRES/NEO/hGH PolyA, generating pCMV8/mutINS/IRES/NEO and pCMV8/wtINS/IRES/NEO, respectively.

A variation of pCMV8/mutINS/IRES/NEO was created by restoring the normal 3'-untranslated region of the insulin cDNA to its correct position following the insulin disulfide mutant open reading frame. An HgaI cleavage site is located 9 bases 3' of the insulin stop codon, base 364 of SEQ ID NO: 1. pBS/INS was digested with HgaI, treated with Klenow fragment, and then digested with HindIII. The resulting 198 base pair fragment was ligated into pNoTA/T7/mutINS that had been digested with BglII, treated with Klenow fragment, and then digested with HinDIII. The resulting plasmid, pNoTA/T7/mutINS+INS3', contains an essentially restored human insulin cDNA except for the two point mutations introduced into the coding region and a 5 base deletion at the BglII/HgaI cloning junction. This 198 base pair fragment contains 64 bases of the insulin 3'-untranslated region, a 41 base pair polyA tract, a 16 base pair poly C tract and 77 base pairs of polylinker sequence from the subcloning vectors. pNoTA/T7/mutINS+INS3' was digested with BamHI, generating a 512 base fragment containing the mutant insulin and reconstructed insulin 3' sequence, which was ligated into the BamHI site of pCMV8/IRES/NEO/hGHPolyA, generating pCMV8/mutINS+3'/IRES/NEO.

Cell culture and stable transfection of cell lines. As described above for insulin producing cells.

Immunohistochemical staining for human insulin C-peptide. Individual G418-resistant RIN clones generated by electroporation using pCMV8/mutINS+3'/IRES/NEO were screened by immunostaining for human C-peptide. Cells were plated on multiwell slides one or more days before staining. Slides with spread cells were rinsed with PBS, then fixed 15–30 minutes in 4% paraformaldehyde. Fixation was followed by a PBS rinse and permeabilization by passage through an ethanol series of 50%-70%-50% (5 minutes each). Permeabilization was followed by a PBS rinse and a 30 minute incubation in 50 mM Tris, pH 7.4, with 1% goat serum, 0.05% Triton and 0.1% azide. Slides were incubated with 1:10,000 dilution of rabbit anti-human. C-peptide (Linco Inc.) for 24 hours. Excess primary antibody was removed with sequential washes (3 minutes each) with PBS-Triton (0.05%), PBS alone, and 50 mM Tris, pH 8.0. The slides were then incubated with an alkaline phosphatase-labeled second antibody (goat anti-rabbit IgG, Sigma Chemicals) in 50 mM Tris with 1% BSA and 1 mM magnesium chloride (Tris-BSA-Mg) for 30 minutes. Excess second antibody was removed with 3 washes of Tris-BSA-Mg. Alkaline phosphatase activity was then visualized by incubating 5 minutes in an alkaline phosphatase substrate solution (BCIP/NBT).

Northern analysis. Northern analysis of mutant insulin transcripts in cell lines was performed as described above for human insulin message detection using a full-length digoxigenin-labeled antisense probe corresponding to the neomycin resistance gene (control template supplied in Genius 4 Kit).

Results

Recent reports suggest that immunomodulatory treatments with insulin can delay or prevent the onset of hyperglycemia in NOD mice (Shehadeh et al., 1994; Sadelain et al., 1990, and Muir et al., 1993). Clinical trials evaluating the prophylactic nature of insulin in humans at high risk for the development of type I diabetes are underway (Keller et al., 1993). Recently, immunization with metabolically inactive insulin B-chain also prevented the onset of hypoglycemia in NOD mice, suggesting an active induction of immunoregulation by insulin. Development of an in vivo cell-based delivery system of insulin or metabolically inactive forms of insulin could be used prophylactically in humans at high risk of developing type I diabetes. Cell lines producing and secreting high levels of mature human insulin have already been described here. This would be done in the context of the expression of reduced endogenous rat insulin. Neuroendocrine cells producing an inactive, mutant human insulin, in the context of reduced endogenous rat insulin production, would offer a safer, and possibly more efficacious approach. The use of metabolically inactive insulin would negate the possibility of insulin induced hypoglycemia. Higher amounts of a metabolically inactive insulin could therefore be safely administered in vivo, possibly increasing the efficacy of the treatment.

To this end, RIN cells have been engineered to produce a mutant form of human insulin. Insulin is initially produced in the cell as proinsulin, a larger peptide precursor consisting of the linear arrangement of insulin B-chain C-chain A-chain. The maturation of proinsulin to mature insulin is well understood (Halban, 1991) with three major steps in the process. The first is folding of the proinsulin into a native conformation in the immature secretory granules. The second step involves the formation of three disulfide bonds, one intramolecular in the A-chain and two intramolecular between the A-chain and the B-chain. The final step is the endoproteolytic processing by PC2 and PC3 followed by carboxypeptidase processing in the mature secretory granule. The mature granules contain an equimolar mix of C-chain (C-peptide) and mature insulin consisting of a A-chain/B-chain heterodimer covalently linked by the two intramolecular disulfide bonds. A mutant form of insulin was constructed from the human insulin cDNA in which the two codons encoding cysteines in the insulin A-chain have been mutated to codons encoding serines (SEQ ID NO:3). Expression of this mutant open reading frame should produce a mutant insulin peptide (SEQ ID NO:4) that still folds normally, the intrachain disulfide bond in the A-chain can still form, and endoproteolytic processing and carboxypeptidase cleavage can still occur. The mature granules should now contain an equimolar mix of C-chain (C-peptide) and free B-chain and A-chain. The B-chain is identical in sequence to the wild-type human insulin B-chain used in studies showing the prevention of the onset of hypoglycemia in NOD mice (Muir et al., 1995). Stimulated release of the contents of the secretory granules would release all three peptides. Engineering of these RIN cells in the context of reduced rat insulin production would ensure no insulin biologic activity.

D. Rat Amylin Production

Materials and Methods

Rat Amylin expression plasmid. A HinDIII/XbaI fragment corresponding to bases −66 to +611 of the published rat amylin cDNA sequence (SEQ ID NO:7, Leffert et al., 1989) was treated with Klenow Fragment to blunt the ends. This blunt-ended fragment was ligated into the Klenow treated XbaI site of pCMV8/IRES/NEO/hGH PolyA generating pCMV8/Amylin/IRES/NEO. The CMV promoter drives transcription of a bicistronic messenger RNA with rat amylin encoded in the upstream open reading frame and the neomycin resistance gene encoded in the downstream open reading frame. Stable transfectants from this plasmid are selected in G418.

Cell culture and stable transfection of cell lines. RIN 1046-38 cells were cultured and transfected as described above for insulin producing cells.

Immunohistochemical staining for rat Amylin. As described above for human insulin C-peptide, with the following changes. The primary antibody was a rabbit anti-rat amylin polyclonal used at 1:1000 and 1:200 dilutions (Peninsula Labs, IHC 7323) for 80 minutes at room temperature.

Northern analysis. Northern analysis of rat amylin transcripts in cell lines was done as described above for human insulin message detection. Filters were hybridized with a full-length digoxigenin-labeled antisense probe corresponding to the rat amylin cDNA (SEQ ID NO:7) made using Genius 4 RNA Labeling Kit (Boehringer Mannheim) and T7 polymerase. Northern analysis of rat peptidylglycine alpha-amidating monooxygenase (PAM) in cell lines was done as described using a digoxigenin-labeled antisense probe corresponding to the bases 240 to 829 of the rat PAM cDNA (Stoffers et al., 1989) made using Genius 4 RNA Labeling Kit (Boehringer Mannheim) and T7 polymerase.

Stimulated amylin secretion assay and determination of DNA content and cell number. This assay was performed as described for insulin secretion assay and cell number determination.

Amylin radioinimunoassays. Determination of rat amylin concentrations in stimulated and basal media samples was performed as previously described (Pieber et al., 1994).

Results

Peptidylglycine alpha-amidatin, monooxygenase expression in cell lines. Alpha-amidation is now appreciated as a critical determinant for biological activity of a large number of peptide hormones. Table 3 represents a sample of human peptide hormones that are known to be amidated in vivo. The enzyme involved in alpha-amidation, peptidylglycine alpha-amidating monooxygenase (PAM), has been well characterized at the molecular level (reviewed in Eiper et al., 1992a). Although there is only one gene in mammals encoding PAM (Ouafik et al., 1992), there are several forms of PAM due to alternative splicing and endoproteolytic processing (Stoffers et al., 1989 and 1991, Eiper et al., 1992b) leading to both membrane-bound and secreted forms of PAM. PAM is also known to be developmentally regulated and differentially expressed in vivo (Ouafik et al., 1989). The importance of alpha-amidation of peptide hormones is such that the presence of the consensus glycine followed by two basic amino acids (lysine and/or arginine) in a novel amino acid sequence can be predictive of its being a precursor to a bioactive polypeptide (Cuttita, 1993).

Amylin and GLP-1 are two peptide hormones that are amidated in vivo. A more complete list of amidated human polypeptide hormones is found in Table 3. Attempts at mammalian cell production of any of these hormones requires endoproteolytic cleavage of larger precursors, carboxypeptidase trimming and alpha-amidation. For instance, Glucagon-Like Peptide 1 (GLP-1) is a peptide hormone with powerful insulinotropic effects secreted from the intestinal L cells in response to meals (Kreymann et al., 1987). It processed from a larger polypeptide precursor through steps that are very similar to the processing of amylin. Processing of GLP-1 involves the action of the endoproteases PC2 and PC3 and carboxypeptidase on the same precursor that glucagon (Mojsov et al., 1986 and Rouille et al., 1996). The final biologically active peptide is a mixture of GLP-1 7-37 and GLP-1 7-36 amide, a difference resulting from the alternative processing of the glycine at position 37 to an alpha-amidated form by peptidylglycine alpha-amidating monooxygenase (PAM) (Orskov et al., 1989 and Mojsov et al., 1990). Both GLP-1 7-37 and GLP-1 7-36 amide are both biologically active in humans (Orskov et al., 1993). The rat insulinoma cell line used here., RIN 1046-38 has already been shown to express sufficient levels of PC2, PC3 and carboxypeptidase for complete processing of highly expressed human insulin.

Amylin is a 37 amino acid polypeptide hormone again processed from a larger precursor polypeptide by the proteolytic processing (Sanke et al., 1988). Amylin is normally co-produced and co-secreted with insulin by β-cells, acting as a hormone to regulate carbohydrate metabolism (Hoppener et al., 1994). However, unlike insulin, amylin is alpha-amidated by PAM in the β-cells (Sanke et al., 1988). Overexpression of amylin in RIN 1046-38 cells will serve as a demonstration of the ability of these cells to produce amidated peptide hormones.

Northern analysis was used to address the endogenous levels of PAM in various cell lines. Expression of PAM in RIN 1046-38 is compared to AtT-20 and two related RIN lines, RIN 1027-B2 and RIN 1046-44 (Philippe et al., 1987). Endogenous expression of a single PAM message of approximately 3.5 kB is easily detected in all three RIN lines (FIG. 14, Lanes 1, 3 and 4). Lower expression of two PAM messages of approximately 4.0 and 3.5 kB is found in AtT-20 cells (FIG. 14, Lane 2). PAM message sizes of 3.5 to 4.0 kB is consistent with the larger spliced variants of PAM message known to encode active PAM protein (Stoffers et al., 1989). Expression of endogenous PAM was compared with expression of endogenous amylin in these same cell lines. The three RIN lines with high levels of PAM also showed high levels of endogenous amylin expression (FIG. 14, Lanes 1, 3 and 4). AtT20 cells, a pituitary cell line does not have any endogenous amylin expression. Interestingly, two RIN 1046-38 derived clones (EP18/3G8 expressing large amounts of human insulin (FIG. 11) and EP53/114 overexpressing rat glucokinase) that no longer express endogenous amylin show lower levels of expression of endogenous PAM (FIG. 14, Lanes 5 and 6). The majority of RIN 1046-38 derived clones continue to express both endogenous amylin and PAM, suggesting that RIN 1046-38 derived clones will maintain the ability to efficiently amidate peptide hormones.

The high level of PAM expression in RIN 1046-38 compared to AtT-20 is very encouraging. Comparison of PAM expression in other cell types has shown that AtT-20 cells express very high enzyme levels (Takeuchi et al., 1990). This includes higher levels than PC12 cells and RIN5-f cells, a rat insulinoma line that is fairly dedifferentiated when compared to RIN 1046-38. Maintaining high PAM activity in RIN 1046-38, similar to maintaining high levels of PC2 and PC3 activity, suggests overexpression of transgenes for amidated peptide hormones such as amylin will result in their efficient production.

Amylin transgenes are efficiently expressed in RIN 1046-38 cells. The rat amylin cDNA was cloned into pCMV8/IRES/NEO/hGHPolyA, generating pCMV8/AMYLIN/IRES/NEO. Expression plasmids similar to this have resulted in good overproduction of other transgenes. Individual stable clones were screened for amylin expression with an in situ immunostaining protocol utilizing two dilutions of the primary amylin antibody. At the lower dilution (1:200) all the cells are positive due to the levels of endogenous amylin. At the higher dilution (1:1000), only a subset of clones continued to stain, presumably due to overexpression of the amylin transgene. Five such clones were picked and shown to express the amylin message.

Expression of biologically active amidated peptides in RIN 1046-38 cells. Table 3 is; a list of known amidated peptide hormones in humans. RIN 1046-38 cells can be engineered to overexpress the cDNA transgenes encoding the precursors to these peptide hormones. RIN lines have been used in the past to express the transgenes for preproglucagon and pancreatic polypeptide resulting in low-level or partial processing to the final amidated polypeptides (Drucker et al., 1986 and Takeuchi et al., 1991). Based on our results with overexpression of human insulin and rat amylin, RIN 1046-38 cells are expected to efficiently process and secrete fully bioactive, amidated polypeptides. As claimed in this patent, this would be done in cells that have also been engineered such that an endogenous gene expressing a secreted protein has been blocked. In this way, a cell overexpressing a biologically active peptide hormone, in this case one that is also amidated, is produced in a defined cellular background for use in in vitro large scale production or for in vivo cell-based delivery of the active peptide hormone.

E. Human Growth Hormone Production

Materials and Methods

Human growth hormone production plasmid. The gene encoding human growth hormone was isolated on a 2086 base BamHI/AgeI restriction endonuclease fragment from pOGH (Nichols Institute Diagnostics, Inc., San Capistrano, Calif.). This fragment corresponds to bases 498 to 2579 of the published gene sequence (SEQ ID NO:9, Seeburg, 1982). The BamHI site is located at the normal site of transcription of the message, 61 bases 5' of the initiator methionine. The AgeI site is located 3' of the transcribed sequences of the growth hormone gene. This fragment was ligated into pCB6 (Brewer, 1994) that had been digested with BglII and AgeI, generating pCB6/hGH. The BglII site places the hGH gene just downstream of the CMV promoter. The AgeI site in pCB6 is located in the human growth hormone polyadenylation element contained in that plasmid. The polyadenylation element is restored by cloning the entire human growth hormone gene into pCB6. Stable transformnants of pCB6/hGH are selected in G418.

Cell culture and stable transfection of cell lines. These studies were performed as described above for insulin producing cells.

Screening and characterization of human growth hormone producing clones. Individual G418 resistant clones generated by electroporation using pCB6/hGH were screened for hGH in the conditioned media using an hGH radioisotopic assay kit (Nichols Institute Diagnostics).

Stimulated growth hormone secretion assay and determination of DNA content and cell number. Done as described for insulin secretion assay and cell number determination.

Results

Mammalian cell production of human growth hormone. Growth hormone has been shown to be the major regulator of growth in children as well as maintaining or restoring various metabolic functions which can decrease with age (Isaksson et al., 1985 and Arimura, 1994). Purified recombinant human growth hormone is now being produced from mammalian cells in bioreactors for clinical use (Eshkol, 1992). Constitutive cell-based delivery of growth hormone from ex vivo engineered primary fibroblasts (Selden et al., 1987 and Heartlein et al., 1994) or primary myoblasts (Dhawan et al., 1991 and Barr and Lei(len, 1991) is also being attempted. Fully processed, bioactive growth hormone is produced in all of these systems. Our attempts to engineer neuroendocrine cells to produce recombinant human growth hormone offers two advantages. The first is the ability to engineer high levels of growth hormone into a stable cell line with the various methods outlined here to maximize production levels. This engineering is being done in a cell line in which production of an endogenous secreted protein has been blocked. The second advantage is that the growth hormone produced in these cells is packaged into secretory granules where regulated release of growth hormone is possible. Normally, growth hormone is not secreted constitutively, but is secreted in a pulsatile manner as regulated by Growth Hormone Releasing Factor and Somatostatin (Arimura, 1994). Growth hormone produced recombinantly in neuroendocrine cells is known to be secreted through the regulated secretory pathway where its release from the cells can be regulated (Moore and Kelly, 1985). In β-cells, growth hormone produced from a transgene is also secreted via the regulated secretory pathway and secretion can be costimulated along with the endogenous insulin (Welsh et al., 1986).

RIN 1046-38 clones produce high levels of recombinant human growth hormone. Seventeen independent clones derived from electroporation of RIN 1046-38 cells with pCB6/hGH were screened for secretion of human growth hormone (hGH). No detectable hGH was detectable from conditioned media from parental RIN 1046-38. Fourteen of the 17 clones expressed significant levels of hGH. Six clones were expanded and characterized further.

hGH is expected to be secreted via the regulated secretory pathway in these clones. Cells were cultured for 24 hours in fresh tissue culture media containing 11 mM glucose and 5% fetal calf serum. This conditioned media was collected and immunoreactive hGH was determined (6 independent samples/clone were analyzed, 24 hour collection). Cells were washed and either incubated for one hour in media lacking glucose and containing 100 µM diazoxide (basal, 2 samples per clone) or incubated for one hour in media containing 5 mM glucose, 100 µM carbachol, 100 µM IBMX and amino acids (stimulated, 4 samples per clone). Cell numbers for each sample was determined and all hGH values are normalized to µg of secreted product per million cells. The values are reported in FIG. 14.

Over a 24 hour collection, the six clones secreted between 25 and 229 µg hGH per million cells per 24 hours. Clone EP 111/31 has consistently been the highest hGH producing clone in both the initial screens and in these studies. 229 µg hGH per million cells per 24 hours is higher than any value of hGH production by a mammalian cell. Previous reported values are in the range of 7–20 µg/million cells/24 hours (Pavlakis and Hamer, 1983) and the highest value reported is 40 µg/million cells/24 hours (Heartlein et al., 1994).

hGH secretion by these six clones is also exquisitely regulated. Basal secretion values were all less than 100 ng/million cells/hour, easily detected in the assay, but barely visible in FIG. 14. Basal values are in the range of 0.1% to 1.0% of the stimulated values for each clone. Stimulated secretion ranged from 6 to 40 µg hGH/million cells/hour. The one hour output of EP111/31 of 40 µg/million cells is equivalent to the best 24 hour output reported to date (Heartlein et al., 1994).

The absolute outputs of hGH by RIN clones, as well as the fact that it is secreted via the regulated secretory pathway, are important for both in vitro production and in vivo cell-based delivery. For in vitro production, these cells are producing more hGH in normal tissue culture per 24 hours than previously described cells. Cyclical stimulation of these cells in a bioreactor setting, as previously described for insulin production, cab be used for bioreactor production. In vivo cell-based delivery of hGH could use the cells in their present form where secretion of hGH would be fairly constant. Alternatively, further engineering of the cells could produce a more physiological pulsatile release of hGH in vivo by conferring regulation of growth hormone secretion to growth hormone-releasing factor and/or somatostatin, or other regulators of somatotropes (Arimura, 1994).

EXAMPLE 3

Engineering Cells for High Level Expression

A. Rat Insulin Promoter Factor 1 (IPF1)—

Materials and Methods

Rat IPF1 expression plasmids. A plasmid containing the rat IPF1 cDNA was obtained from Chris Wright (XB-pdx1). This plasmid contains the open reading frame of rat IPF1 (SEQ ID NO:5, bases 7 to 861) cloned into pXBm (Krieg and Melton, 1984), placing Xenopus β globin 5'- and 3'-transcribed but untranslated sequences 5' and 3' of the rat IPF1 sequence. This construct was made to help stabilize the IPF1 message, allowing for higher steady-state message levels and protein production. A HinDIII/BamHI fragment containing the IPF1 and globin sequences was ligated into the HinDIII and BamHI sites of pCB6 (Brewer, 1994), generating pCB6/IPF1. Alternatively, the IPF1 and globin sequences of pCB6/IPF1 was removed by digestion with BglII and BamHI and cloned into the BamHI site of pCMV8/IRES/NEO/hGHPolyA, generating pCMV8/IPF1/IRES/NEO. Stable transfectants of both of these expression plasmids are selected using G418.

It was not clear that the Xenopus β globin sequences would stabilize the IPF1 transgene in RIN cells. For this reason, the IPF1 open reading frame was amplified with the polymerase chain reaction from pCB6/IPF1 using two oligos (GGATCCATGAACAGTGAGGAGCAG, SEQ ID NO:41 and AGATCTTCACCGGGGTTCCTGCGG, SEQ ID NO:42). The resulting 867 base product (SEQ ID NO:5) was cloned into pNoTA/T7 (5 Prime to 3 Prime, Inc., Boulder, Colo.) generating pNoTA/T7/IPF1. The IPF1 open reading frame was removed from pNoTA/T7/IPF1 by digestion with BamHI and was ligated into BamHI digested pCB6, generating pCB6/IPF1(-Bg). Alternatively, the same IPF1 BamHI fragment was ligated into BamHI digested pCMV8/IRES/NEO/hGHPolyA, generating pCMV8/IPF1(-Bg)/IRES/NEO. A final expression plasmid was made, ligating the IPF1 BamHI fragment into BamHI digested pCMV8/Ins3'/IRES/NEO, generating pCMV8/IPF19-Bg)/Ins3'/IRES/NEO. The Ins3' nontranslated region in these plasmids was described earlier for the insulin disulfide mutant example and is contained on a 198 base pair HgaI/HinDIII fragment. This fragment was ligated into pCMV8/IRES/NEO/hGHPolyA generating pCMV8/Ins3'/IRES/NEO. Stable transfectants of all of these expression plasmids are selected using G418.

Cell culture and stable transfection of cell lines. These studies were performed as described above for insulin producing cells.

Screening and characterization of IPF1 producing clones. Northern analysis of individual G418 resistant clones generated from the various IPF1 expression plasmids was done as described above for the human insulin northern analysis. Blots were hybridized with a $^{32}$P-labeled cRNA probe corresponding to the rat IPF1 open reading frame (SEQ ID NO:5).

Results

Overexpression of IPF-1 in RIN 1046-38 cells. IPF-1 functions both in the specification of a region of the primitive gut to form pancreas and in the maturation of the pancreatic β-cell. Because RIN 1046-38 cells retain only some of the differentiated features of a normal β-cell, overexpression of IPF-1 in these cells could cause them to function more like mature β-cells. Thus, redifferentiated RIN cells may serve as a more effective bioreactor for the production of biologically relevant secreted proteins.

In initial experiments, stable transfection of RIN 1046-38 cells with either pCMV8/IPF-1I/IRES/NEO or pCB6/IPF-1 resulted in a low number of NEO-resistant colonies. None of these colonies expressed the IPF-1 transgene as demonstrated by Northern blot analysis. A second round of stable transfections were performed with IPF-1 constructs in which the Xenopus 5' and 3' β-globin untranslated sequences (UTR) were removed (IPF-1(-Bg)). Also, in some constructs, the potentially stabilizing Ins3' UTR was fused immediately downstream of the IPF-1 cDNA. A moderate number of NEO-resistant colonies were obtained from RIN cells transfected with either pCMV8/IPF-1(-Bg)IRES/NEO or pCMV8/IPF-1(-Bg)/Ins3'/IRES/NEO. Northern analysis of RNA from a mixed population of colonies containing either construct demonstrated that the IPF-1 transgene mRNA was indeed overexpressed relative to endogenous IPF-1 (FIG. 16; compare the endogenous IPF-1 mRNA at 1.5 kB to the IPF-1 transgene mRNA at 2.3 kB). Exactly why there are two bands migrating to the predicted position for IPF-1 transgene mRNA is not clear. Perhaps the top band represents a fraction of IPF-1/IRES/NEO mRNA in which the 250 bp 5' generic intron has not been spliced out. The addition of the 3'Ins UTR to the IPF-1 cDNA did not appear to have an effect on IPF-1 transgene expression. Screening individual colonies for high-level IPF-1 transgene expression is ongoing.

B. Alternative Drug Selection Markers

Materials and Methods

Expression plasmids with alternative selection markers. To facilitate engineering of multiple genes into the same cell line or to optimize expression of a given gene, alternative expression plasmids containing other drug selection markers were designed. The drug selection markers utilized include the hygromycin resistance gene (HYGRO), the puromycin resistance gene (PURO), the dihydrofolate reductase gene (DHFR) conferring resistance to methotrexate, the xanthine-guanine phosphoribosyltransferase gene (GPT) conferring resistance to mycophenolic acid, the Zeocin resistance gene (ZEO), and the histidinol selection gene (HISD). All of the drug selection genes were tested for their ability to confer drug resistance to RIN cells in two contexts. The first was by substituting the new drug selection gene for the neomycin resistance gene in pCMV8/IRES/NEO. In this context, the drug resistance gene is transcribed off of the CMV promoter as the downstream open reading frame of a bicistronic message. The second is by substituting the new drug selection gene for the neomycin resistance gene in pCB6 (Brewer, 1994) such that the new drug selection gene is driven by the SV40 promoter. pCB7 (Brewer et al., 1994) was constructed this way with the hygromycin resistance gene replacing the neomycin resistance gene.

The open reading frame of the hygromycin resistance gene was amplified using the polymerase chain reaction from pCB7 using oligos (GGGGATCCGATATGAAAAAGCCT(G, SEQ ID NO:43 and CGAGATCTACTCTATTCCTTTGC, SEQ ID NO:44). The resulting 1048 base product was digested with BamHI and BglII and ligated into the BamHI site of pCMV8 generating pCMV8/HYGRO. In a second step, the IRES element (SEQ ID NO: 11) contained on a 235 base BamHI/BglII fragment, was ligated into the BamHI site of pCMV8/HYGRO generating pCMV8/IRES/HYGRO. Stable transformants of pCB7 and pCMV8/IRES/HYGRO are selected using 300 μg/ml hygromycin (Boehringer Mannheim) for 14 days without media changes.

The E. coli open reading frame encoding XGPRT was amplified with the polymerase chain reaction from pSV3/GPT (ATCC#37144, Mulligan and Berg, 1980 and 1981) using oligos (CCGGATCCCATGAGCGAAAAAT, SEQ ID NO:45 and GGAGATCTTTAGCGACCGGAGAT, SEQ ID NO:46). The resulting 476 base pair amplified product was restricted with BamHI and BglII and subcloned into the BamHI site of pCMV8, generating pCMV8/GPT. Next, the IRES element (SEQ ID NO: 1) was ligated into the BamHI site of pCMV8/GPT, generating pCMV8/IRES/GPT. The GPT open reading frame was isolated from pCMV8/GPT by digestion with BamHI and SmaI and the resulting 482 base pair fragment was ligated into pCB6/intron (see above) that had previously been digested with NarI, treated with Klenow fragment and then digested with BclI, generating pCB8. Stable transformants of pCMV8/IRES/GPT and pCB8 are selected using 2.5 to 3.0 μg/ml mycophenolic acid (Sigma Chemical Co.) in media without exogenous xanthine added for 14 days. Media was changed every 3 to 4 days.

The open reading frame of the mouse dihydrofolate reductase cDNA was amplified with the polymerase chain reaction from pSV3-dhfr (ATCC#37147, Subramani et al., 1981) using oligos (CCGGATCCATGGTTCGACCATTG, SEQ ID NO:47 and GGAGATCTGTTAGTCTTTCTTC, SEQ ID NO:48). The resulting 581 base pair amplified product was restricted with BamHI and BglII and subcloned into the BamHI site of pCMV8, generating pCMV8/DHFR. Next, the IRES element (SEQ ID NO: 11) was ligated into the BamHI site of pCMV8/DHFR, generating pCMV8/IRES/DHFR. The DHFR open reading frame was isolated from pCMV8/DHFR by digestion with BamHI and SmaI and the resulting 582 base pair fragment was ligated into pCB6/intron (see above) that had previously been digested with NarI, treated with Klenow fragment and then digested with BclI, generating pCB9. Stable transformants of pCMV8/IRES/DHFR and pCB9 are selected using 1 to 10 μg/ml methotrexate (Amethopterin, Sigma Chemical Co.) for 14 days with media changes every 3 to 4 days.

The open reading frame of the HisD gene was amplified with the polymerase chain reaction from pREP8 (Invitrogen, Inc.) using oligos (CCGGATCCATGAGCTTCAATAC, SEQ ID NO:49 and CCAGATCTGCTCATGCTTGCTCC, SEQ ID NO:50). The resulting 1063 base pair amplified product was restricted with BamHI and BglII and subcloned into the BamHI site of pCMV8, generating pCMV8/HISD. Next, the IRES element (SEQ ID NO:11) was ligated into the BamHI site of pCMV8/HISD, generating pCMV8/IRES/HISD. Stable transfonants of pCMV8/IRES/HISD are selected in media with 0.8 to 1.0 mg/ml histidinol for 14 days. Media was changed every 3–4 days.

The puromycin resistance gene was isolated from pPUR (Clonetech, Inc.) by digestion with PstI and XbaI. The resulting 792 base pair fragment was treated with Klenow fragment and ligated into the SmaI site of pCMV8, generating pCMV8/PURO. Next, the IRES element (SEQ ID NO: 11) was ligated into the BamHI site of pCMV8/PURO, generating pCMV8/IRES/PURO. The PURO open reading frame was isolated from pCMV8/PURO by digestion with NcoI, treated with Klenow fragment, and then digested with BamHI. The resulting 723 base fragment was ligated into pCB6/intron (see above) that had previously been digested with NarI, treated with Klenow fragment, and then digested with BclI, generating pCB10. Stable transformants of pCMV8/IRES/PURO and pCB10 are selected using 1.75 to 2.0 µg/ml puromycin (Sigma Chemical Co.) for 10 days with media changes every 3 to 4 days.

The zeocin resistance gene was isolated from pZeoSV (Invitrogen, Inc.) by digestion with NcoI and AccI. The resulting 430 base fragment was treated with Klenow Fragment and ligated into the SmaI site of pCMV8, generating pCMV8/ZEO. Next, the IRES element pCMV8/IRES/ZEO. The ZEO open reading frame was isolated from pCMV8/ZEO by digestion with RsrII, treated with Klenow fragment, and then digested with BamHI. The resulting 406 base fragment was ligated into pCB6/intron (see above) that had previously been digested with NarI, treated with Klenow fragment, and then digested with BclI, generating pCB11. Stable transformants of pCMV8/IRES/ZEO and pCB11 are selected using 400 µg/ml Zeocin (Invitrogen, Inc.) for 14 days with media changes every 3 to 4 days.

V. REFERENCES

The following references, to the extent that they provide exemplary procedural or other details supplementary to those set forth herein, are specifically incorporated herein by reference:

Adams et al., "Porin interaction with hexokinase and glycerol kinase: Metabolic microcompartmentation at the outer mitochondrial membrane," *Bioch. Med. Met. Biol.*, 45:271–291, 1991.

Aguilar-Bryan et al., "Cloning of the Beta cell high-affinity sulfonylurea receptor: A regulator of insulin secretion," *Science*, 268:423–426, 1995.

Altman et al., *Diabetes* 35:625–633, 1986.

Anderson et al., "Cloning, structure, and expression of the mitochondrial cytochrome P-450 sterol 26-hydroxylase, a bile acid biosynthetic enzyme," *J.B.C.*, 264:8222–8229, 1989.

Arimura et al., "Regulation of growth hormone secretion." The Pituitary Gland, 2nd Edition, Chap.9:217–259. H. Imura, Ed., Raven Press, N.Y., 1994.

Arora, et al. *J.B.C.* 268:18259–18266, 1993.

Asfari et al., "Establishment of 2-mercaptoethanol-dependent differentiated insulin-secreting cell lines." *Endocrinology*, 130:167–178, 1992.

Bahnemann et al. "Animal cell, viral antigens and vaccines," *Abs. Pap. ACS*, 180:5. 1980.

Baichwal et al., "Vectors for gene transfer derived from animal DNA viruses: Transient and stable expression of transferred genes," In: Kucherlapati R, ed. Gene transfer. New York: Plenum Press, pp. 117–148, 1986.

Baijal, et al.,*J. E. Arch. Bioch. Biophys.* 298:271–278, 1992.

Bailey et al., "Methylmercury as a reversible denaturing agent for agarose gel electrophoresis," *Anal. Biochem.*, 70:75–85, 1976.

Barr et al., "Systemic delivery of recombinant proteins by genetically modified myoblasts," *Science*, 254:1507–1509, 1991.

Becker et al., "Differential effects of overexpressed glucokinase and hexokinase I in isolated islets: Evidence for functional segregation of the high and low $K_m$ enzymes," *J. Biol. Chem.*, 271:390–394, 1996.

Becker et al., "Use of recombinant adenovirus for metabolic engineering of mammalian cells," *Methods in Cell Biology*, 43:161–189, Roth, M., Ed. New York, Academic Press, 1994.

Becker et al., "Overexpression of hexokinase 1 in isolated islets of langerhans via recombinant adenovirus," *J.B.C.*, 269:21234–21238, 1994.

Bell, et al., "Characterization of the 56-kDa subunit of yeast trehalose-6-phosphate synthase and cloning of its gene reveal its identity with the product of CIF1, a regulator of carbon catabolite inactivation," *Eur. J. Biochem.*, 209:951–959, 1992.

Bell et al., "Nucleotide sequence of a cDNA clone encoding human preproinsulin." *Nature* 282:525–527, 1979.

Benjannet et al., "Comparative biosynthesis, covalent post-translational modifications and efficiency of prosegmant cleavage of the prohormone convertases PC1 and PC2: Glycosylation, sulphation and identification of the intracellular site of prosegment cleavage of PC1 and PC2," *Biochem. J.*, 294:735–743, 1993.

Benvenisty and Neshif, "Direction introduction of genes into rats and expression of the genes," *Proc. Nat'l Acad. Sci. USA*, 83:9551–9555, 1986.

Berzal-Herranz, A. et al., *Genes and Devel.*, 6:129–134, 1992.

Brewer, "Cytomegalovirus plasmid vectors for permanent lines of polarized epithelial cells," In: *Methods in Cell Biology*, 43:233–245, Roth, M., Ed. New York, Academic Press,, 1992.

Brunstedt et al., "Direct effect of glucose on the preproinsulin mRNA level in isolated pancreatic islets," *B.B.R.C.*, 106:1383–1389, 1982.

Burch, et al., "Adaptation of glycolytic enzymes. Glucose use and insulin release during fasting and refeeding." *Diabetes* 30:923–928.

Burgess et al., "Constitutive and regulated secretion of proteins," *Ann. Rev. Cell Biology*, 3:243–293, 1987.

Cech et al., "In vitro splicing of the ribosomal RNA precursor of Tetrahymena: involvement of a guanosine nucleotide in the excision of the intervening sequence," *Cell*, 27:487–496, 1981.

Challita et al., "Lack of expression from a retroviral vector after transduction of murine hematopoietic stem cells is associated with methylation in vivo," *Proc. Natl. Acad. Sci. USA*, 91:2567–2571, 1994.

Chang et al., "Foreign gene delivery and expression in hepatocytes using a hepatitis B virus vector," *Hepatology*, 14:134A, 1991.

Chavez et al., "Expression of exogenous proteins in cells with regulated secretory pathways," In: *Methods in Cell Biology*, 43:263–288, Roth, M., Ed. New York, Academic Press, 1994.

Chen and Okayama, "High-efficiency transfection of mammalian cells by plasmid DNA," *Mol. Cell Biol.*, 7:2745–2752, 1987.

Chen et al., "Regulated Secretion of Prolactin by the mouse cell line Beta TC-3," *Biotechnology*, 13:1191–1197, 1995.

Chowrira, B. H. et al., *Biochemistry*, 32, 1088–1095.

Chowrira, B. H. et al., "In vitro and in vivo comparison of hammerhead, hairpin, and hepatitis delta virus self-processing ribozyme cossettes." *J.B.C.*, 269:25856–25864, 1994.

Clark et al., "Modulation of glucose-induced insulin secretion from a rat clonal beta-cell line," *Endocrinology*, 127:2779–2788, 1990.

Clark et al., "Islet cell culture in defined serum-free medium," *Endocrinology*, 126:1895–1903, 1990.

Coffin, "Retroviridae and their replication," In: *Virology*, Fields et al. (eds.), New York: Raven Press, pp. 1437–1500, 1990.

Cone et al., *Proc. Nat'l Acad. Sci. U.S.A.* 81:6349–6353, 1984

Cordell et al., "Isolation and characterization of a cloned rat insulin gene." Cell, 18:533–543, 1979.

Couch et al., "Immunization with types 4 and 7 adenovirus by selective infection of the intestinal tract," *Am. Rev. Resp. Dis.,* 88:394–403, 1963.

Coupar et al., "A general method for the construction of recombinant vacciiia virus expressing multiple foreign genes," *Gene,* 68:1–10, 1988.

Curry, "Insulin content and insulinogenesis by the perfused rat pancreas: Effects of long term glucose stimulation," *Endocrinology,* 118; 170–175, 1986.

Cuttitta, "Peptide arnidation: Signature of bioactivity," The Anatomical Record, 236:87–93, 1993.

Dai et al., "Cellular and humoral immune responses to adenoviral vectors containing factor IX gene: Tolerization of factor IX and vector antigens allows for long-term expression," *P.N.A.S. USA,* 92:1401–1405, 1995.

Danos et al., *Proc. Nat'l Acad. Sci. U.S.A.* 85:6460–6464, 1988.

Day et al., "Distribution and regulation of the prohormone convertases PC1 and PC2 in the rat pituitary" *Molecular Endocrinology,* 6:485–497, 1992.

Dhawan et al., "Systemic delivery of human growth hormone by injection of genetically engineered myoblasts," *Science,* 254:1509–1512, 1991.

Dickerson et al., "Transfected human Neuropeptide Y cDNA expression in mouse pituitary cells," *J.B.C.,* 262:13646–13653, 1987.

Drucker et al., "Cell-specific post-translational processing of preproglucagon expressed from a metallothionein-glucagon fusion gene," *J.B.C.,* 261:9637–9643, 1986.

Dubensky et al., "Direct transfection of viral and plasmid DNA into the liver or spleen of mice," *Proc. Nat. Acad. Sci. USA,* 81:7529–7533, 1984.

Efrat, et al., "Ribozyme-mediated attenuation of pancreatic Beta-cell glucokinase expression in transgenic mice results in impaired glucose-induced insulin secretion," *Proc. Natl. Acad. Sci. USA,* 91:2051–2055, 1994.

Efrat et al., "Murine insulinoma cell line with normal glucose-regulated insulin secretion," *Diabetes,* 42:901–907, 1993.

Efrat et al., "Beta-cell lines derived from transgenic mice expressing a hybrid insulin gene-oncogene," *P.N.A.S.,* 85:9037–9041, 1988.

Efrat et al., "Conditional transformation of a pancreatic beta cell line derived from transgenic mice expressing a tetracycline-regulated oncogene," *Proc. Natl. Acac. Sci., USA,* 92: 3576–3580, 1995.

Eipper et al., "Alternative splicing and endoproteolytic processing generate tissue-specific forms of pituitary peptidylglycine alpha-amidating monooxygenase (PAM)," *J.B.C.,* 267:4008–4015, 1992b. Eipper et al., "The biosynthesis of neuropeptides: Peptide alpha-amidation," *Annu. Rev. Neuroscience,* 15:57–85, 1992a.

Epstein, et al., "Expression of yeast hexokinase in pancreatic beta-cells of transgenic mice reduces blood glucose, enhances insulin secretion, and decreases diabetes," *Proc. Natl. Acad. Sci. USA,* 89:12038–12042, 1992.

Ercolani et al., "Isolation and complete sequence of a functional human glyceraldehyde-3-phosphate dehydrogenase gene," *J. Biol. Chem.,* 263;15335–15341, 1988.

Eshkol, "Mammalian cell-derived recombinant human growth hormone: Pharmacology, metabolism and clinical results," *Hormone Research,* 37:1–3, 1992.

Fanciulli et al., Glycolysis and growth rate in normal and in hexokinase-transfected NIH-3T3 cells," *Oncology Res.,* 6(9): 405–409, 1994.

Fechheimer et al., "Transfection of mammalian cells with plasmid DNA by scrape loading and sonication loading," *Proc. Nat'l Acad. Sci. USA,* 84:8463–8467, 1987.

Felgner, et al., *Arch. Bioch. Biophys.* 182:282–94, 1977.

Ferber, et al., "GLUT-2 Gene Transfer into Insulinoma Cells Confers Both Low and High Affinity Glucose-stimulated insulin Release", *The Journal of Biological Chemistry,* 269:12523–12529, 1994.

Ferkol et al., *FASEB J.,* 7:1081–1091, 1993.

Fiedorek et al., "Selective expression of the insulin I gene in rat insulinoma-derived cell lines," *Mol. Endocrin.,* 4:990–999, 1990.

Fiek et al., "Evidence for identity between hexokinase-binding protein and the mitochondrial porin in the outer membrane of rat liver mitochondria," *Biochem. Biophys. Acta,* 688:429–440, 1982.

Forster & Symons, "Self-cleavage of plus and minus RNAs of a virusoid and a structural model for the active sites," *Cell,* 49:211–220, 1987.

Fort et al., "Various rat adult tissues express only one major species from the glyceraldehyde-3-phosphate-dehydrogenase multigenic family," *Nucleic Acids Research,* 13:1431–1442, 1985.

Fraley et al., "Entrapment of a bacterial plasmid in phospholipid vesicles: Potential for gene transfer," *Proc. Nat'l Acad. Sci. USA,* 76:3348–3352, 1979.

Fricker, "Carboxypeptidase E," *Ann. Rev. Physiology,* 50:309–321, 1988.

Friedmann, "Progress toward human gene therapy," *Science,* 244:1275–1281, 1989.

Fritschy et al., *Diabetes,* 40:37, 1991.

Frougel et al., "Familial hyperglycemia due to mutations in glucokinase," *N. Engl. J. Med.,* 328:105–112, 1993.

Gazdar et al. "Continuous, clonal, insulin- and somatostatin-secreting cell lines established from a transplantable rat islet cell tumor," *Proc. Natl. Acad. Sci. USA,* 77:3519–3523, 1980.

Gelb et al., "Targeting of hexokinase 1 to liver the hepatoma mitochondria," *Proc. Natl. Acad. Sci. USA,* 89:202–206, January, 1992.

Gerlach et al., "Construction of a plant disease resistance gene from the satellite RNA of tobacco ringspot virus," *Nature (London),* 328:802–805, 1987.

German et al., "The insulin and islet amyloid polypeptide genes contain similar cell-specific promoter elements that bind identical β-cell nuclear complexes," *Mol. Cell. Biol.,* 12:1777–1788, 1992.

Ghosh and Bachhawat, "Targeting of liposomes to hepatocytes," In: Wu G. and C. Wu ed. Liver diseases, targeted diagnosis and therapy using specific receptors and ligands. New York: Marcel Dekker, pp. 87–104, 1991.

Ghosh-Choudhury et al., "Protein IX, a minor component of the human adenovirus capsid, is essential for the packaging of full-length genomes," *EMBO J.,* 6:1733–1739, 1987.

Giddings et al., "Effects of glucose on proinsulin messenger RNA in rats in vivo," *Diabetes,* 31:624–629, 1982.

Gomez-Foix et al., "Adenovirus-mediated transfer of the muscle glycogen phosphorylase gene into hepatocytes confers altered regulation of glycogen," *J. Biol. Chem.,* 267:25129–25134, 1992.

Gopal, "Gene transfer method for transient gene expression, stable transfection, and cotransfection of suspension cell cultures," *Mol. Cell Biol.*, 5:1188–1190, 1985.

Gossen et al., "Tight control of gene expression in mammalian cells by tetracycline-responsive promoters," *Proc. Natl. Acad. Sci. USA*, 89:5547–5551, 1992.

Graham & Prevec, "Adenovirus-based expression vectors and recombinant vaccines," *Biotechnology*, 20:363–390, 1992.

Graham and Prevec, "Manipulation of adenovirus vector," In: E. J. Murray (ed.), Methods in Molecular Biology: Gene Transfer and Expression Protocol, Clifton, N.J.: Humana Press, 7:109–128, 1991.

Graham and van der Eb, "A new technique for the assay of infectivity of human adenovirus 5 DNA", *Virology*, 52:456–467, 1973.

Graham et al., "Characteristics of a human cell line transformed by DNA from human adenovirus type 5", *J. Gen. Virol.*, 36:59–72, 1977.

Grampp et al., "Use of regulated secretion in protein production from animal cells: An overview," *Advances in Biochemical Engineering*, 46:35–62, 1992.

Gross et al., "Partial diversion of a mutant proinsulin (B10 aspartic acid) from the regulated to the constitutive secretory pathway in transfected AtT-20 cells," *P.N.A.S.*, 86:4107–4111, 1989.

Grunhaus and Horwitz, "Adenovirus as cloning vector," *Seminar in Virology*, 3:237–252, 1992.

Hakes et al., "Isolation of two complementary deoxyribonucleic acid clones from a rat insulinoma cell line based on similarities to Kex2 and furin sequences and the specific localization of each transcript to endocrine and neuroendocrine tissues in rat," *Endocrinology*, 129:3053–3063, 1991.

Halban, "Structural domains and molecular lifestyles of insulin and its precursors in the pancreatic beta cell," *Diabetologia*, 34:767–778, 1991.

Halban et al., "Abnormal glucose metabolism accompanies failure of glucose to stimulate insulin release from a pancreatic cell line (RINm5f)," *Biochem. J.*, 212:439–443, 1983.

Halban et al., "High-performance liquid chromatography (HPLC): a rapid, flexible and sensitive method for separating islet proinsulin and insulin," *Diabetologia*, 29:893–896, 1986.

Halban et al., "Intracellular degradation of insulin stores by rat pancreatic islets in vitro: An alternative pathway for homeostasis of pancreatic insulin content," *J.B.C.*, 255:6003–6006, 1980.

Harland & Weintraub, "Translation of mammalian mRNA injected into Xenopus oocytes is specifically inhibited by antisense RNA," *J. Cell Biol.*, 101:1094–1099, 1985.

Haseloff, T. and Gerlach, W. L. "Simple RNA enzymes with new and highly specific endoribonuclease activities." *Nature*, 334:585–591, 1988.

Heartlein et al., "Long-term production and delivery of human growth hormone in vivo," *P.N.A.S.*, 91:10967–10971, 1994.

Heinrich et al., "Pre-glucagon messenger ribonucleic acid: Nucleotide and encoded amino acid sequences of the rat pancreatic complementary deoxyribonucleic acid.," *Endocrinology*, 115:2176–2181, 1984.

Hermonat and Muzycska, "Use of adenoassociated virus as a mammalian DNA cloning vector: Transduction of neomycin resistance into mammalian tissue culture cells," *Proc. Nat'l Acad. Sci. USA*, 81:6466–6470, 1984.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol clearance in normal mice," *Proc. Nat'l Acad. Sci. USA* 90:2812–2816, 1993.

Hoppener et al., "Molecular physiology of the islet amyloid polypeptide (IAAP)/amylin gene in man, rat, and transgenic mice," *J. Cell. Biochem.*, 55S: 39–53, 1994.

Horwich et al. "Synthesis of hepadenovirus particles that contain replication-defective duck hepatitis B virus genomes in cultured HuH7 cells," *J. Virol.*, 64:642–650, 1990.

Hosokawa, et al., "Upregulated hexokinase activity in isolated *islets from diabetic 90% pancreatectomized rats." *Diabetes* 44:1328–1333, 1995.

Hughes et al., "Transfection of AtT-20$_{ins}$ Cells with GLUT-2 but Not GLUT-1 Confers Glucose-stimnulated Insulin Secretion", *The Journal of Biological Chemistry*, 268:15205–15212, 1993.

Hughes et al., "Engineering of Glucose-stimulated Insulin Secretion and Biosynthesis in Non-islet Cells", *Proc. Natl. Acad. Sci. USA*, 89:688–692, 1992.

Hughes et al., "Expression of normal and novel glucokinase mrRNA's in anterior pituitary and islet cells," *J. Biol. Chem.*, 266:4521–4530, 1991.

Hughes et al., "Transfection of AtT-2ins cells with GLUT-2 but not GLUT-1 confers glucose-stimulated insulin secretion: relationship to glucose metabolism ," *J.B.C.*, 268:15205–15212, 1993.

Inagaki et al., "Reconstitution of IKATP: An inward retifier subunit plus th e sulfonylurea receptor," *Science*, 270:1166–1170, 1995.

Isaksson et al., "Mode of action of pituitary growth hormone on target cells," *Ann. Rev. Physiol.*, 47:483–499, 1985.

Ishibashi et al., "Hypercholesterolemia in Low Density Lipoprotein Receptor Knockout Mice and its Reversal by Adenovirus-mediated Gene Delivery," *J. Clin. Invest*, 92:883–893, 1993.

Jang et al., "Initiation of protein synthesis by internal entry of ribosomes into the 5' nontranslated region of encephalomyocarditis virus RNA in vivo," *J. Virology*, 63:1651–1660, 1989.

Johnson et al., "Underexpression of Beta cell high $K_m$ glucose transporters in noninsulin-dependent diabetes," *Science*, 250:546–549, 1990.

Jones and Shenk, "Isolation of deletion and substitution mutants of adenovirus type 5," *Cell*, 13:181–188, 1978.

Jonsson et al., "Insulin-promoter-factor 1 is required for pancreas development in mice," *Nature*, 371:606–609, 1994.

Joyce, "RNA evolution and the origins of life," *Nature*, 338:217–244, 1989.

Kabir and Wilson, "Mitochondrial Hexokinase in Brain: Coexistence of Forms Differing in Sensitivity to Solubilization by Glucose-6-Phosphate on the Same Mitochondria," *Arch. Biochem. Biophys.*, 310(2):410–416, 1994.

Kaneda et al., "Increased expression of DNA cointroduced with nuclear protein in adult rat liver," *Science*, 243:375–378, 1989.

Karlsson et al., *EMBO J.*, 5:2377–2385, 1986.

Karlsson et al., "A mutational analysis of the insulin gene transcription control region: expression in β-cells is dependent on two related sequences within the enhancer," *Proc. Natl. Acad. Sci. USA*, 84:8819–8823, 1987.

Karlsson et al., "Individual protein-binding domains of the insulin gene enhancer positively activate β-cell-specific transcription," *Mol. Cell. Biol.*, 9:823–827, 1989.

Kato et al., "Expression of hepatitis β virus surface antigen in adult rat liver," *J. Biol. Chem.,* 266:3361–3364, 1991.

Kaufman et al., "Construction of a modular dihydrofolate reductase cDNA gene: Analysis of signals utilized for efficient expression," *Mol. Cell. Biology,* 2:1304–1319, 1982.

Keller et al., "Insulin prophylaxis in individuals at high risk for the development of type I diabetes mellitus," *Lancet.,* 341:927–928, 1993.

Kennedy et al., "The minisatellite in the diabetes susceptibility locus IDDM2 regulates insulin transcription," *Nature Genetics,* 9:293–298, 1995.

Kim & Cech, "Three dimensional model of the active site of the self-splicing rRNA precursor or Tetrahymena," *Proc. Natl. Acad. Sci. USA,* 84:8788–8792, 1987.

Klein et al., "High-velocity microprojectiles for delivering nucleic acids into living cells," *Nature,* 327:70–73, 1987.

Knaack et al., "Clonal Insulinoma Cell Line That Stably Maintains Correct Glucose Responsiveness," *Diabetes,* 43:1413–1417, December, 1994.

Kreig and Melton, "Functional messenger RNA's are produced by SP6 in vitro transcription of cloned cDNA's," *N.A.R.,* 12:7057–7070, 1984.

Kreymann et al., "Glucagon-like peptide-1 7–36: a physiological incretion in man," *Lancet,* 2:1300–1303, 1987.

Kruse et al., "An endocrine-specific element is an integral component of an exocrine-specific pancreatic enhancer," *Genes and Dev.,* 7:774–786, 1993.

Lacy et al., *Science,* 254:1782–1784, 1991.

Larsson and Litwin, "The growth of polio virus in human diploid fibroblast grown with cellulose microcarriers in suspension culture," *Dev. Biol. Standard.,* 66:385–390, 1987.

Le Gal La Salle et al., "An adenovirus vector for gene transfer into neurons and glia in the brain," *Science,* 259:988–990, 1993.

Leffert et al., "Rat amylin: Cloning and tissue-specific expression in pancreatic islets," *Proc. Natl. Acad. Sci. USA,* 86: 3127–3130, 1989.

Leonard et al., "Characterization of Somatostatin Transactivating Factor-1, a Novel Homeobox Factor That Stimulates Somatostatin Expression in Pancreatic Islet Cells," *Mol Endocrinol,* 7:1275–1283, 1993.

Levrero et al., "Defective and nondefective adenovirus vectors for expressing foreign genes in vitro and in vivo," *Gene,* 101:195–202, 1991.

Li et al., "Effect of disruption of actin filaments by Clostridium botulinum C2 toxin on insulin secretion in HIT-T115 cells and pancreatic islets," *M.B.C.,* 5:1199–1213, 1994.

Liang et al., "Effects of alternate RNA splicing on glucokinase isoform activities in the pancreatic islet, liver, and anterior pituitary," *J.B.C.,* 266:6999–7007, 1991.

Liang et al., "Enhanced and Switchable Expression Systems for Gene-Transfer," *J. Cell. Biochem.* Supplement 21A:379, 1995.

Liang, et al. "Glucose regulates glucokinase activity in cultured islets from rat pancreas." *J. Biol. Chem.* 265:16863–16866, 1990.

Lieber, A. and Strauss, M. "Selection of efficient cleavage sites in target RNAs by using a ribozyme expression library." *Mol. Cell. Biol.,* 15: 540–551, 1995.

Lim, "Encapsulation of biological materials," U.S. Pat. No. 4,352,883, Oct. 5, 1982.

Lin et al., "Pit-1-dependent pituitary cell proliferation involves activation of the growth hormone releasing factor receptor gene," *Nature,* 360:765–768, 1992.

Linden et al., "Pore protein and the hexokinase-binding protein from the outer membrane of rat liver mitochondria are identical," *FEBS Lett.,* 141:189–192, 1982.

Macejak and Sarnow, "Internal initiation of translation mediated by the 5' leader of a cellular mRNA," *Nature,* 353:90–94, 1991.

Madsen, et al., *Proc. Natl. Acad. Sci. U.S.A.,* 85:6652–6656, 1988.

Mann et al., "Construction of a retrovirus packaging mutant and its use to produce helper-free defective retrovirus," *Cell,* 33:153–159, 1983.

Marchetti et al., "Pulsatile insulin secretion from isolated human pancreatic islets," *Diabetes.,* 43:827–830, 1994.

Marie et al., "The pyruvate kinase gene is a model for studies of glucose-dependent regulation of gene expression in the endocrine pancreatic Beta-cell type," *J.B.C.,* 268:23881–23890, 1993.

Markowitz et al., "A safe packaging line for gene transfer: Separating viral genes on two different plasmids," *J. Virol.,* 62:1120–1124, 1988.

Mayo, "Molecular cloning and expression of a pituitary-specific receptor for growth hormone-releasing hormone," *Mol. Endocrinol.,* 1734–1744, 1992.

Meglasson and Matschinsky, "Pancreatic islet glucose metabolism and regulation of insulin secretion," *Diabetes Metab. Rev.,* 2:163–214, 1986.

Michel & Westhof, "Modeling of the three-dimensional architecture of group I catalytic introns based on comparative sequence analysis," *J. Mol. Biol.,* 216:585–610, 1990.

Milgram et al., "Expression of individual forms of peptidylglycine alpha-amidating monooxygenase in AtT-20 cells: Endoproteolytic processing and routing to secretory granules," *J.C.B.,* 117:717–728, 1992.

Miller et al., "IDX-1: a new homeodomain transcription factor expressed in rat pancreatic islets and duodenum that transactivates the somatostatin gene," *EMBO J.,* 13:1145–1156, 1994.

Miyazaki et al., "Establishment of a pancreatic Beta-cell line that retains glucose-inducible insulin secretion: special reference to expression of glucose transporter isoforms, *Endocrinology,* 127:126–132, 1990.

Mizrahi, "Production of human interferons: An overview," *Process Biochem., (August):*9–12, 1983.

Mojsov et al., "Both amidated and nonamidated forms of glucagon-like peptide 1 are synthesized in the rat intestine and the pancreas," *J.B.C.,* 265:8001–8008, 1990.

Mojsov et al., "Preglucagon gene expression in the pancreas and intestine diversifies at the level of post-translational processing," *J.B.C.,* 261:11880–11889, 1986.

Moore et al., "Expressing a human proinsulin cDNA in a mouse ACTH-secreting cell. Intracellular storage, proteolytic processing, and secretion on stimulation," *Cell,* 35:531–538, 1983.

Moore et al., "Secretory protein targeting in a pituitary cell line: Differential transport of foreign secretory proteins to distinct secretory pathways," *J.C.B.,* 101:1773–1781, 1985.

Muir et al., "Antigen specific immunotherapy. Oral tolerance and subcutaneous immunization in the treatment of insulin-dependent diabetes," *Diabetes. Metab. Rev.,* 9:279–287, 1993.

Muir et al., "Insulin immunization of nonobese diabetic mice induces a protective insulitis characterized by diminished intraislet interferon-gamma transcription," *J. Clin. Invest.,* 95:628–634, 1995.

Mulligan, "The Basic Science of Gene Therapy," *Science,* 260:926–932, 1993.

Mulligan et al., "Selection for animal cells that express the Escherichia coli gene coding xanthine-guanine phosphoribosyltransferase," *Proc. Natl. Acad. Sci. USA*, 78:2072–2076, 1981.

Mulligan et al., "Expression of a bacterial gene in mammalian cells," *Science*, 209:1422–1427, 1980.

Newgard, et al., "Metabolic coupling factors in pancreatic Beta-cell signal transduction," *Ann. Rev. Biochem.*, 64:689–719, 1995

Newgard et al., "Glucokinase and glucose transporter expression in liver and islets: implications for control of glucose homeostasis," *Biochem. Soc. Trans.*, 18:851–853, 1990.

Nicolas and Rubinstein, "Retroviral vectors," In: *Vectors: A survey of molecular cloning vectors and their uses*, Rodriguez and Denhardt (eds.), Stoneham: Butterworth, pp. 494–513, 1988.

Nicolau and Sene, "Liposome-mediated DNA transfer in eukaryotic cells," *Biochem. Biophys. Acta*, 721:185–190, 1982.

Nicolau et al., "Liposomes as carriers for in vivo gene transfer and expression," *Methods Enzymol.*, 149:157–176, 1987.

Nilsson and Mosbach, "Immobilized animal cells," *Dev. Biol. Standard.*, 66:183–193, 1987

O'Shea and Sun, *Diabetes* 35:943–946, 1986.

Ogawa et al., "Loss of glucose-induced insulin secretion and GLUT-2 expression in transplanted Beta-cells," *Diabetes*, 44:75–79, 1995.

Ohagi et al., "Identification and analysis of the gene encoding PC2, a prohormone convertase expressed in neuroendocrine tissues," *P.N.A.S.*, 89:4977–4981, 1992.

Ohlsson et al., "IPF1, a homeodomain-containing transactivator of the insulin gene," *EMBO J.*, 12:4251–4259, 1993.

Orci et al., "Evidence that down-regulation of Beta-cell glucose transporters in non-insulin-dependent diabetes may be the cause of diabetic hyperglycemia," *P.N.A.S.*, 87:9953–9957, 1990.

Orskov et al., "Biological effects and metabolic rates of glucagonlike peptide-1 7–36 amide and glucagonlike peptide-1 7–37 in healthy subjects are indistinguishable," *Diabetes*, 42:658–661, 1993.

Orskov et al., "Complete sequence of glucagon-like peptide-1 from human and pig small intestine," *J.B.C.*, 264:12826–12829, 1989.

Ouafik et al., "Developmental regulation of peptidylglycine alpha-amidating monooxygenase (PAM) in rat heart atrium and ventricle," *J.B.C.*, 264:5839–5845, 1989.

Ouafik et al., "The multifunctional peptidylglycine alpha-amidating monooxygenase gene:
Exon/intron organization of catalytic, processing, and routing domains," *Molecular Endocrinology*, 6:1571–1584, 1992.

Owerbach and Aagaard, "Analysis of a 1963-bp polymorphic region flanking the human insulin gene," *GENE*, 32:475–479, 1984.

Palmer et al., "Production of human Factor IX in animals by genetically modified skin fibroblasts: Potential therapy for hemophilia B," *Blood*, 73:438–445, 1989.

Palmer et al., "Genetically modified skin fibroblasts persist long after transplantation but gradually inactivate introduced genes," *Proc. Natl. Acad. Sci. USA*, 88:1330–1334, 1991.

Palukaitis, P. et al., "Characterization of a viroid associated with avocado sunblotch disease." *Virology*, 99:145–151, 1979.

Paskind et al., "Dependence of moloney murine leukemia virus production on cell growth," *Virology*, 67:242–248, 1975.

Pavlakis and Hamer, "Regulation of a metallothionein-growth hormone hybrid gene in bovine papilloma virus," *P.N.A.S.* 80:397–401, 1983.

Peers et al., "Insulin Expression in Pancreatic Islet Cells Relies on Cooperative Interactions between the Helix Loop Helix Factor E47 and the Homeobox Factor STF-1," *Mol Endocrin*, 8:1798–1806, 1994.

Pelletier and Sonenberg, "Internal initiation of translation of eukaryotic mRNA directed by a sequence derived from poliovirus RNA," *Nature*, 334:320–325, 1988.

Perales et al., *Proc. Natl. Acad. Sci. USA*, 91:4086–4090, 1994.

Perriman, R. et al., "Extended target-site specificity for a hammerhead ribozyme." *Gene*, 113:157–163, 1992.

Petricciani, "Should continuous cell lines be used as substrates for biological products?," *Dev. Biol. Standard.*, 66:3–12, 1985.

Philippe et al., "Multipotential phenotypic expression of genes encoding peptide hormones in rat insulinoma lines," *J. Clin. Invest.*, 79:351–358, 1987.

Phillips et al., In: *Large Scale Mammalian Cell Culture* (Feder, J. and Tolbert, W. R., eds.), Academic Press, Orlando, Fla., U.S.A., 1985.

Pieber et al., "Direct plasma radioimmunoassay for rat amylin-(1–37): concentrations with acquired and genetic obesity," *Am. J. Physiol.*, 267:E156–E164, 1994.

Polakis and Wilson, "An Intact Hydrophobic N-Terminal Sequence Is Critical for Binding of Rat Brain Hexokinase to Mitochondria," *Arch. Biochem. Biophys.*, 236(1):328–337, January, 1985.

Potter et al., "Enhancer-dependent expression of human k immunoglobulin genes introduced into mouse pre-B lymphocytes by electroporation," *Proc. Nat'l Acad. Sci. USA*, 81:7161–7165, 1984.

Powell et al., "Efficient targeting to storage granules of human proinsulins with altered propeptide domain," *J.C.B.*, 106:1843–1851, 1988.

Prody, G. A. et al., "Autolytic processing of dimeric plant virus satellite RNA." *Science*, 231, 1577–1580, 1986.

Quaade et al., "Analysis of the protein products encoded by variant glucokinase transcripts via expression in bacteria," *FEBS Lett*, 280:47–52, 1991.

Racher et al., *Biotechnology Techniques*, 9:169–174, 1995.

Radvanyi et al., "Pancreatic beta bells cultured from individual preneoplastic foci in a multistage tumorigenesis pathway: a potentially general technique for isolating physiologically representative cell lines," *Molec. and Cell. Biol.*, 13(7): 4223–4232, 1993.

Ragot et al., "Efficient adenovirus-mediated transfer of a human minidystrophin gene to skeletal muscle of mdx mice," *Nature*, 361:647–650, 1993.

Reinhold-Hurek & Shub, "Self-splicing introns in tRNA genes of widely divergent bacteria," *Nature*, 357:173–176, 1992.

Renan, "Cancer genes: current status, future prospects, and applicants in radiotherapy/oncology," *Radiother. Oncol.*, 19:197–218, 1990.

Rhodes and Alarcon, "What beta-cell defect could lead to hyperproinsulinemia in NIDDM?," *Diabetes*, 43:511–517, 1994.

Rhodes and Halban, "The intracellular handling of insulin-related peptides in isolated pancreatic islets," *Biochem. J.*, 251:23–30, 1988.

Rich et al., "Development and analysis of recombinant adenoviruses for gene therapy of cystic fibrosis," *Hum. Gene Ther.*, 4:461–476, 1993.

Ridgeway, "Mammalian expression vectors," In: Rodriguez RL, Denhardt DT, ed. Vectors: A survey of molecular cloning vectors and their uses. Stoneham: Butterworth, pp. 467–492, 1988.

Rippe et al., "DNA-mediated gene transfer into adult rat hepatocytes in primary culture," Mol. Cell Biol., 10:689–695, 1990.

Rosenfeld et al., "Adenovirus-mediated transfer of a recombinant al-antitrypsin gene to the lung epithelium in vivo," Science, 252:431–434, 1991.

Rosenfeld et al., "In vivo transfer of the human cystic fibrosis transmembrane conductance regulator gene to the airway epithelium," Cell, 68:143–155, 1992.

Rouille et al., "Differential processing of proglucagon by the subtilisin-like prohormone convertases PC2 and PC3 to generate either glucagon or glucagon-like peptide," J.B.C., 270:26488–26496, 1995.

Rouille et al., "Proglucagon is processed to glucagon by prohormone convertase PC2 in alphaTC1-6 cells," P.N.A.S., 91:3242–3246, 1994.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," Proc. Natl. Acad. Sci. USA, 86:9079–9083, 1989.

Sadelain et al., "Prevention of type I diabetes in NOD mice by adjuvant immunotherapy," Diabetes, 39:583–589, 1990.

Sambanis et al., "Use of regulated secretion in protein production from animal cells: An evaluation with the AtT-20 model cell line," Biotechnology and Bioengineering, 35:771–780, 1990.

Sambanis et al., "A model of secretory protein trafficking in recombinant AtT-20 cells," Biotechnology and Bioengineering, 36:280–295, 1991.

Sanke et al., "An islet amyloid peptide is derived from an 89-amino acid precursor by proteolytic processing," J.B.C., 263:17243–17246, 1988.

Santerre et al., "Insulin synthesis in a clonal cell line of simian virus 40-transformed hamster pancreatic beta-cells," P.N.A.S., 78:4339–4343, 1981.

Sarver, et al, "Ribozymes as potential anti-HIV-1 therapeutic agents," Science, 247:1222–1225, 1990.

Sato et al., Proc. Nat'l Acad. Sci. U.S.A. 48:1184–1190, 1962.

Sauer, "Manipulation of transgenes by site-specific recombination: Use of Cre recombinase," Methods in Enzymology, 225:890–900, 1993.

Scanlon et al., "Ribozyme-mediated cleavages of c-fos MRNA reduce gene expression of DNA synthesis enzymes and metallothionein," Proc Natl Acad Sci USA, 88:10591–10595, 1991.

Scharfmann et al., "Long-term in vivo expression of retrovirus-mediated gene transfer in mouse fibroblast implants," P.N.A.S. USA, 88:4626–4630, 1991.

Scharp et al., "Protection of encapsulated human islets implanted without immunosuppression in patients with Type I or Type II diabetes and in nondiabetic control subjects," Diabetes, 43:1167–1170, 1994.

Schmidt et al., "Synthesis and targeting of insulin-like growth factor-1 to the hormone storage granules in an endocrine cell line," J.B.C., 269:27115–27124, 1994.

Schnedl et al., "STZ transport and cytotoxicity: Specific enhancement in GLUT-2-expressing cells," Diabetes, 43:1326–1333, 1994.

Schnetzler et al., "Adaptation to supraphysiological levels of insulin gene expression in transgenic mice: Evidence for the importance of posttranscriptional regulation," J. Clin. Invest., 92:272–280, 1994.

Schwab et al., "Complete amino acid sequence of rat brain hexokinase, deduced from the cloned cDNA, and proposed structure of a mammalian hexokinase," Proc. Natl. Acad. Sci. USA, 86:2563–2567, 1989.

Seeburg, "The human growth hormone gene family: Nucleotide sequences show recent divergence and predict a new polypeptide hormone," DNA, 1;239–249, 1982.

Selden et al., "Implantation of genetically engineered fibroblasts into mice: Implications for gene therapy," Science, 236:714–718, 1987.

Sevarino et al., "Cell-specific processing of preprosomatostatin in cultured neuroendocrine cells," J.B.C., 262:4987–4993, 1987.

Sevarino et al., "Thyrotropin releasing hormone (TRH) precursor processing," J.B.C., 264:21529–21535, 1989.

Shehadeh et al., "Effect of adjuvant therapy on development of diabetes in mouse and man," Lancet., 343:706–707, 1994.

Shimizu et al., "Control of glucose phosphorylation and glucose usage in clonal insulinoma lines," Diabetes, 37:563–568, 1988.

Sioud et al., "Preformed ribozyme destroys tumour necrosis factor mRNA in human cells," J Mol. Biol., 223:831–835, 1992.

Sizonenko and Halban, "Differential rates of conversion of rat proinsulins I and II: Evidence for slow cleavage at the B-chain/C-chain junction of proinsulin II," Biochemistry J., 278:621–625, 1991.

Smeekens and Steiner, "Identification of a human insulinoma cDNA encoding a novel mammalian protein structurally related to the yeast dibasi processing protease Kex2," J.B.C., 265:2997–3000, 1990.

Smith, et al., Arch. Bioch. Biophys. 287:359–366, 1991.

Steiner et al., "The new enzymology of precursor processing endoproteases," J.B.C., 267:23435–23438, 1992.

Stoffers et al., "Alternative mRNA splicing generates multiple forms of peptidyl-glycine alpha-amidating monooxygenase in rat atrium," P.N.A.S., 86:735–739, 1989.

Stoffers et al., "Characterization of novel mRNA's encoding enzymes involved in peptide alpha-amidation," J.B.C., 266:1701–1707, 1991.

Stossel, T., "The Molecular Basis of Blood Diseases," Chapter 14, pp. 499–533, W. B. Saunders Co., Philadelphia, Pa., 1987.

Stratford-Perricaudet and Perricaudet, "Gene transfer into animals: the promise of adenovirus," p. 51–61, In: Human Gene Transfer, Eds, O. Cohen-Haguenauer and M. Boiron, Editions John Libbey Eurotext, France, 1991.

Stratford-Perricaudet et al., "Evaluation of the transfer and expression in mice of an enzyme-encoding gene using a human adenovirus vector," Hum. Gene Ther., 1:241–256, 1990.

Subramani et al., "Expression of the mouse dihydrofolate reductase complementary deoxyribonucleic acid in simian virus 40 vectors," Mol. Cell. Biol., 1:854–864, 1981

Sullivan et al., Science 252:718–721, 1991.

Swarovsky et al., "Sodium butyrate induces neuroendocrine cytodifferentiation in the insulinoma cell line RINm5F," Pancreas, 9:460–468, 1994.

Symons, R. H., "Avocado sunblotch viroid: primary sequence and proposed secondary structure." N.A.R., 9:6527–6537, 1981.

Symons, R. H. "Small catalytic RNAs." Annu. Rev. Biochem., 61:641–671, 1992.

Takeda et al., "Organization of the human GLUT-2 (Pancreatic Beta-cell and hepatocyte) glucose transporter gene," *Diabetes,* 42:773–777, 1993.

Takeuchi et al., "Expression of human pancreatic peptide in heterologous cell lines," *J.B.C.,* 266:17409–17415, 1991.

Temin, "Retrovirus vectors for gene transfer: Efficient integration into and expression of exogenous DNA in vertebrate cell genome," In: *Gene Transfer,* Kucherlapati (ed.), New York: Plenum Press, pp. 149–188, 1986.

Thompson, J. D. et al., "Ribozymes in gene therapy." *Nature Medicine,* 1:277–278, 1995.

Thorens, "Expression cloning of the pancreatic beta cell receptor for the gluco-incretion hormone glucagon-like peptide 1," *P.N.A.S.,* 89:8641–8646, 1992.

Thorens et al., "Cloning and functional expression in bacteria of a novel glucose transporter present in liver, intestine, kidney and beta-pancreatic islet cells." *Cell,* 55:281–290, 1988.

Thorens et al., "The loss of GLUT-2 expression by glucose-unresponsive beta cells of db/db mice is reversible and is induced by the diabetic environment," *J. Clin. Invest.,* 90:77–85, 1992b.

Thorens et al., "Reduced expression of the liver/beta-cell glucose transporter isoform in glucose-insensitive pancreatic beta-cells of diabetic rats," *Proc. Natl. Acad. Sci. USA,* 87:6492–6496, 1990.

Thorne et al., "Expression of mouse proopiomelanocortin in an insulinoma cell line," *J.B.C.,* 264:3545–3552, 1989.

Ting and Lee, "Human gene encoding the 78,000-Dalton glucose-regulated protein and its pseudo gene: Structure, conservation, and regulation," *DNA,* 7:275–286, 1989.

Top et al., "Immunization with live types 7 and 4 adenovirus vaccines. II. Antibody response and protective effect against acute respiratory disease due to adenovirus type 7," *J. Infect. Dis.,* 124:155–160, 1971.

Tur-Kaspa et al., "Use of electroporation to introduce biologically active foreign genes into primary rat hepatocytes," *Mol. Cell Biol.,* 6:716–718, 1986.

Unger, "Diabetic hyperglycemia: Link to impaired glucose transport in pancreatic Beta cells," *Science,* 251:1200–1205, 1991.

Unger and Orci, "Glucagon and the Alpha cell," *N.E.J.M.,* 304:1518–1524, 1981.

Usdin et al., "Gastric inhibitory peptide receptor, a member of the secretin-vasoactive intestinal peptide receptor family, is widely distributed in peripheral organs and the brain," *Endocrinology,* 133:2861–2870, 1993.

van Wezel, "Growth of cell-strains and primary cells on microcarriers in homogeneous culture," *Nature,* 216:64–65, 1967.

Varmus et al., "Retroviruses as mutagens: Insertion and excision of a nontransforming provirus alter the expression of a resident transforming provirus," *Cell,* 25:23–36, 1981.

Vollenweider et al., "Processing of proinsulin by furin, PC2 and PC3 in (co)transfected COS (monkey Kidney) cells," *Diabetes,* 44:1075–1080, 1995.

Waeber et al., "Characterization of the murine high $K_m$ glucose transporter GLUT-2 gene and its transcriptional regulation by glucose in a differentiated insulin-secreting cell line," *J. Biological Chemistry,* 43:26912–26919, 1994.

Wagner et al., *Science,* 260:1510–1513, 1990.

Wang et al., "Design and performance of a packed bed bioreactor for the production of recombinant protein using serum-free medium," Proceeding of the Japanese Society for Animal Cell Technology, 1994.

Wang et al., "High density perfusion culture of hybridoma cells for production of monoclonal antibodies in the CelliGen packed bed reactor, In: *Animal Cell Technology: Basic & Applied Aspects,* S. Kaminogawa et al., (eds), vol. 5, pp463–469, Kluwer Academic Publishers, Netherlands, 1993.

Wang et al., "Modified CelliGen-packed bed bioreactor for hybridoma cell cultures," *Cytotechnology,* 9:41–49, 1992.

Welsh et al., "Stimulation of growth hormone synthesis by glucose in islets of Langerhans isolated from transgenic mice," *J.B.C.,* 261:12915–12917, 1986.

White, et al., *Arch. Bioch. Biophys.* 259:402–411, 1987.

White, et al., *Arch. Bioch. Biophys.* 277:26–34, 1990.

Whitesell et al., "Transport and metabolism of glucose in an insulin-secreting cell line, BetaTC-1," *Biochemistry,* 30:11560–11566, 1991.

Willnow and Herz, "Homologous Recombination for Gene replacement in Mouse Cell Lines," *Methods in Cell Biology,* 43 pt A:305–334, 1994.

Wilson, "Brain hexokinase: A proposed relation between soluble-particulate distribution and activity in vivo," *J. Biol. Chem.,* 243:3640–3647, 1968.

Wilson, "Hexokinases," In: *Reviews of Physiology, Biochemistry and Pharmacology,* Pette, D. (Ed.), 126:65–174, 1994.

Wilson, "Ligand induced confirmations of rat brain hexokinase: Effects of glucose-6-phosphate and inorganic phosphate," *Arch. Biochem. Biophys.,* 159:543–549, 1973.

Wilson, "Regulation of mammalian hexokinase activity," In: *Regulation of Carbohydrate Metabolism,* Beitner, R. (Ed.) Vol. 1, CRC, Boca Raton, 45–81, 1985.

Wong et al., "Appearance of β-lactamase activity in animal cells upon liposome mediated gene transfer," *Gene,* 10:87–94, 1980.

Wu and Wu, "Evidence for targeted gene delivery to HepG2 hepatoma cells in vitro," *Biochemistry,* 27:887–892, 1988.

Wu and Wu, *Adv. Drug Delivery Rev.,* 12:159–167, 1993.

Wu and Wu, "Receptor-mediated in vitro gene transfections by a soluble DNA carrier system," *J. Biol. Chem.,* 262:4429–4432, 1987.

Xie and Wilson, "Rat brain hexokinase: the hydrophobic N-terminus of the mitochondrially bound enzyme is inserted in the lipid bilayer," *Arch. Biochem. Biophys.,* 267:803–810, 1988.

Yang et al., "In vivo and in vitro gene transfer to mammalian somatic cells by particle bombardment," *Proc. Nat'l Acad. Sci. USA,* 87:9568–9572, 1990.

Yang et al., "Cellular immunity to viral antigens limits E1-deleted adenoviruses for gene therapy," *P.N.A.S. USA,* 91:4407–4411, 1994.

Yuan, Y. and Altman, S. "Selection of guide sequences that direct efficient cleavage of mRNA by human ribonuclease P." *Science,* 263:1269–1273, 1994.

Yuan, Y. et al., "Targeted cleavage of mRNA by human RNase P." *P.N.A. S.,* 89:8006–8010, 1992.

Yun and Eipper, "Addition of an endoplasmic reticulum retention/retrieval signal does not block maturation of enzymatically active peptidylglycine alpha-amidating monooxygenase," *J.B.C.,* 270:15412–15416, 1995.

Zelenin et al., "High-velocity mechanical DNA transfer of the chloramphenicol acetyltransferase gene into rodent liver, kidney and mammary gland cells in organ explants and in vivo," *FEBS Lett.,* 280:94–96, 1991.

U.S. Pat. No. 4,892,538

U.S. Pat. No. 5,399,346

U.S. Pat. No. 5,011,472
WO 89/01967
WO 89/01967
WO 90102580
WO 90/02580
WO 90/15637
WO 90/15637
WO 91/10425
WO 91/10425
WO 91/10470
WO 91/10470
EPO 0273085

---

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
      (A) LENGTH: 515 base pairs
      (B) TYPE: nucleic acid
      (C) STRANDEDNESS: single
      (D) TOPOLOGY: linear (xi) SEQUENCE DESCRIPTION: SEQ ID NO:1:

```
GAATTCCGGG GGTCCTTCTG CCATGGCCCT GTGGATGCGC CTCCTGCCCC TGCTGGCGCT    60

GCTGGCCCTC TGGGGACCTG ACCCAGCCGC AGCCTTTGTG AACCAACACC TGTGCGGCTC   120

ACACCTGGTG GAAGCTCTCT ACCTAGTGTG CGGGGAACGA GGCTTCTTCT ACACACCCAA   180

GACCCGCCGG GAGGCAGAGG ACCTGCAGGT GGGGCAGGTG GAGCTGGGCG GGGGCCCTGG   240

TGCAGGCAGC CTGCAGCCCT TGGCCCTGGA GGGGTCCCTG CAGAAGCGTG GCATTGTGGA   300

ACAATGCTGT ACCAGCATCT GCTCCCTCTA CCAGCTGGAG AACTACTGCA ACTAGACGCA   360

GCCCGCAGGC AGCCCCCCAC CCGCCGCCTC CTGCACCGAG AGAGATGGAA TAAAGCCCTT   420

GAACCAGCAA AAAAAAAAAA AAAAAAAAAA AAAAAAAAAA AAAAAAAAAC CCCCCCCCC    480

CCCCCTGCAG CAATGGCAAC AACGTTGCGG AATTC                              515
```

(2) INFORMATION FOR SEQ ID NO:2:

(i) SEQUENCE CHARACTERISTICS:
      (A) LENGTH: 110 amino acids
      (B) TYPE: amino acid
      (C) STRANDEDNESS:
      (D) TOPOLOGY: linear (xi) SEQUENCE DESCRIPTION: SEQ ID NO:2:

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
                100                 105                 110
```

(2) INFORMATION FOR SEQ ID NO:3:

(i) SEQUENCE CHARACTERISTICS:
(A) LENGTH: 359 base pairs
(B) TYPE: nucleic acid
(C) STRANDEDNESS: single
(D) TOPOLOGY: linear (xi) SEQUENCE DESCRIPTION: SEQ ID NO:3:

```
CCGGGGATCC TTCTGCCATG GCCCTGTGGA TGCGCCTCCT GCCCCTGCTG GCGCTGCTGG    60
CCCTCTGGGG ACCTGACCCA GCCGCAGCCT TTGTGAACCA ACACCTGTGC GGCTCACACC   120
TGGTGGAAGC TCTCTACCTA GTGTGCGGGG AACGAGGCTT CTTCTACACA CCCAAGACCC   180
GCCGGGAGGC AGAGGACCTG CAGGTGGGGC AGGTGGAGCT GGGCGGGGGC CCTGGTGCAG   240
GCAGCCTGCA GCCCTTGGCC CTGGAGGGGT CCCTGCAGAA GCGTGGCATT GTGGAACAAT   300
GCAGTACTAG CATCTGCTCC CTCTACCAGC TGGAGAACTA CAGCAACTAG ATCTAGCCC    359
```

(2) INFORMATION FOR SEQ ID NO:4:

(i) SEQUENCE CHARACTERISTICS:
(A) LENGTH: 110 amino acids
(B) TYPE: amino acid
(C) STRANDEDNESS:
(D) TOPOLOGY: linear (xi) SEQUENCE DESCRIPTION: SEQ ID NO:4:

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Ser
                85                  90                  95

Thr Ser Ile Cys Ser Leu Tyr Gln Leu Glu Asn Tyr Ser Asn
            100                 105                 110
```

(2) INFORMATION FOR SEQ ID NO:5:

(i) SEQUENCE CHARACTERISTICS:
(A) LENGTH: 867 base pairs
(B) TYPE: nucleic acid
(C) STRANDEDNESS: single
(D) TOPOLOGY: linear (xi) SEQUENCE DESCRIPTION: SEQ ID NO:5:

```
GGATCCATGA ACAGTGAGGA GCAGTACTAC GCGGCCACAC AGCTCTACAA GGACCCGTGC    60
GCATTCCAGA GGGGCCCGGT GCCAGAGTTC AGCGCTAACC CCCCTGCGTG CCTGTACATG   120
GGCCGCCAGC CCCCACCTCC GCCGCCACCC CAGTTTACAA GCTCGCTGGG ATCACTGGAG   180
CAGGGAAGTC CTCCGGACAT CTCCCCATAC GAAGTGCCCC CGCTCGCCTC CGACGACCCG   240
GCTGGCGCTC ACCTCCACCA CCACCTTCCA GCTCAGCTCG GCTCGCCCA TCCACCTCCC    300
GGACCTTTCC CGAATGGAAC CGAGCCTGGG GGCCTGGAAG AGCCCAACCG CGTCCAGCTC   360
CCTTTCCCGT GGATGAAATC CACCAAAGCT CACGCGTGGA AAGGCCAGTG GGCAGGAGGT   420
GCTTACACAG CGGAACCCGA GGAAAACAAG AGGACCCGTA CTGCCTACAC CCGGGCGCAG   480
```

```
CTGCTGGAGC TGGAGAAGGA ATTCTTATTT AACAAATACA TCTCCCGGCC CCGCCGGGTG      540

GAGCTGGCAG TGATGTTGAA CTTGACCGAG AGACACATCA AAATCTGGTT CCAAAACCGT      600

CGCATGAAGT GGAAAAAAGA GGAAGATAAG AAACGTAGTA GCGGGACCCC GAGTGGGGGC      660

GGTGGGGGCG AAGAGCCGGA GCAAGATTGT GCGGTGACCT CGGGCGAGGA GCTGCTGGCA      720

GTGCCACCGC TGCCACCTCC CGGAGGTGCC GTGCCCCAG GCGTCCCAGC TGCAGTCCGG       780

GAGGGCCTAC TGCCTTCGGG CCTTAGCGTG TCGCCACAGC CCTCCAGCAT CGCGCCACTG      840

CGACCGCAGG AACCCCGGTG AAGATCT                                         867

(2) INFORMATION FOR SEQ ID NO:6:

(i) SEQUENCE CHARACTERISTICS:
        (A) LENGTH: 284 amino acids
        (B) TYPE: amino acid
        (C) STRANDEDNESS:
        (D) TOPOLOGY: linear (xi) SEQUENCE DESCRIPTION: SEQ ID NO:6:

Met Asn Ser Glu Glu Gln Tyr Tyr Ala Ala Thr Gln Leu Tyr Lys Asp
1               5                  10                  15

Pro Cys Ala Phe Gln Arg Gly Pro Val Pro Glu Phe Ser Ala Asn Pro
            20                  25                  30

Pro Ala Cys Leu Tyr Met Gly Arg Gln Pro Pro Pro Pro Pro Pro Pro
        35                  40                  45

Gln Phe Thr Ser Ser Leu Gly Ser Leu Glu Gln Gly Ser Pro Pro Asp
    50                  55                  60

Ile Ser Pro Tyr Glu Val Pro Pro Leu Ala Ser Asp Asp Pro Ala Gly
65                  70                  75                  80

Ala His Leu His His His Leu Pro Ala Gln Leu Gly Leu Ala His Pro
                85                  90                  95

Pro Pro Gly Pro Phe Pro Asn Gly Thr Glu Pro Gly Gly Leu Glu Glu
            100                 105                 110

Pro Asn Arg Val Gln Leu Pro Phe Pro Trp Met Lys Ser Thr Lys Ala
        115                 120                 125

His Ala Trp Lys Gly Gln Trp Ala Gly Gly Ala Tyr Thr Ala Glu Pro
    130                 135                 140

Glu Glu Asn Lys Arg Thr Arg Thr Ala Tyr Thr Arg Ala Gln Leu Leu
145                 150                 155                 160

Glu Leu Glu Lys Glu Phe Leu Phe Asn Lys Tyr Ile Ser Arg Pro Arg
                165                 170                 175

Arg Val Glu Leu Ala Val Met Leu Asn Leu Thr Glu Arg His Ile Lys
            180                 185                 190

Ile Trp Phe Gln Asn Arg Arg Met Lys Trp Lys Lys Glu Glu Asp Lys
        195                 200                 205

Lys Arg Ser Ser Gly Thr Pro Ser Gly Gly Gly Gly Glu Glu Pro
    210                 215                 220

Glu Gln Asp Cys Ala Val Thr Ser Gly Glu Glu Leu Leu Ala Val Pro
225                 230                 235                 240

Pro Leu Pro Pro Pro Gly Gly Ala Val Pro Gly Val Pro Ala Ala
                245                 250                 255

Val Arg Glu Gly Leu Leu Pro Ser Gly Leu Ser Val Ser Pro Gln Pro
            260                 265                 270

Ser Ser Ile Ala Pro Leu Arg Pro Gln Glu Pro Arg
        275                 280
```

(2) INFORMATION FOR SEQ ID NO:7:

(i) SEQUENCE CHARACTERISTICS:
        (A) LENGTH: 677 base pairs
        (B) TYPE: nucleic acid
        (C) STRANDEDNESS: single
        (D) TOPOLOGY: linear (xi) SEQUENCE DESCRIPTION: SEQ ID NO:7:

```
AAGCTTCAGG CTGCCAGCAC ACTATCTGTT ATTGCTGCCA CTGCCCACTG AAAGGGATCT    60

TGAGACATGA GGTGCATCTC CAGGCTGCCA GCTGTTCTCC TCATCCTCTC GGTGGCACTC   120

GGCCACTTGA GAGCTACACC TGTCGGAAGT GGTACCAACC CTCAGGTGGA CAAACGGAAG   180

TGCAACACAG CCACATGTGC CACACAACGT CTGGCAAACT TCTTGGTTCG CTCCAGCAAC   240

AACCTTGGTC CAGTCCTCCC ACCAACCAAT GTGGGATCCA ATACATATGG AAGAGGAAT    300

GTGGCAGAGG ATCCAAATAG GGAATCCCTG GATTTCTTAC TCCTGTAAAG TCAATGTACT   360

CCCGTATCTC TTATTACTTC CTGTGTAAAT GCTCTGATGA TTTCCTGAAT AATGTAACAG   420

TGCCTTCAAC GTGCCTGTGC TTGCTGTGTT TGTAAATTCT TATTCTAAGA CGTGCTTTAA   480

ACTGAGTGTT GATAAAGGTC AGGGTGAATA CCTCTCTAAT CACAACATGT TCTTGGCTGT   540

ACATCGATAT CGTAGGAACA CTTAAAATTT CTGTTTTTAC CTTGTAACTC TATGACTCAA   600

GTTTAACAAT AAAGGAGGGC GTGGGATGGT GGACTTGAAA AGTCATTAAC AGCTCATAGT   660

AAATTTCTGA TTCTAGA                                                 677
```

(2) INFORMATION FOR SEQ ID NO:8:

(i) SEQUENCE CHARACTERISTICS:
        (A) LENGTH: 93 amino acids
        (B) TYPE: amino acid
        (C) STRANDEDNESS:
        (D) TOPOLOGY: linear (xi) SEQUENCE DESCRIPTION: SEQ ID NO:8:

```
Met Arg Cys Ile Ser Arg Leu Pro Ala Val Leu Leu Ile Leu Ser Val
1               5                   10                  15

Ala Leu Gly His Leu Arg Ala Thr Pro Val Gly Ser Gly Thr Asn Pro
            20                  25                  30

Gln Val Asp Lys Arg Lys Cys Asn Thr Ala Thr Cys Ala Thr Gln Arg
        35                  40                  45

Leu Ala Asn Phe Leu Val Arg Ser Ser Asn Asn Leu Gly Pro Val Leu
    50                  55                  60

Pro Pro Thr Asn Val Gly Ser Asn Thr Tyr Gly Lys Arg Asn Val Ala
65                  70                  75                  80

Glu Asp Pro Asn Arg Glu Ser Leu Asp Phe Leu Leu Leu
                85                  90
```

(2) INFORMATION FOR SEQ ID NO:9:

(i) SEQUENCE CHARACTERISTICS:
        (A) LENGTH: 2086 base pairs
        (B) TYPE: nucleic acid
        (C) STRANDEDNESS: single
        (D) TOPOLOGY: linear (xi) SEQUENCE DESCRIPTION: SEQ ID NO:9:

```
GGATCCAAGG CCCAACTCCC CGAACCACTC AGGGTCCTGT GGACAGCTCA CCTAGCTGCA    60

ATGGCTACAG GTAAGCGCCC CTAAAATCCC TTTGGCACAA TGTGTCCTGA GGGGAGAGGC   120
```

```
AGCGACCTGT AGATGGGACG GGGGCACTAA CCCTCAGGGT TTGGGGTTCT GAATGTGAGT      180

ATCGCCATCT AAGCCCAGTA TTTGGCCAAT CTCAGAAAGC TCCTGGCTCC CTGGAGGATG      240

GAGAGAGAAA AACAAACAGC TCCTGGAGCA GGGAGAGTGT TGGCCTCTTG CTCTCCGGCT      300

CCCTCTGTTG CCCTCTGGTT TCTCCCCAGG CTCCCGGACG TCCCTGCTCC TGGCTTTTGG      360

CCTGCTCTGC CTGCCCTGGC TTCAAGAGGG CAGTGCCTTC CCAACCATTC CCTTATCCAG      420

GCTTTTTGAC AACGCTATGC TCCGCGCCCA TCGTCTGCAC CAGCTGGCCT TTGACACCTA      480

CCAGGAGTTT GTAAGCTCTT GGGGAATGGG TGCGCATCAG GGGTGGCAGG AAGGGGTGAC      540

TTTCCCCCGC TGGAAATAAG AGGAGGAGAC TAAGGAGCTC AGGGTTTTTC CCGACCGCGA      600

AAATGCAGGC AGATGAGCAC ACGCTGAGCT AGGTTCCCAG AAAAGTAAAA TGGGAGCAGG      660

TCTCAGCTCA GACCTTGGTG GGCGGTCCTT CTCCTAGGAA GAAGCCTATA TCCCAAAGGA      720

ACAGAAGTAT TCATTCCTGC AGAACCCCCA GACCTCCCTC TGTTTCTCAG AGTCTATTCC      780

GACACCCTCC AACAGGGAGG AAACACAACA GAAATCCGTG AGTGGATGCC TTCTCCCCAG      840

GCGGGGATGG GGGAGACCTG TAGTCAGAGC CCCCGGGCAG CACAGCCAAT GCCCGTCCTT      900

GCCCCTGCAG AACCTAGAGC TGCTCCGCAT CTCCCTGCTG CTCATCCAGT CGTGGCTGGA      960

GCCCGTGCAG TTCCTCAGGA GTGTCTTCGC CAACAGCCTG GTGTACGGCG CCTCTGACAG     1020

CAACGTCTAT GACCTCCTAA AGGACCTAGA GGAAGGCATC CAAACGCTGA TGGGGGTGAG     1080

GGTGGCGCCA GGGGTCCCCA ATCCTGGAGC CCCACTGACT TGAGAGACT GTGTTAGAGA      1140

AACACTGGCT GCCCTCTTTT TAGCAGTCAG GCCCTGACCC AAGAGAACTC ACCTTATTCT     1200

TCATTTCCCC TCGTGAATCC TCCAGGCCTT TCTCTACACT GAAGGGGAGG GAGGAAAATG     1260

AATGAATGAG AAAGGGAGGG AACAGTACCC AAGCGCTTGG CCTCTCCTTC TCTTCCTTCA     1320

CTTTGCAGAG GCTGGAAGAT GGCAGCCCCC GGACTGGGCA GATCTTCAAG CAGACCTACA     1380

GCAAGTTCGA CACAAACTCA CACAACGATG ACGCACTACT CAAGAACTAC GGGCTGCTCT     1440

ACTGCTTCAG GAAGGACATG GACAAGGTCG AGACATTCCT GCGCATCGTG CAGTGCCGCT     1500

CTGTGGAGGG CAGCTGTGGC TTCTAGCTGC CCGGGTGGCA TCCCTGTGAC CCCTCCCAG      1560

TGCCTCTCCT GGCCCTGGAA GTTGCCACTC CAGTGCCCAC CAGCCTTGTC CTAATAAAAT     1620

TAAGTTGCAT CATTTTGTCT GACTAGGTGT CCTTCTATAA TATTATGGGG TGGAGGGGGG     1680

TGGTATGGAG CAAGGGGCCC AAGTTGGGAA GACAACCTGT AGGGCCTGCG GGGTCTATTC     1740

GGGAACCAAG CTGGAGTGCA GTGGCACAAT CTTGGCTCAC TGCAATCTCC GCCTCCTGGG     1800

TTCAAGCGAT TCTCCTGCCT CAGCCTCCCG AGTTGTTGGG ATTCCAGGCA TGCATGACCA     1860

GGCTCAGCTA ATTTTTGTTT TTTTGGTAGA GACGGGGTTT CACCATATTG GCCAGGCTGG     1920

TCTCCAACTC CTAATCTCAG GTGATCTACC CACCTTGGCC TCCCAAATTG CTGGGATTAC     1980

AGGCGTGAAC CACTGCTCCC TTCCCTGTCC TTCTGATTTT AAAATAACTA TACCAGCAGG     2040

AGGACGTCCA GACACAGCAT AGGCTACCTG CCATGGCCCA ACCGGT                    2086
```

(2) INFORMATION FOR SEQ ID NO:10:

(i) SEQUENCE CHARACTERISTICS:
        (A) LENGTH: 217 amino acids
        (B) TYPE: amino acid
        (C) STRANDEDNESS:
        (D) TOPOLOGY: linear (xi) SEQUENCE DESCRIPTION: SEQ ID NO:10:

Met Ala Thr Gly Ser Arg Thr Ser Leu Leu Leu Ala Phe Gly Leu Leu

```
1               5                  10                 15
Cys Leu Pro Trp Leu Gln Glu Gly Ser Ala Phe Pro Thr Ile Pro Leu
             20                  25                 30
Ser Arg Leu Phe Asp Asn Ala Met Leu Arg Ala His Arg Leu His Gln
             35                  40                 45
Leu Ala Phe Asp Thr Tyr Gln Glu Phe Glu Glu Ala Tyr Ile Pro Lys
 50                  55                  60
Glu Gln Lys Tyr Ser Phe Leu Gln Asn Pro Gln Thr Ser Leu Cys Phe
 65                  70                  75                  80
Ser Glu Ser Ile Pro Thr Pro Ser Asn Arg Glu Glu Thr Gln Gln Lys
             85                  90                  95
Ser Asn Leu Glu Leu Leu Arg Ile Ser Leu Leu Leu Ile Gln Ser Trp
            100                 105                 110
Leu Glu Pro Val Gln Phe Leu Arg Ser Val Phe Ala Asn Ser Leu Val
            115                 120                 125
Tyr Gly Ala Ser Asp Ser Asn Val Tyr Asp Leu Leu Lys Asp Leu Glu
            130                 135                 140
Glu Gly Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Arg Lys Asp Met Asp Lys Val Glu Thr Phe Leu Arg Ile Val Gln Cys
            195                 200                 205
Arg Ser Val Glu Gly Ser Cys Gly Phe
210                 215
```

(2) INFORMATION FOR SEQ ID NO:11:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (xi) SEQUENCE DESCRIPTION: SEQ ID NO:11:

```
CCGGATCCAG GTCGACGCCG GCCAAGACAG CACAGACAGA TTGACCTATT GGGGTGTTTC      60
GCGAGTGTGA GAGGGAAGCG CCGCGGCCTG TATTTCTAGA CCTGCCCTTC GCCTGGTTCG     120
TGGCGCCTTG TGACCCCGGG CCCCTGCCGC CTGCAAGTCG AAATTGCGCT GTGCTCCTGT     180
GCTACGGCCT GTGGCTGGAC TGCCTGCTGC TGCCCAACTG GCTGGCAAGA TCTCG          235
```

(2) INFORMATION FOR SEQ ID NO:12:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (xi) SEQUENCE DESCRIPTION: SEQ ID NO:12:

```
GGTACCGGGC CCCCCCTCGA GGTCCTGAGC TAAGAATCCA GCTATCAATA GAAACTATGA      60
AACAGTTCCA GGGACAAAGA TACCAGGTCC CCAACAACTG CAACTTTCTG GGAAATGAGG     120
TGGAAAATGC TCAGCCAAGG AAAAAGAGGG CCTTACCCTC TCTGGGACAA TGATTGTGCT     180
GTGAACTGCT TCATCACGGC ATCTGGCCCC TTGTTAATAA TCTAATTACC CTAGGTCTAA     240
```

```
GTAGAGTTGT TGACGTCCAA TGAGCGCTTT CTGCAGACTT AGCACTAGGC AAGTGTTTGG      300

AAATTACAGC TTCAGCCCCT CTCGCCATCT GCCTACCTAC CCCTCCTAGA GCCCTTAATG      360

GGCCAAACGG CAAAGTCCAG GGGGCAGAGA GGAGGTGCTT TGGACTATAA AGCTAGTGGA      420

GACCCAGTAA CTCCCAAGCT T                                                441
```

(2) INFORMATION FOR SEQ ID NO:13:

(i) SEQUENCE CHARACTERISTICS:
        (A) LENGTH: 1252 base pairs
        (B) TYPE: nucleic acid
        (C) STRANDEDNESS: single
        (D) TOPOLOGY: linear (xi) SEQUENCE DESCRIPTION: SEQ ID NO:13:

```
GGGTATCTTT GCCCCGATGG ATGCTGGGCC TAGCCAGGGG CTCCCAGTCC CCAGGCGTGG       60

GGTAGAAGTT GGACTCTATA GTCACCTAAG GGCCTATGTT GCAGTCCTGG TCTCAGGCAC      120

GCGGCCTGCA GGAGAGGCTT AAAAGAAGAG AAACTGCACA CAATGGCTAG GTCACCGGCG      180

TTAAAGCTAA GCAAACCCAG CGCTACTCCT GGGCAGCAAC TGCAAAGCGT TTCTTCAGGT      240

CCCTCACCTG TAGAATCAGA GCGGTAGTCG CCTCTGCATG TCTGAGTTCT TACATGTCGT      300

AATGTACAAA CACGATTTCC CCTCAATCAC CGCCCGGAAC AGTACCTCCA ACTTCCCAGA      360

CCCGGATGCC CCAAGAGCCA GAGTAGGGTG GGAAAATCGG GACAGGCCCC CAAATTCCAC      420

TCGGGGCCT TGAGCTCTTA CATGGTGTCA CGGGGGCAGG TAGTTTGGGT TTAGCAATGT       480

GAACTCTGAC AATTTGGGAT GTAGAGCTGG TGGGCCATCG TGGGACGCCA AGCATCATCC      540

TTAGAGTTTG GATCCTTTAG GGCAGGCAGG CACAGGGACC CAGTGCGAGA TCAGTGAAGC      600

CGCCCAGTTT CGGCTTCCGC TCTTTTTCCA CGCCCACTTG CGTGCTTCTC AACAGTGTG      660

GATGGGAGGG GTGGGGACG AGCCCTAATC TCCGAGGAAG GGGTGTGGCC CCGTTCGTGT       720

TCTCCAGTTT GTGGCGTCCT GGATCTGTCC TCTGGTCCCC TCCAGATCGT GTCCCACACC     780

CACCCGTTCA GGCATGGCAC TGTGCCGCCA CGCGTGACCG TGCGCTCCTT ACGTGGGGA      840

CGTGCAGGGT GCTGCCTCCT TTCCGGTGCG GGAGGGAGCG GCCGTCTTTC TCCTGCTCTG     900

GCTGGGAAGC CCCAGCCATT GCGCTGCAGA GGAGACTTGC AGCCAATGGG GACTGAGGAA     960

GTGGGCCGGC TGGCGGTTGT CACCCTCCCG GGGACCGGAG CTCCGAGGTC TGGAGAGCGC    1020

AGGCAGACGC CCGCCCCGCC CGGGGACTGA GGGGGAGGAG CGAAGGGAGG AGGAGGTGGA    1080

GTCTCCGATC TGCCGCTGGA GGACCACTGC TCACCAGGCT ACTGAGGAGC CACTGGCCCC    1140

ACACCTGCTT TTCCGCATCC CCCACCGTCA GCATGATCGC CGCGCAACTA CTGGCCTATT    1200

ACTCACCGAG CTGAAGGATG ACCAAGTCAA AAAGGTGAGC CCCGCCGGCG CC            1252
```

(2) INFORMATION FOR SEQ ID NO:14:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (xi) SEQUENCE DESCRIPTION: SEQ ID NO:14:

```
GAATTCTGTT GGGCTCGCGG TTGACCACAA ACTCTTCGCG GTCTTTCCAG TACTCTTGGA       60

TCGGAAACCC GTCGGCCTCC GAACGGTACT CCGCCACCGA GGGACCTGAG CGAGTCCGCA     120

TCGACCGGAT CGGAAAACCT CTCGACTGTT GGGGTGAGTA CTCCCTCTCA AAAGCGGGCA     180

TGACTTCTGC GCTAAGATTG TCAGTTTCCA AAAACGAGGA GGATTTGATA TTCACCTGGC     240
```

```
CCGCGGTGAT GCCTTTGAGG GTGGCCGCGT CCATCTGGTC AGAAAAGACA ATCTTTTTGT       300

TGTCAAGCTT GAGGTGTGGC AGGCTTGAGA TCTGGCCATA CACTTGAGTG ACAATGACAT       360

CCACTTTGCC TTTCTCTCAC ACAGGTGTCC ACTCCCAGGT CCAACTGCAG                  410

(2) INFORMATION FOR SEQ ID NO:15:

(i) SEQUENCE CHARACTERISTICS:
         (A) LENGTH: 175 base pairs
         (B) TYPE: nucleic acid
         (C) STRANDEDNESS: single
         (D) TOPOLOGY: linear (xi) SEQUENCE DESCRIPTION: SEQ ID NO:15:

GATCCCTTCA TCAGGCCATC TGGCCCCTTG TTAATAATCG ACTGACCCTA GGTCTAAGAT       60

CCCTTCATCA GGCCATCTGG CCCCTTGTTA ATAATCGACT GACCCTAGGT CTAAGATCCC       120

TTCATCAGGC CATCTGGCCC CTTGTTAATA ATCGACTGAC CTAGGTCTA AGATC            175

(2) INFORMATION FOR SEQ ID NO:16:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (xi) SEQUENCE DESCRIPTION: SEQ ID NO:16:

TTTCCCCTCG AGCACCGCCC GGAACAGTAC C                                     31

(2) INFORMATION FOR SEQ ID NO:17:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (xi) SEQUENCE DESCRIPTION: SEQ ID NO:17:

GTTGCGCCTC GAGCATGCTG ACGGTGGGGG                                       30

(2) INFORMATION FOR SEQ ID NO:18:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (xi) SEQUENCE DESCRIPTION: SEQ ID NO:18:

GTTGGACTCG AGAGTCACCT AAGGGCCTAT G                                     31

(2) INFORMATION FOR SEQ ID NO:19:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO:19:

GATTGGGAAG ACAATAGCAG GCATGC                                           26

(2) INFORMATION FOR SEQ ID NO:20:
```

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:20:

AGTCGCCTCT GCATGTCTGA GTTC                                              24

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:21:

CTTGAGCTCT TACATGGTGT CACG                                              24

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:22:

TCCCCAGGCG TGGGGTAGAA G                                                 21

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:23:

CAACCGGTGG GACATTTGAG TTGC                                              24

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:24:

CCAAGTCATT ATAGAATCAT AGTC                                              24

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:25:

CCGGATCCCA TGATTGAACA AGAT                                              24

(2) INFORMATION FOR SEQ ID NO:26:

(i) SEQUENCE CHARACTERISTICS:
```

```
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:26:

CCAAGATCTC GCTCAGAAGA ACTC                                            24

(2) INFORMATION FOR SEQ ID NO:27:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (xi) SEQUENCE DESCRIPTION: SEQ ID NO:27:

CCGGATCCAG GTCGACGCCG GCCAA                                           25

(2) INFORMATION FOR SEQ ID NO:28:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (xi) SEQUENCE DESCRIPTION: SEQ ID NO:28:

CGAGATCTTG CCAGCCAGTT GG                                              22

(2) INFORMATION FOR SEQ ID NO:29:

(i) SEQUENCE CHARACTERISTICS:
          (A) LENGTH: 57 base pairs
          (B) TYPE: nucleic acid
          (C) STRANDEDNESS: single
          (D) TOPOLOGY: linear (xi) SEQUENCE DESCRIPTION: SEQ ID NO:29:

GATCCCTTCA TCAGGCCATC TGGCCCCTTG TTAATAATCG ACTGACCCTA GGTCTAA        57

(2) INFORMATION FOR SEQ ID NO:30:

(i) SEQUENCE CHARACTERISTICS:
          (A) LENGTH: 57 base pairs
          (B) TYPE: nucleic acid
          (C) STRANDEDNESS: single
          (D) TOPOLOGY: linear (xi) SEQUENCE DESCRIPTION: SEQ ID NO:30:

GATCTTAGAC CTAGGGTCAG TCGATTATTA ACAAGGGGCC AGATGGCCTG ATGAAGG        57

(2) INFORMATION FOR SEQ ID NO:31:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (xi) SEQUENCE DESCRIPTION: SEQ ID NO:31:

CTCCCAAGCT TAAGTGACCA GCTACAA                                         27

(2) INFORMATION FOR SEQ ID NO:32:

(i) SEQUENCE CHARACTERISTICS:
          (A) LENGTH: 28 base pairs
```

(B) TYPE: nucleic acid
        (C) STRANDEDNESS: single
        (D) TOPOLOGY: linear (xi) SEQUENCE DESCRIPTION: SEQ ID NO:32:

GGGCAACCTA GGTACTGGAC CTTCTATC                                          28

(2) INFORMATION FOR SEQ ID NO:33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:33:

GGGTCTAGAG GACCTGTTCC CACCG                                             25

(2) INFORMATION FOR SEQ ID NO:34:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:34:

GCCGAATTCG AGGAGCAGAG AGCGAAGC                                          28

(2) INFORMATION FOR SEQ ID NO:35:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:35:

GCCAGCAGGG GCAGGAGGCG CATCCACAGG GCCAT                                  35

(2) INFORMATION FOR SEQ ID NO:36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:36:

CCACCTGTCT ACACCTCCTC TC                                                22

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:37:

GTAATCCAGG TGTCGTGACT GC                                                22

(2) INFORMATION FOR SEQ ID NO:38:

(i) SEQUENCE CHARACTERISTICS:
        (A) LENGTH: 24 base pairs
        (B) TYPE: nucleic acid (C) STRANDEDNESS: single
            (D) TOPOLOGY: linear (xi) SEQUENCE DESCRIPTION: SEQ ID NO:38:

CCGGGGATCC TTCTGCCATG GCCC                                            24

(2) INFORMATION FOR SEQ ID NO:39:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (xi) SEQUENCE DESCRIPTION: SEQ ID NO:39:

GGGCTAGATC TAGTTGCTGT AGTTCTCCAG CTGGTAGAGG GAGCAGATGC TAGTACTGCA     60

TTGTTCCAC                                                            69

(2) INFORMATION FOR SEQ ID NO:40:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:40:

GGGCTAGATC TAGTTGCAGT AGTTCTC                                         27

(2) INFORMATION FOR SEQ ID NO:41:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:41:

GGATCCATGA ACAGTGAGGA GCAG                                            24

(2) INFORMATION FOR SEQ ID NO:42:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:42:

AGATCTTCAC CGGGGTTCCT GCGG                                            24

(2) INFORMATION FOR SEQ ID NO:43:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:43:

GGGGATCCGA TATGAAAAAG CCTG                                            24

(2) INFORMATION FOR SEQ ID NO:44:

(i) SEQUENCE CHARACTERISTICS:
            (A) LENGTH: 23 base pairs (B) TYPE: nucleic acid
            (C) STRANDEDNESS: single
            (D) TOPOLOGY: linear (xi) SEQUENCE DESCRIPTION: SEQ ID NO:44:

CGAGATCTAC TCTATTCCTT TGC                                             23

(2) INFORMATION FOR SEQ ID NO:45:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:45:

CCGGATCCCA TGAGCGAAAA AT                                              22

(2) INFORMATION FOR SEQ ID NO:46:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:46:

GGAGATCTTT AGCGACCGGA GAT                                             23

(2) INFORMATION FOR SEQ ID NO:47:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:47:

CCGGATCCAT GGTTCGACCA TTG                                             23

(2) INFORMATION FOR SEQ ID NO:48:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:48:

GGAGATCTGT TAGTCTTTCT TC                                              22

(2) INFORMATION FOR SEQ ID NO:49:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:49:

CCGGATCCAT GAGCTTCAAT AC                                              22

(2) INFORMATION FOR SEQ ID NO:50:

(i) SEQUENCE CHARACTERISTICS:
            (A) LENGTH: 23 base pairs
            (B) TYPE: nucleic acid

```
        (C) STRANDEDNESS: single
        (D) TOPOLOGY: linear (xi) SEQUENCE DESCRIPTION: SEQ ID NO:50:

CCAGATCTGC TCATGCTTGC TCC                                          23
```

VI. CLAIMS

What is claimed is:

1. A method for the production of a polypeptide comprising the steps of:
   (a) providing a eukarvotic secretory host cell;
   (b) inhibiting the production of an endogenous, secreted polypeptide;
   (c) transforming said secretory host cell with an exogenous polynucleotide comprising a gene encoding an exogenous polypeptide, wherein said gene is under the control of a promoter active in eukaryotic cells; and
   (d) culturing said secretory host cell under conditions such that said exogenous polynucleotide expresses said exogenous polypeptide;
   wherein steps (a)–(c) are performed in vitro.

2. The method of claim 1, wherein said promoter is selected from the group consisting of CMV, SV40 IE, RSV LTR, GAPDH and RIP1.

3. The method of claim 1, wherein said exogenous polynucleotide further comprises an adenovirus tripartite 5' leader sequence and intron.

4. The method of claim 3, wherein said intron comprises the 5' donor site of the adenovirus major late transcript and the 3' splice site of an immunoglobulin gene.

5. The method of claim 1, wherein said exogenous polynucleotide further comprises a polyadenylation signal.

6. The method of claim 1, wherein said eukaryotic secretory host cell is a neuroendocrine cell.

7. The method of claim 6, wherein said neuroendocrine cell is an insulinoma cell.

8. The method of claim 7, wherein said insulinoma cell is a rat insulinoma cell.

9. The method of claim 7, wherein said insulinoma cell is a human insulinoma cell.

10. The method of claim 1, wherein said exogenous polypeptide is secreted.

11. The method of claim 10, wherein said exogenous polypeptide is a fusion protein.

12. The method of claim 11, wherein said fusion protein comprises a leader sequence that is not naturally associated with said exogenous polypeptide.

13. The method of claim 10, wherein said exogenous polypeptide is amidated.

14. The method of claim 13, wherein said amidated polypeptide is selected from the group consisting of calcitonin, calcitonin gene related peptide (CGRP), β-calcitonin gene related peptide, hypercalcemia of malignancy factor (1–40) (PTH-rP), parathyroid hormone-related protein (107–139) (PTH-rP), parathyroid hormone-related protein (107–111) (PTH-rP), cholecystokinin (27–33) (CCK), galanin message associated peptide, preprogalanin (65–105), gastrin I, gastrin releasing peptide, glucagon-like peptide (GLP-1), pancreastatin, pancreatic peptide, peptide YY, PHM, secretin, vasoactive intestinal peptide (VIP), oxytocin, vasopressin (AVP), vasotocin, enkephalins, enkephalinamide, metorphinamide (adrenorphin), alpha melanocyte stimulating hormone (alpha-MSH), atrial natriuretic factor (5–28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH).

15. The method of claim 10, wherein said exogenous polypeptide is a hormone.

16. The method of claim 15, wherein said hormone is selected from the group consisting of growth hormone, prolactin, placental lactogen, luteinizing hormone, follicle-stimulating hormone, chorionic gonadotropin, thyroid-stimulating hormone, adrenocorticotropin (ACTH), angiotensin I, angiotensin II, β-endorphin, β-melanocyte stimulating hormone (β-MSH), cholecystokinin, endothelin I, galanin, gastric inhibitory peptide (GIP), glucagon, insulin, lipotropins, neurophysins and somatostatin.

17. The method of claim 1, wherein said endogenous, secreted polypeptide and said exogenous polypeptide are the same.

18. The method of claim 1, wherein said exogenous polypeptide enhances the production and/or secretion of at least one polypeptide produced by said cell.

19. The method of claim 1, wherein said step (c) further comprises contacting said secretory host cell with a polynucleotide comprising a gene for a selectable marker and step (d) further comprises culturing under drug selection, wherein steps (a)–(d) are performed in vitro.

20. The method of claim 19, wherein said selectable marker gene is flanked by LoxP sites.

21. The method of claim 20, further comprising:
   (e) transforming the eukarmotic secretory host cell with a polynucleotide encoding the Cre protein, wherein said polynucleotide is under the control of a promoter active in eukaryotic cells; and
   (f) replicate culturing said cell with and without drug selection;
   wherein steps (a)–(f) are performed in vitro.

22. The method of claim 19, wherein said selectable marker is neomycin and said drug is G418.

23. The method of claim 19, wherein the genes for said exogenous polypeptide and said selectable marker are part of the same polynucleotide.

24. The method of claim 1, wherein said eukarvotic secretory host cell is glucose-responsive.

25. The method of claim 1, wherein said inhibiting of production of said endogenous, secreted polypeptide is effected by interruption of the gene encoding said endogenous, secreted polypetpide.

26. The method of claim 25, wherein said interruption is effected by homologous recombination.

* * * * *

UNITED STATES PATENT AND TRADEMARK OFFICE
CERTIFICATE OF CORRECTION

PATENT NO. : 6,087,129
DATED : July 11, 2000
INVENTOR(S) : Christopher B. Newgard et al.

It is certified that error appears in the above-identified patent and that said Letters Patent is hereby corrected as shown below:

Title page,
Item [57] ABSTRACT,
Please delete the Abstract and replace with the following:
-- The present invention provides methods for production of heterologous polypeptides using a variety of recombinantly engineered secretory cell lines. The common feature of these cell lines is the absence of expression of at least one endogenous polypeptide. The host cell machinery normally used to produce the endogenous polypeptide is then usurped for the purpose of making the heterologous polypeptide. Also described are methods of engineering cells for high level expression, methods of large scale protein production, and methods for treatment of disease in vivo using viral delivery systems and recombinant cell lines. --

Item [56] References Cited, please add the following references:

| | | | | |
|---|---|---|---|---|
| -- 5,175,085 | 12/29/92 | Johnson et al. | 435 | 7.21 |
| 5,427,940 | 06/27/95 | Newgard et al. | 435 | 240.2 |
| 4,987,071 | 01/22/91 | Cech et al. | 435 | 91 |
| 5,073,491 | 12/17/91 | Familletti | 435 | 240.22 |
| 5,093,246 | 03/03/92 | Cech et al. | 435 | 91 |
| 5,116,742 | 05/26/92 | Cech et al. | 435 | 91 |
| 5,149,796 | 09/22/92 | Rossi et al. | 536 | 27 |
| 5,354,855 | 10/11/94 | Cech et al. | 536 | 24.1 |

Andersson et al., "Effects of Glucose on the Ultrastructure and Insulin Biosynthesis of Isolated Mouse Pancreatis Islets Maintained in Tissue Culture," *Diabetologia*, 10:743-753, 1974.

Arguad et al., "Adenovirus-mediated overexpression of liver 6-phosphofructo-2-kinase/fructose-2,6-bisphosphatase in gluconeogenic rat hepatoma cells," J. Biol. Chem., 270:24229-24236, 1995.

Asano et al., "Rabbit Brain Glucose Transporter Responds to Insulin When Expressed in Insulin-Sensitive Chinese Hamster Ovary Cells," J. Biol. Chem., 264(6):3416-3420, 1989.

Asfari et al., "Establishment of 2-Mercaptoethanol-Dependent Differentiated Insulin-Secreting Cell Lines," Endocrinology, 130(1):167-178, 1992.

Atkinson et al., "Insulitis and Diabetes in NOD Mice Reduced by Prophylactic Insulin Therapy," Diabetes, 39:933-937, 1990.

Badman et al., "Processing of Pro-Islet Amyloid Polypeptide (proIAPP) by the Prohormone Convertase PC2," FEBS Letters, 378:227-231, 1996.

UNITED STATES PATENT AND TRADEMARK OFFICE
CERTIFICATE OF CORRECTION

PATENT NO. : 6,087,129
DATED : July 11, 2000
INVENTOR(S) : Christopher B. Newgard et al.

It is certified that error appears in the above-identified patent and that said Letters Patent is hereby corrected as shown below:

Baijal et al., J.E. Arch. Bioch. Biophys., 298:2710-278, 1992.
Becker et al., "Use of recombinant adenovirus for metabolic engineering of mammalian cells," Methods in Cell Biology, Roth, M., Ed New York, Academic Press, 43:1610-189, 1994.
Becker et al., "Use of Recombinant Adenovirus Vectors for High-Efficiency Gene Transfer into the Islets of Langerhans," abstract no. 29, Diabetes, Abstract book, 53rd Annual Meeting, June 12-15, 1993, Las Vegas, NV.
BeltrandelRio et al., "Genetic Engineering of insulin secreting cell lines," In Pancreatic Islet Transplantation Volume 1: Procurement of Pancreatic Islets, Lanza, R.P. and Chick, W.L. Eds., R.G. Landes Co., 15:169-183, 1994.
Burch et al., "Adaptation of Glycolytic Enzymes. Glucose Use and Insulin Release During Fasting and Refeeding," Diabetes, 30:923-928.
Burgess et al., "Constitutive and Regulated Secretion of Proteins," Ann Rev. Cell Biology, 3:243-293, 1987.
Capecchi, Mario R., "Altering the Genome by Homologous Recombination," Science, 244:1288-1292, 1989.
Cassidy and Newgard, "Glucose-stimulated insulin secretion in cell lines," Diab. Nutr. Metab., 7:189-195, 1994.
Chavez et al., "Expression of exogenous proteins in cells with regulated secretory pathways," Methods in Cell Biology, 43 PartA:263-288, 1994.
Chen et al., "Regulated secretion of Prolactin by the mouse cell line Beta TC-3," Biotechnology, 13:1191-1197, 1995.
Chen et al., "Recovery of Glucose-induced insulin secretion in a rat model of NIDDM is not accompanied by return of the B-Cell GLUT2 glucose transporter," Diabetes, 41:1320-1327, 1992.
Clark et al., "Modulation of golucose-induced insulin secretion from a rat clonal β-cell line," Endocrinology, 127(6):2779-2788, 1990.
Clark et al., "Islet cell culture in defined serum-free medium," Endrocinology, 126:1895-1903, 1990.

UNITED STATES PATENT AND TRADEMARK OFFICE
CERTIFICATE OF CORRECTION

PATENT NO. : 6,087,129
DATED : July 11, 2000
INVENTOR(S) : Christopher B. Newgard et al.

It is certified that error appears in the above-identified patent and that said Letters Patent is hereby corrected as shown below:

Courchesne-Smith et al., "Cytoplasmic accumulation of a normally mitochondrial malonyl-CoA decarboxylase by the use of an alternate transcription start site," Arch. Biochem. And Biophys., 298(2):576-586, November, 1992.
Daniel and Wegmann, "Protection of nonobese diabetic mice from diabetes by intranasal or subcutaneous administration of insulin peptide B-(9-23)," Proc. Natl. Acad Sci. USA, 93:956-960, 1996.
Dhanvantari et al., "role of prohormone convertases in the tissue-specific processing of proglucagon," Mol. Endo. 10(4):342-355, 1996.
Efrat, Shimon et al., "Beta-cell lines derived from transfgenic mice expressing a hybrid insulin gene-oncogene," Proc. Natl. Acad. Sci. USA, 85:9037-9041, 1988.
Efrat et al., "Murine insulinoma cell line with normal glucos-eregulated insulin secretion," diabetes, 42:901-907, 1993.
Felgner et al., "Arch. Bioch. Biophys., 182:282-94, 1977.
Ferber et al., "Molecular strategies for the treatment of diabetes," Transplant. Proc., 26(2):363-365, April 1994.
Ferber et al., "Heterogeneity of expression and secretion of native and mutant [Asp B 10] insulain at AtT-20 cells," Mol. Endocrinology, 5:319-326, 1991.
Ferber et al., "GLUT-2 gene transfer into insulinoma cells confers both low and high affinity glucose-stimulated insulin release," J. Biol. Chem., 269(15):11523-11529, April, 1994.
Fiedorek et al., "Selective expression of the insulin I gene in rat insulinoma-derived cell lines," Mol. Endocrinol., 4(7):990-999, 1990.
Fiek et al., "Evidence for identity between hexokinase-binding protein and the mitochondrial porin in the outer membrane of rat liver mitochondria," Biochem. Biophys. Acta, 688:429-440, 1982.
Forster and Symons, "Self-cleavage of plus and minus RNAs of a virusoid and a structural model for the active sites," Cell, 49:211-220, 1987.
Gazdar et al., "Continuous, clonal, insulin- and somatostatin-secreting cell lines established from a transplantable rat islet cell tumor," Proc. Natl. Acad. Sci USA, 77:3519-3523, 1980.
Gelb et al., "Targeting of hexokinase 1 to liver the hepatoma mitochondria," Proc. Natl. Acad. Sci. USA, 89:202-206, 1992

UNITED STATES PATENT AND TRADEMARK OFFICE
CERTIFICATE OF CORRECTION

PATENT NO.    : 6,087,129
DATED         : July 11, 2000
INVENTOR(S)   : Christopher B. Newgard et al.

It is certified that error appears in the above-identified patent and that said Letters Patent is hereby corrected as shown below:

Gerlach et al., "Construction of a plant disease resistance gene from the satellite RNA of tobacco Rinspont virus," Nature (London), 328:802-805, 1987.
Grampp et all, "Use of regulated secretion in protein production from animal cells: an overive," Advances in biochemical engineering, 46:35-62, 1992.
Gross et al., "Partial diversion of a mutant proinsulin (B 10 aspartic acid) from the regulated to the constitutive secretory pathway in transfected AtT-20 cells," Proc. Natl. Acad. Sci. USA, 86:4107-4111, 1989.
Gumbiner and Kelly, "Secretory granules of an anterior pituitary cell line, AtT-20, contain only mature forms fo corticotropin and beta-lipotropin," Proc. Natl. Acad. Sci. USA, 78(1):318-322, 1981.
Hakes et al., "Isolation of two complementary deoxyribonucleic acid clones from a rat insulinoma cell line based on similarities to Kex2 and furin sequences and the specific localization of each transcript to endocrine and neuroendocrine tissues in rat," Endocrinology, 120:3053-3063, 1991.
Halban et al., "Abnormal glucose metabolism accompanies failure of glucose to stimulate insulin release from a pancreatic ell line (RTNm5f)," Biochem. J., 212:439-443.
Heartlein et all., "Long-term production and delivery of human growth hormone in vivo," P.N.A.S., 91:10967-10971, 1994.
Hughes et al., "Engineering of glucose-stimulated insulin secretion and biosynthesis in non-islet cells," Proc. Natl. Acad. Sci. USA 89:688-692, 1992.
Hughes et al., "Expression of normal and novel glucokinase mRNAs in anterior pituitary and islet cells," J. Biol. Chem., 266(7):4521-4530, 1991.
Hughes et al., "Transfection of AtT-20$_{ins}$ cells with GLUT-2 but not GLUT-1 confers glucose-stimulated insulin secretion," J. Biol. Chem., 268(20):15205-15212, 1993.
Inagaki et al., "Reconstitution of IKATP; an inward rectifier subunit plus the sulfonylurea receptor," Science, 270:1166-1170, 1995.
Joyce, "RNA evolution and the origins of life," Nature, 338:217-244, 1989.
Karlsen, et al., "Are proprotein convertases PC2 and PC3 involved in proglucagon processing,?" Abstract No. 353
Keller et al., "Insulin prophylaxis in individuals at high risk of type I diabetes," The Lancet, 341:927-928, 1993.
Kim and Cech, "Three dimensional model of the active site of the self-splicing rRNA precursor or tetrahymena," Proc. Natl. Acad. Sci. USA, 84:8788-8792, 1987.
Knaack et al., "Clonal insulinoma cell line that stably maintains correct glucose responsiveness," diabetes, 43:1413-1417, 1994.

UNITED STATES PATENT AND TRADEMARK OFFICE
CERTIFICATE OF CORRECTION

PATENT NO. : 6,087,129
DATED : July 11, 2000
INVENTOR(S) : Christopher B. Newgard et al.

It is certified that error appears in the above-identified patent and that said Letters Patent is hereby corrected as shown below:

Lacy et al., "Maintenance of normoglycemia in diabetic mice by subcutaneous xenografts of encapsulated islets," Science, 254:1782-1784, 1991.
Leonard et al., "Characterization of somatostatin transactivating factor-1, a novel homobox factor that stimulates somatostatin expression in pancreatic islet cells," Mol. Endocrinol., 7:1275-1283, 1993.
Liang et al., "Effects of alternate RNA splicing on glucokinase isoform activities in the pancreatic islet, liver, and anterior pituitary," J.B.C., 266:6999-7007, 1991.
MacDonald, "Elusive proximal signals of b-Cells for insulin secretion," Diabetes, 39: 1461-1466, 1990.
Marie et al., "Thr pyruvate kinase gene is a model for studies of goucose-dependent regulation of gene expression in the endocrine pancreatic beta-cell type," J.B.C., 268:23881-23890, 1993.
Meglasson and Matschinsky, "Pancreatic islet glucose metabolism and regulation of insulin secretion," Diabetes Metab. Rev., 2:163214, 1986.
Miller et al., "IDX-1: A new homeodomain transcription facator expressed in rat pancreatic islets and duodenum that transactivates the somatostatin gene," EMBO. J., 13:1145-1156, 1994.
Miyazaki et al., "Establishment of a pancreatic b-Cell line that retains glucose-inducible insulin secretion: special reference to expression of glucose transporter isoforms,"
Moore et al., "Expressing a human proinsulin cDNA in a mouse ACTH-secreting cell. Intracellular storage, proteolytic processing, and secretion on stimulation," Cell, 35:5331-583, 1983.
Moore and Kelly, "Secretory protein targeting in a pituitary cell line: Differential transport of foreign secretory proteins to distinct secretory pathways," J. Cell Biol., 101:1773-1781, 1985.
Muir, et al., "Insulin immunization of nonobese diabetic mice induces a protective insulitis characterized by diminished intraislet and interferon-gamma transcription," J. Clin. Invest., 95(2):628-634, 1995.
Newgard et al., "Engineering of glucose-stimulated insulin release in clonal cells. Therapeutic implications," Diab. Nutr. Metab., 5(1):15-20, 1992.
Newgard, "Cellular engineering for the treatment of metabolic disorders: Prospects for therapy in diabetes," Biotechnology, 10:1112-1120, 1992.

UNITED STATES PATENT AND TRADEMARK OFFICE
CERTIFICATE OF CORRECTION

PATENT NO. : 6,087,129
DATED : July 11, 2000
INVENTOR(S) : Christopher B. Newgard et al.

Page 6 of 8

It is certified that error appears in the above-identified patent and that said Letters Patent is hereby corrected as shown below:

Newgard et al., "Molecular engineering of the pancreatic β-cell," J. Labor. Clin. Med., 122(4):356-363, 1993.

Newgard et al., "Molecular engineering of glucose-regulated insulin secretion," In Molecular Biology of Diabetes, Drazin and LeRoit (eds.), Humana Press inc., Totowa, NJ, 6(1):1191-54, 1994.

Newgard, "Perspectives in diabetes: Cellular engineering and gene therapy strategies for insulin replacement in diabets," Diabetes, 43:341-350, 1994.

Newgard and McGarry, "Metabolic coupling factors in pancreatic beta-cell signal transduction," Ann. Rev. Biochem., 64:689-719, 1995.

Ohlsson et al., "IPF1, a homeodomain-containing transactivator of the insulin gene," EMBO. J., 12:4251-4259, 1993.

Pavlakis and Hamer, "Regulation of a metallothionein-.growth hormone hybrid gene in bovine papilloma virus," P.N.A.S. 80:397-401, 1983.

Peers et al., "Insulin expression in pabcreatic islet cells relies on cooperative interactions between the helix loop helix factor E47 and the homneobox factor STF-1," Mol. Endocrin., 8:1798-1806, 1994.

Polakis and Wilson, "An intact hydrophobic N-terminal sequence is critical for binding of rat brain hexokinase to motochondria," Arch. Biochem. Biophys., 236(1):328-337, 1985.

Powell et al., "Efficient targeting to storage granules of human proinsulins with altered propeptide domain," J.C.B., 106:1843-1851, 1988.

Prody et al., "Autolytic-processing of dimeric plant virus satellite RNA," Science, 231:1577-1580, 1986.

Quaade et al., "Analysis of the protein products encoded by variant glucokinase transcripts via expression in bacteria, FEBS Lett., 280:47-52, 1991.

Rapoport et al., "Synthesis of carp proinsulin in xenopus oocytes," Eur. J. Biochem., 87:229-233, 1978.

Rasschaert et al., "Long term in vitro effects of streptozotocin, interleukin-1, and high glucose concentration on the activity of mitochondrial dehydrogenases and the secretion of insulin in pancreatic islets," Endoc., 130(5):3522-3528, 1992.

Sambanis et al., "Multiple episodes of induced secretion of human growth hormone from recombinant ArT-20 cells," cytotechnology, 4:111-119, 1990.

UNITED STATES PATENT AND TRADEMARK OFFICE
CERTIFICATE OF CORRECTION

PATENT NO. : 6,087,129
DATED : July 11, 2000
INVENTOR(S) : Christopher B. Newgard et al.

It is certified that error appears in the above-identified patent and that said Letters Patent is hereby corrected as shown below:

Sambanis et al., "Use of regulated secretion in protein production from animal cells: An evaluation with the AtT-20 model cell line," Biotechnology and Bioengineering, 35:771-780, 1990.
Sambanis et al., "A model of secretory protein trafficking in recombinant AtT-20 cells, Biotechnology and Bioengineering, 36:280-295, 1991.
Scanlon et al., "Ribozyme-mediated cleavages of c-fos mRNA reduce gene expression of DNA synthesis enzymes and metallothionein," Proc. Natl. Acad. Sci. USA, 88:10591-10595, 1991.
Scharp et al., "Protein of encapsulated human islets implanted without immunosuppression in patients with type I or type II diabetes and in nondiabetic control subjects," Diabetes,43:1167-1170, 1994.
Schmidt and Moore, "Synthesis and targeting of insuln-like growth factor-1 to the hormone storage granules in an endocrine cell line," J.B.C., 269:27115-27124, 1994.
Selden et al., "Regulation of insulin-gene expression: implications for gene therapy," N. Engl. J. Med., 317(17):1067-1076, 1987.
Shibasaki et al., "Overexpression of glucose transporter modulates insulin biosynthesis in insulin producing cell line," FEBS Lett., 270(1,2):105-107, 1990.
Shimizu et al., "Control of glucose phosphorylation and glucose usage in clonal insulinoma line," Diabestes, 37:563-568, 1988.
Smeekens and Steiner, "Identification of a human insulinoma cDNA encoding a novel mammalian protein structurally related to the yeast dibasi processing protease Kex2," J. B.C. 265:2997-3000, 1990.
Smith et al., Arch. Bioch. Biophysd, 287:359-366, 1991.
Sullivan et al., "Biohybrid artificial pancreas: long-term implantation studies in diabetic, pancreatectomized dogs," Science, 252:718-721, 1991.
Thorens, "Expression cloning of the pancreatic betacell receptor for the gluco-incretion hormone glucagon-like peptide 1," PNAS, 89:8641-8646, 1992.
Ting and Lee, "Human gene encoding the 78,000 dalton glucose-regulated protein and its pseudogene: structure, conservation and regulation," DNA, 7(4):275-286, 1988.
Usdin et al, "Gastric inhibitory peptide receptor, a member of the secretin-vasocative intestinal peptide receptor family, is widely distributed in peripheral organs and the brain," Endocrinology, 133:2861-2870, 1993.
Whitesell et al,, "Transport and metabolism of glucose in an insulin-secreting cell line, beta TC-1," Biochemistry, 30:11560-11566, 1991.

UNITED STATES PATENT AND TRADEMARK OFFICE
CERTIFICATE OF CORRECTION

PATENT NO.    : 6,087,129
DATED         : July 11, 2000
INVENTOR(S)   : Christopher B. Newgard et al.

It is certified that error appears in the above-identified patent and that said Letters Patent is hereby corrected as shown below:

Wilson, "Brain hexokinase: a proposed relation between soluble-particulate distribution and activity, in vivo," J. Biol. Chem., 243:3640-3647, 1968.
Wilson, "Hexokinases," In review of physiology, biochemistry, and pharmacology, D. Pette (Ed.), 126:54-174, 1994.
Wilson, "Ligand induced confirmations of rat brain hexokinase: efects of glucose-6 phosphate and inorganic phosphate," Arch. Biochem. Biophys., 159:543-549, 1973.
Wilson, "Regulation of mammalian hexokinase activity," In regulation of carbohydrate metabolism, Beitner (Ed.), Vol., CRC, Boca Raton, 45-81, 1985.
Xie and Wilson, "Rat brain hexokinase: the hydrophobic N-terminus of the mitochondrially bound enzyme is inserted in thye lipid bilayer," Arch. Biochem. Biophys, 267:803-810, 1988.
Yip et al., "Translation of messenger ribonucleic acid from isolated pancreatic islets and human insulinomas," Proc. Natl. Acad Sci USA, 72:4777-4779, 1975. --

Signed and Sealed this

Second Day of April, 2002

*Attest:*

JAMES E. ROGAN
*Director of the United States Patent and Trademark Office*

*Attesting Officer*